United States Patent
Kim et al.

(10) Patent No.: US 12,018,318 B2
(45) Date of Patent: Jun. 25, 2024

(54) METHOD AND DEVICE FOR ANALYZING TARGET ANALYTE IN SAMPLE

(71) Applicant: SEEGENE, INC., Seoul (KR)

(72) Inventors: Young Wook Kim, Seoul (KR); Young Yong Park, Seoul (KR); Sung Moon Ko, Seoul (KR); Young Jo Lee, Seoul (KR); Han Bit Lee, Seoul (KR)

(73) Assignee: SEEGENE, INC., Seoul (KR)

( * ) Notice: Subject to any disclaimer, the term of this patent is extended or adjusted under 35 U.S.C. 154(b) by 451 days.

(21) Appl. No.: 16/650,052

(22) PCT Filed: Sep. 28, 2018

(86) PCT No.: PCT/KR2018/011559
§ 371 (c)(1),
(2) Date: Mar. 24, 2020

(87) PCT Pub. No.: WO2019/066572
PCT Pub. Date: Apr. 4, 2019

(65) Prior Publication Data
US 2020/0291462 A1    Sep. 17, 2020

(30) Foreign Application Priority Data

Sep. 28, 2017  (KR) .................. 10-2017-0125908
Oct. 20, 2017  (KR) .................. 10-2017-0136772
(Continued)

(51) Int. Cl.
*C12Q 1/6816* (2018.01)
*G06F 17/18* (2006.01)
(Continued)

(52) U.S. Cl.
CPC .......... *C12Q 1/6816* (2013.01); *G06F 17/18* (2013.01); *G16B 40/10* (2019.02); *G16C 20/20* (2019.02)

(58) Field of Classification Search
None
See application file for complete search history.

(56) References Cited

U.S. PATENT DOCUMENTS 4,683,195 A    7/1987   Mullis et al.
4,683,202 A    7/1987   Mullis
(Continued)

FOREIGN PATENT DOCUMENTS

WO    WO-2011/078441 A1    6/2011
WO    WO-2012/096523 A2    7/2012

OTHER PUBLICATIONS

Rutledge ("Sigmoidal Curve-fitting Redefines Quantitative Real-time PCR with the Prospect of Developing Automated High-throughput Applications", 2004, Nucleic Acids Research, vol. 32, No. 22) (Year: 2004).*

(Continued)

*Primary Examiner* — Roy Y Yi
(74) *Attorney, Agent, or Firm* — Harness, Dickey & Pierce, P.L.C.

(57) ABSTRACT

The present invention relates to a method and device for determining the presence or absence of a target analyte in a sample. The present invention may analyze the target analyte without false results, especially false positive results by using a fitting accuracy of a nonlinear function to a data set as a direct indicator for target analyte analysis.

18 Claims, 20 Drawing Sheets

(30) Foreign Application Priority Data

Oct. 31, 2017 (KR) .................. 10-2017-0143792
Dec. 29, 2017 (KR) .................. 10-2017-0184510

(51) Int. Cl.
*G16B 40/10* (2019.01)
*G16C 20/20* (2019.01)

(56) References Cited

U.S. PATENT DOCUMENTS

| | | | |
|---|---|---|---|
| 4,800,159 | A | 1/1989 | Mullis et al. |
| 5,210,015 | A | 5/1993 | Gelfand et al. |
| 5,538,848 | A | 7/1996 | Livak et al. |
| 5,691,142 | A | 11/1997 | Dahlberg et al. |
| 6,117,635 | A | 9/2000 | Nazarenko et al. |
| 6,194,149 | B1 | 2/2001 | Neri et al. |
| 6,326,145 | B1 | 12/2001 | Whitcombe et al. |
| 6,358,691 | B1 | 3/2002 | Neri et al. |
| 7,537,886 | B1 | 5/2009 | Nazarenko et al. |
| 8,219,324 | B2 | 7/2012 | Kurnik et al. |
| 8,265,883 | B2 | 9/2012 | Gunstream |
| 8,560,247 | B2 | 10/2013 | Lerner |
| 2008/0033701 | A1 | 2/2008 | Kurnik |
| 2009/0119020 | A1 | 5/2009 | Kurnik et al. |
| 2010/0070190 | A1* | 3/2010 | Lerner .................. C12Q 1/686 702/179 |
| 2011/0276317 | A1 | 11/2011 | George |
| 2013/0179090 | A1 | 7/2013 | Conroy et al. |
| 2014/0095080 | A1* | 4/2014 | Kurnik .................. G16B 40/00 702/19 |

OTHER PUBLICATIONS

Chen, "Computer Program for Calculating the Melting Temperature of Degenerate Oligonucleotides Used in PCR or Hybridization" Haoyuan Chen and Guan Zhu BioTechniques 1997 22:6, 1158-1160 (Year: 1997).*
Saiki, R. K., et al.; "Enzymatic Amplification of b-Globin Genomic Sequences and Restriction Site Analysis for Diagnosis of Sickle Cell Anemia", Science 230:1350-1354, 1985.
Tyagi, S., et al.; "Molecular Beacons: Probes that Fluoresce upon Hybridization", Nature BioTechnology, vol. 14, 1996, pp. 303-306.
French, D. J., et al.; "HyBeacon™ probes: a new tool for DNA sequence detection and allele discrimination", Molecular and Cellular Probes (2001) 15, 363-374.
Bernard, P.S., et al.; "Homogeneous Amplification and Variant Detection by Fluorescent Hybridization Probes", Clinical Chemistry, 46, No. 2, 2000.
Nazarenko, I. A., et al.; "A closed tube format for amplification and detection of DNA based on energy transfer", 2516-2521 Nucleic Acids Research, 1997, vol. 25, No. 12.
Whitcombe, D., et al.; "Detection of PCR products using selfprobing amplicons and fluorescence", Nature Biotechnology vol. 17 Aug. 1999, pp. 804-807.
International Search Report from corresponding PCT Application No. PCT/KR2018/011559, dated May 15, 2019.

* cited by examiner

Fig. 5
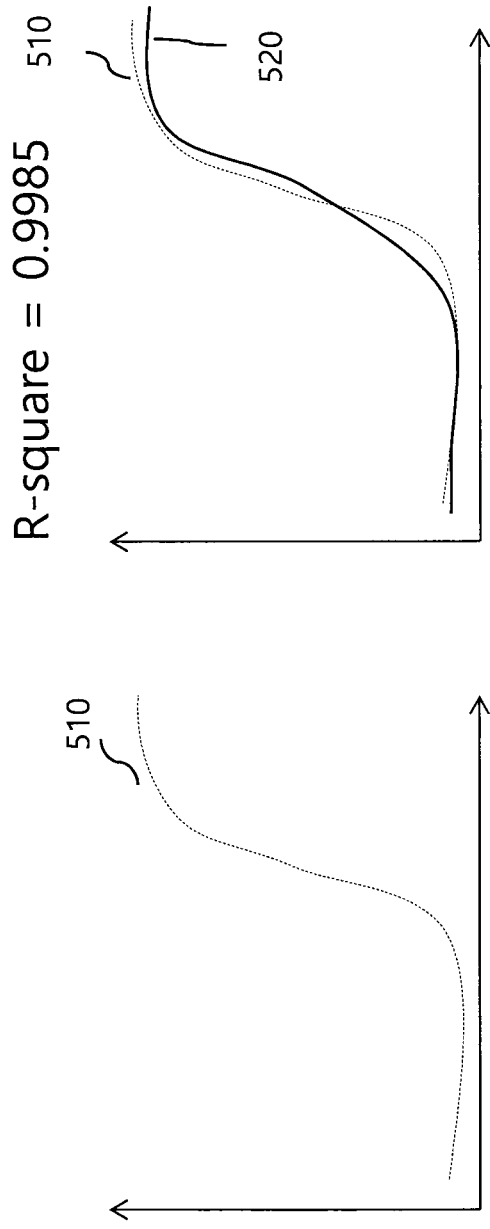
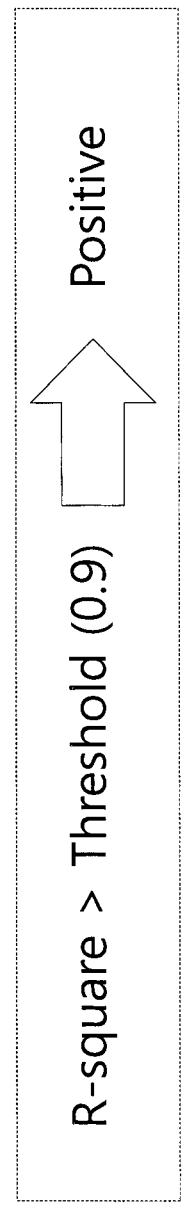

<FAM>

<HEX>

<C610>

<Q670>

METHOD AND DEVICE FOR ANALYZING TARGET ANALYTE IN SAMPLE

This application is a national phase application of PCT/KR2018/011559, filed on Sep. 28, 2018, which claims priority to Korean Patent Application Nos. 10-2017-0125908, filed on Sep. 28, 2017, 10-2017-0136772, filed on Oct. 20, 2017, 10-2017-0143792, filed on Oct. 31, 2017, and 10-2017-0184510, filed on Dec. 29, 2017. The entire disclosures of the applications identified in this paragraph are incorporated herein by references.

FIELD OF THE INVENTION

The present invention relates to a method and a device for analyzing a target analyte in a sample.

BACKGROUND OF THE INVENTION

A polymerase chain reaction (hereinafter referred to as "PCR") which is most widely used for the nucleic acid amplification comprises repeated cycles of denaturation of double-stranded DNA, followed by oligonucleotide primer annealing to the DNA template, and primer extension by a DNA polymerase (Mullis et al., U.S. Pat. Nos. 4,683,195, 4,683,202 and 4,800,159; Saiki et al., (1985) Science 230, 1350-1354).

A real-time polymerase chain reaction is one of PCR-based technologies for detecting a target nucleic acid molecule in a sample in a real-time manner. For detecting a specific target analyte, the real-time PCR uses a signal-generating means for generating a fluorescence signal being detectable in a proportional manner with the amount of the target molecule. Data set including each detection point and signal value at the detection point is obtained. Intensities of the fluorescence signals are proportional with the amount of the target molecule. An amplification curve or amplification profile curve plotting the intensities of the fluorescence signal against detection point is obtained from the data set.

In general, the amplification curve of the real-time PCR may be classified into a baseline region, an exponential phase and a plateau phase. The exponential phase shows increase in fluorescent signals in proportional to increase of amplification products and the plateau phase refers to a region in which there is little increase in fluorescent signals due to saturation of both PCR amplicon and fluorescent signal levels. The baseline region refers to a region in which there is little change in fluorescent signal during initial cycle of PCR. In the baseline region, the level of PCR amplicon is not sufficient to be detectable and therefore signals detected in the baseline region may be due to background signal involving fluorescent signals from reaction reagents and measurement device.

Various methods are developed for determining an existence of amplification of the target analyte from the data set of the real-time PCR. For example, there is a threshold-method. The threshold-method determines a defined signal threshold for all reactions to be analyzed and determines whether a signal of the data set reaches or exceeds the defined signal threshold. The threshold-method determining amplification using the defined signal threshold may have following determination errors: (i) A false-positive determination that occurs when an abnormal signal value or a noise signal value other than a signal value due to amplification reaches a threshold value; (ii) A false-negative determination due to baselining error (iii) A calculation of an erroneous $C_t$ (Cycle Threshold) value by an abnormal signal value or a noise signal value. In addition, the threshold-method has a disadvantage in that it is necessary to collect as many reaction data sets as possible in order to derive a specific signal threshold to be applied to each reaction.

Jeffrey Lerner (U.S. Pat. No. 8,560,247) obtains a function fitted to the data and discloses a method for determining whether a jump error is present according to whether the slope of the function exceeds the maximum amplification slope bound. The method calculates the function fitted to some data in the baseline region, rather than whole data, when calculating the function fitted to the data. The method determines that there is a jump error if the slope of the function fitted to the baseline region of data exceeds the maximum amplification slope boundary. Thus, the method may not determine the presence or absence of a target analyte in a sample using the maximum amplification slope of the function, and may only determine the presence or absence of a jump error.

Ronald T. Kurnik (US Pat. Pub. No. 2009/0119020) discloses a method for determining whether data of growth curve such as a PCR curve represents valid or significant growth. The method obtains a fitted quadratic function by fitting a data and a quadratic function, obtains a statistically meaningful value (e.g., $R^2$ value) for the quadratic function, and determines whether the statistically meaningful value exceeds a preset threshold (e.g. 0.90-0.99). In this method, it is determined that there is no valid or meaningful growth in the data if the statistically significant value exceeds the preset threshold value. The method discards the data if the $R^2$ value is higher than the threshold value, because the more precisely the data is fitted to the quadratic function, the higher the probability that the target analyte is absent in samples. In the method, the fitting of the quadratic function is used only to determine that a target analyte is not present. In order to determine that a target analyte is present, additional step of obtaining $C_t$ values would be needed.

A more effective method is needed as a method for determining whether significant amplification of a target analyte exists in the data obtained from real-time PCR.

A sample analysis using fluorescence signals is performed as follow. When a luminance is supplied with energy through a light source such as LED, electron of the luminance is excited to a higher quantum state, and then the luminance emits a light of specific wavelength by relaxation of the orbital electron to its ground state. Analytical instrument converts the light of specific wavelength to an electric signal using photodiode or CCD and provides information needed for sample analysis.

Although the same amount of a luminance in a sample is generated, each analytical instrument provides different signal values because of the uneven illuminations of the light source (e.g., LED) and the performance variations of the light-electricity conversion device in the respective instruments. Such a signal difference between instruments is called as an inter-instrument variation.

In addition to the inter-instrument variation, the analysis results of a plurality of reactions performed for the same kind and the same amount of the target analyte by a single identical analytical instrument may have variations in signal level because of the difference in reaction environments such as the position of reaction well where the reaction is performed on the instrument or delicate differences in composition or concentration of the reaction mixture. Such a signal difference among the reactions in a single instrument is known as an intra-instrument variation.

For the precise and reliable analysis, such problems have to be solved and several methods are used to solve the problems.

As a most basic solution, a hardware adjustment method is used. For instance, when the analytical instrument is manufactured, the property of some parts of each analytical instrument such as intensity of LED light source is calibrated or adjusted such that the level of an inter-instrument variation for the same sample is reduced and maintained within a proper range. Alternatively, a reference dye method may be used. The reference dye such as ROX™ or fluorescein which constantly generates a known amount of a signal is added in a reaction mixture such that the signal generated from a sample is calibrated based on the level of signal generated from the reference dye.

However, these prior art may have some limitations or shortcomings. The hardware adjustment method shows limited accuracy in calibration and an additional calibration is needed to remove a variation occurred by deterioration of the analytical instrument. Furthermore, the hardware adjustment method may reduce only the inter-instrument variation but may not reduce the intra-instrument variation.

The signal calibration using the reference dye increases the cost per reaction and the quantitative and qualitative variations in the reference dyes used in each reaction may cause another error. Furthermore, the use of the reference dye may increase the possibility of interference phenomenon between the reference dye and other dyes used for determining the presence of target analyte in the reaction mixture. The interference phenomenon is a very important problem, particularly in the multiplex PCR where multiple dyes are used and their fluorescence has to be detected. Besides, assigning one dye and one detection channel for the signal calibration causes a considerable disadvantage in view of the product competitiveness because it results in one less targets simultaneously detectable.

Accordingly, there are strong needs in the art to develop novel approaches for calibrating the data set and reducing the inter- and intra-instrument variations without direct adjusting of hardware or using the reference dye.

For precise and repeatable analyte for the real-time PCR data, it is important for a step of normalization of an obtained amplification curve. The obtained amplification curve is normalized by identifying a baseline region and removing a background signal of the baseline region.

The background signals are different for each reaction because it reflects changes of reaction conditions and environment during the PCR reaction, and baseline drift, which is independent of the amount of nucleic acid in the sample, frequently occurs. Baseline drift makes it difficult to compare amplification curves between reactions and causes false positive and false negative in detecting target nucleic acids. Therefore, in the PCR data analysis, it is necessary to modify the experimental data based on the setting of the baseline region and the baseline.

A conventional method determines an arbitrary cycle region (Ex, 3 to 15 cycles) among initial cycles of the PCR as a baseline, or sets specific cycle region as the baseline by analyzing the amplification curve by experimenter, the specific cycle region was arbitrarily set before the start of the amplification. Another conventional method is to generate a second derivative of the amplification curve and determine the baseline region by using the characteristic point as the end of the baseline (U.S. Pat. No. 8,219,324).

The conventional methods have some disadvantages.

The method of determining all baselines as region of arbitrary cycles may amend changes in different background signals for each reaction, but is not appropriate when baseline drift occurs. Also, since the start of the amplification region depends on the amount of target nucleic acid present in the initial sample, it is not desirable to uniformly apply the predetermined baseline region to various samples if the baseline region is predetermined.

When the experimenter decides the baseline region arbitrarily, the baseline region setting may be changed according to the experimenter who analyzes the same amplification curve. Since the amount of actual amplification product may be changed depending on the experimenter's decision, it is difficult to obtain a reliable result Or the baseline is determined by a complex algorithm according to the other conventional method, the algorithm requires many parameters that are not clearly defined, that often make optimization difficult.

Therefore, in order to obtain objective and accurate experimental results, a new amplification curve amending method is required through setting an objective baseline region for each sample.

For detection of target nucleic acid sequences, real-time detection methods are widely used to detect target nucleic acid sequences with monitoring target amplification in a real-time manner. The real-time detection methods generally use labeled probes or primers specifically hybridized with target nucleic acid sequences. The exemplified methods by use of hybridization between labeled probes and target nucleic acid sequences comprise Molecular beacon method using dual-labeled probes with hairpin structure (Tyagi et al, Nature Biotechnology v.14 Mar. 1996), HyBeacon method (French D J et al., Mol. Cell Probes, 15(6):363-374(2001)), Hybridization probe method using two probes labeled each of donor and acceptor (Bernad et al, 147-148 Clin Chem 2000; 46) and Lux method using single-labeled oligonucleotides (U.S. Pat. No. 7,537,886). TaqMan method (U.S. Pat. Nos. 5,210,015 and 5,538,848) using dual-labeled probes and its cleavage by 5'-nuclease activity of DNA polymerase is also widely employed in the art.

The exemplified methods using labeled primers comprise Sunrise primer method (Nazarenko et al, 2516-2521 Nucleic Acids Research, 1997, v.25 no. 12, and U.S. Pat. No. 6,117,635), Scorpion primer method (Whitcombe et al, 804-807, Nature Biotechnology v.17 Aug. 1999 and U.S. Pat. No. 6,326,145) and TSG primer method (WO 2011/078441).

As alternative approaches, real-time detection methods using duplexes formed depending on the presence of target nucleic acid sequences have been proposed: Invader assay (U.S. Pat. Nos. 5,691,142, 6,358,691 and 6,194,149), PTOCE (PTO cleavage AND extension) method (WO 2012/096523), PCE-SH (PTO Cleavage and Extension-Dependent Signaling Oligonucleotide Hybridization) method (WO 2013/115442), PCE-NH (PTO Cleavage and Extension-Dependent Non-Hybridization) method (PCT/KR2013/012312).

The conventional real-time detection technologies detect signals generated from fluorescent labels at a selected detection temperature in signal amplification process associated with or with no target amplification. When a plurality of target nucleic acid sequences using a single type of label in a single reaction tube are detected in accordance with the conventional real-time detection technologies, generated signals for target nucleic acid sequences are not differentiated from each other. Therefore, the conventional real-time detection technologies generally employ different types of labels for detecting a plurality of target nucleic acid sequences. The melting analysis using Tm difference permits to detect a plurality of target nucleic acid sequences even a single type of label. However, the melting analysis has serious shortcomings in that its performance time is longer than real-time technologies and design of probes with different Tm values becomes more difficult upon increasing target sequences.

Accordingly, where novel methods or approaches being not dependent on melting analysis for detecting a plurality of target nucleic acid sequences using a single type of label in a single reaction vessel and a single type of detector are developed, they enable to detect a plurality of target nucleic acid sequences with dramatically enhanced convenience, cost-effectiveness and efficiency. In addition, the combination of the novel methods with other detection methods e.g., melting analysis) would result in detection of a plurality of target nucleic acid sequences using a single type of label in a single reaction vessel with dramatically enhanced efficiency.

Throughout this application, various patents and publications are referenced and citations are provided in parentheses. The disclosure of these patents and publications in their entities are hereby incorporated by references into this application in order to more fully describe this invention and the state of the art to which this invention pertains.

SUMMARY OF THE INVENTION

The present inventors have made intensive researches to develop a technology for analyzing a target analyte without an error (especially false positive) from data sets obtained from signal-generating reactions. In particularly, the present inventors have made intensive endeavors to overcome problems and disadvantages of conventional methods encountered in setting a threshold value for obtaining a $C_t$ value in a nucleic acid amplification reaction. As a result, the present inventors have found that the fitting accuracy of a nonlinear function for a data set or a processed data set obtained from signal-generating reactions can serve as an indicator of the presence or absence of target analytes in samples. Also, the present inventors have found that the presence or absence of the target analyte can be determined by using the fitting accuracy without setting a threshold value for obtaining a $C_t$ value in a nucleic acid amplification reaction, finally solving the conventional problems described above.

Accordingly, it is an object of the present invention to provide a method for analyzing a target analyte in a sample.

It is another object of the present invention to provide a device for analyzing a target analyte in a sample.

It is still another object of the present invention to provide a computer readable storage medium for performing an analysis of a target analyte in a sample.

Other objects and advantages of the present invention will become apparent from the detailed description to follow taken in conjugation with the appended claims and drawings.

BRIEF DESCRIPTION OF THE DRAWINGS

FIG. 5 illustrates a method for analyzing using a fitting accuracy when a target analyte in a sample is present.

DETAILED DESCRIPTION OF THIS INVENTION

I. Method for Analyzing Target Analytes in Samples Using a Non-Linear Function In one aspect of the present invention, there is provided a method for analyzing a target analyte in a sample, comprising:

obtaining a data set for the target analyte; wherein the data set is obtained from a signal-generating reaction using a signal-generating means and comprises a plurality of data points including cycle numbers and signal values, amending the data set;

generating a non-linear function to the amended data set;

determining a fitting accuracy of the non-linear function to the amended data set; and determining the presence or absence of the target analyte in the sample using the fitting accuracy.

The present invention is directed to a method for analyzing a target analyte, which may be also expressed as a method for detecting a target analyte because an analysis result is ultimately used to detect target analytes.

Figure 3:
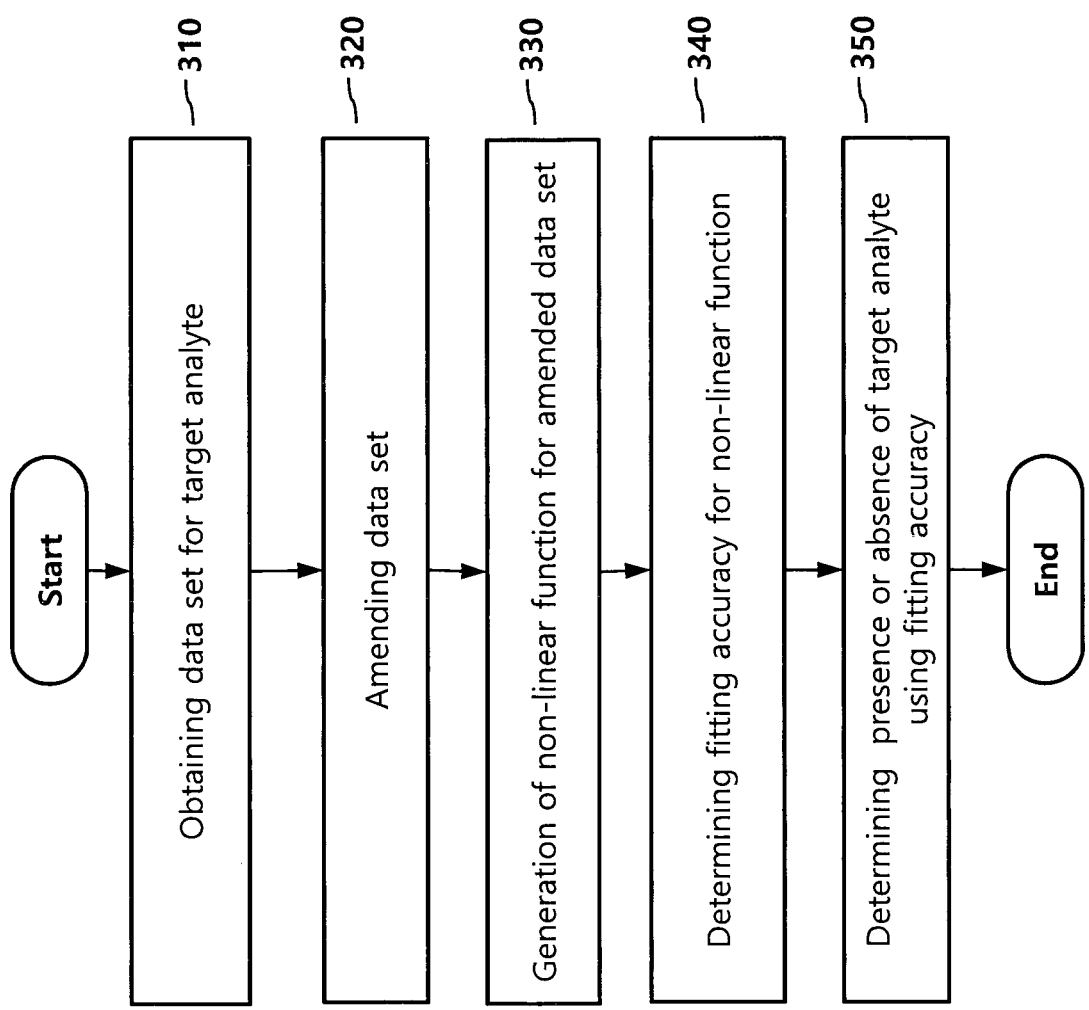
FIG. 3 is a flow chart illustrating a method for analyzing a target analyte according to an exemplary embodiment.

The method of the present invention will be described in detail for each step with referring to FIG. 3 that is a flow chart for the present method.

Obtaining a Data Set for the Target Analyte (Step 310)

A data set for the target analyte is obtained. The data set may be obtained from a signal-generating reaction for the target analyte using a signal-generating means, and the data set comprises a plurality of data points including cycle number and signal value.

The term "target analyte" as used herein may comprise various materials (e.g., biological materials and non-biological materials such as chemicals). Particularly, the target analyte may comprise biological materials such as nucleic acid molecules (e.g., DNA and RNA), proteins, peptides, carbohydrates, lipids, amino acids, biological chemicals, hormones, antibodies, antigens and metabolites. More particularly, the target analyte may be a target nucleic acid molecule.

The term used herein "target nucleic acid molecule", "target nucleic acid", "target nucleic acid sequence" or "target sequence" refers to a nucleic acid sequence of interest for analysis, detection or quantification. The target nucleic acid sequence comprises a sequence in a single strand as well as in a double strand. The target nucleic acid sequence comprises a sequence newly generated in reactions as well as a sequence initially present in a sample.

The target nucleic acid sequence may include any DNA (gDNA and cDNA), RNA molecules and their hybrids (chimera nucleic acid). The sequence may be in either a double-stranded or single-stranded form. Where the nucleic acid as starting material is double-stranded, it is preferred to render the two strands into a single-stranded or partially single-stranded form. Methods known to separate strands includes, but not limited to, heating, alkali, formamide, urea and glycoxal treatment, enzymatic methods (e.g., helicase action), and binding proteins. For instance, strand separation may be achieved by heating at temperature ranging from 80° C. to 105° C. General methods for accomplishing this treatment are provided by Joseph Sambrook, et al., Molecular Cloning, A Laboratory Manual, Cold Spring Harbor Laboratory Press, Cold Spring Harbor, N.Y (2001).

The target nucleic acid sequence includes any naturally occurring prokaryotic, eukaryotic (for example, protozoans and parasites, fungi, yeast, higher plants, lower and higher animals, including mammals and humans), viral (for example, Herpes viruses, HIV, influenza virus, Epstein-Barr virus, hepatitis virus, polio virus, etc.), or viroid nucleic acid. The target nucleic acid sequence may also be any nucleic acid molecule which has been or may be recombinantly produced or chemically synthesized. Thus, the target nucleic acid sequence may or may not be found in nature. The target nucleic acid sequence may comprise a known or unknown sequence.

The term used herein "sample" may comprise biological samples (e.g., cell, tissue and fluid from a biological source) and non-biological samples (e.g., food, water and soil). The biological samples may comprise virus, bacteria, tissue, cell, blood (e.g., whole blood, plasma and serum), lymph, bone marrow aspirate, saliva, sputum, swab, aspiration, milk, urine, stool, vitreous humour, sperm, brain fluid, cerebrospinal fluid, joint fluid, fluid of thymus gland, bronchoalveolar lavage, ascites and amnion fluid. When a target analyte is a target nucleic acid molecule, the sample is subjected to a nucleic acid extraction process (Sambrook, J. et al., Molecular Cloning, A Laboratory Manual, 3rd ed. Cold Spring Harbor Press (2001)). The nucleic acid extraction process may vary depending on type of the sample. Also, when the extracted nucleic acid is RNA, reverse transcription process is performed additionally to synthesize cDNA from the extracted RNA (Sambrook, J. et al., Molecular Cloning, A Laboratory Manual, 3rd ed. Cold Spring Harbor Press (2001)).

The term used herein "signal-generating process" refers to any process capable of generating signals in a dependent manner on a property of a target analyte in a sample. The property may be, for instances, activity, amount or presence (or absence) of the target analyte, in particular the presence or absence of the target analyte in a sample. The signal-generating process may comprise biological and chemical processes. The biological processes may comprise genetic analysis processes such as PCR, real-time PCR, microarray and invader assay, immune assay processes and bacteria growth analysis. The chemical processes may comprise a chemical analysis comprising production, change or decomposition of chemical materials. According to an embodiment, the signal-generating process comprises genetic analysis processes.

According to an embodiment, the signal-generating reaction is a nucleic acid amplification reaction, enzyme reaction or microbial growth.

The signal-generating process may be accompanied with a signal change. The term "signal" as used herein refers to a measurable output.

The progress of the signal-generating reaction is evaluated by measuring the signal. A signal value or signal change may serve as an indicator indicating a property of the target analyte, in particular qualitatively or quantitatively the presence or absence of the target analyte. The signal change may comprise a signal decrease as well as a signal increase.

The term used herein "signal-generating means" refers to any material used in the generation of a signal indicating a property, more specifically the presence or absence of the target analyte which is intended to be analyzed.

A wide variety of the signal-generating means have been known to one of skill in the art. The signal-generating means include a label. The labels may comprise a fluorescent label, a luminescent label, a chemiluminescent label, an electrochemical label and a metal label. A single label or an interactive dual label containing a donor molecule and an acceptor molecule may be used as signal-generating means in the form of linkage to at least one oligonucleotide. Alternatively, an intercalating dye per se may serve as signal-generating means. The signal-generating means may include additional components for generating signals such as nucleolytic enzymes (e.g., 5'-nucleases and 3'-nucleases) and oligonucleotides (e.g., primers and probes).

Examples of the oligonucleotides serving as signal-generating means include oligonucleotides to be specifically hybridized with target nucleic acid sequences (e.g., probes and primers); where probes or primers hybridized with target nucleic acid sequences are cleaved to release a fragment, the oligonucleotides serving as signal-generating means include capture oligonucleotides to be specifically hybridized with the fragment; where the fragment hybridized with the capture oligonucleotide is extended to form an extended strand, the oligonucleotides serving as signal-generating means include oligonucleotides to be specifically hybridized with the extended strand; the oligonucleotides serving as signal-generating means include oligonucleotides to be specifically hybridized with the capture oligonucleotide; and the oligonucleotides serving as signal-generating means include combinations thereof.

According to an embodiment, the signal-generating means may comprise a fluorescence label, more particularly, a fluorescent single label or an interactive dual label comprising donor molecule and acceptor molecule (e.g., an interactive dual label containing a fluorescent reporter molecule and a quencher molecule).

A multitude of methods using the signal-generating means have been known to one of skill in the art. The multitudes of methods generate a signal representing the presence of the target analyte, in particular the target nucleic acid molecule. The methods comprise TaqMan probe method (U.S. Pat. No. 5,210,015), Molecular Beacon method (Tyagi et al., Nature Biotechnology, 14 (3): 303 (1996)), Scorpion method (Whitcombe et al., Nature Biotechnology 17:804-807(1999)), Sunrise or Amplifluor method (Nazarenko et al., Nucleic Acids Research, 25(12): 2516-2521(1997), and U.S. Pat. No. 6,117,635), Lux method (U.S. Pat. No. 7,537,886), CPT (Duck P, et al., Biotechniques, 9:142-148(1990)), LNA method (U.S. Pat. No. 6,977,295), Plexor method (Sherrill C B, et al., Journal of the American Chemical Society, 126:4550-4556(2004)), Hybeacons method (D. 1 French, et al., Molecular and Cellular Probes (2001) 13, 363-374 and U.S. Pat. No. 7,348,141), Dual-labeled, self-quenched probe method (U.S. Pat. No. 5,876,930), Hybridization probe method (Bernard P S, et al., Clin Chem 2000, 46, 147-148), PTOCE (PTO cleavage and extension) method (WO 2012/096523), PCE-SH (PTO Cleavage and Extension-Dependent Signaling Oligonucleotide Hybridization) method (WO 2013/115442) and PCE-NH (PTO Cleavage and Extension-Dependent Non-Hybridization) method (PCT/KR2013/012312) and CER method (WO 2011/037306).

According to an embodiment, the signal-generating reaction is a process amplifying a signal value with or without an amplification of the target nucleic acid molecule.

The term used herein "amplification reaction" refers to a reaction for increasing or decreasing signals.

According to an embodiment of the invention, the amplification reaction refers to an increase (or amplification) of a signal generated depending on the presence of the target analyte by using the signal-generating means. The amplification reaction is accompanied with or without an amplification of the target analyte (e.g., nucleic acid molecule). More particularly, the amplification reaction of the present invention refers to a signal amplification reaction performed with an amplification of the target analyte.

According to an embodiment, the amplification reaction to amplify signals indicative of the presence of the target analyte (e.g., target nucleic acid molecule) may be performed in such a manner that signals are amplified simultaneously with the amplification of the target nucleic acid molecule (e.g., real-time PCR). Alternatively, the amplification reaction may be performed in such a manner that signals are amplified with no amplification of the target analyte [e.g., CPT method (Duck P, et al., Biotechniques, 9:142-148 (1990)) and Invader assay (U.S. Pat. Nos. 6,358, 691 and 6,194,149)].

The target analyte, particularly the target nucleic acid molecule, may be amplified by various methods. For example, a multitude of methods have been known for amplification of a target analyte, including, but not limited to, PCR (polymerase chain reaction), LCR (ligase chain reaction, see U.S. Pat. Nos. 4,683,195 and 4,683,202; PCR Protocols: A Guide to Methods and Applications (Innis et al., eds, 1990)), SDA (strand displacement amplification) (Walker, et al. Nucleic Acids Res. 20(7):1691-6 (1992); Walker PCR Methods Appl 3(1):1-6 (1993)), transcription-mediated amplification (Phyffer, et al., J. Clin. Microbiol. 34:834-841 (1996); Vuorinen, et al., J. Clin. Microbiol. 33:1856-1859 (1995)), NASBA (nucleic acid sequence-based amplification, see Compton, J. Nature 350(6313):91-2(1991)), rolling circle amplification, RCA) (Lisby, Mol. Biotechnol. 12(1):75-99 (1999); Hatch et al., Genet. Anal. 15(2):35-40 (1999)), or Q-beta (Q-Beta Replicase) (Lizard et al., BiolTechnology 6:1197(1988)).

According to an embodiment, the amplification reaction may amplify signals simultaneously with amplification of the target analyte, particularly the target nucleic acid molecule. According to an embodiment, the amplification reaction is performed in accordance with a PCR or a real-time PCR.

According to an embodiment, the signal-generating means generates a signal in a dependent manner on the formation of a duplex. The expression used herein "generate a signal in a dependent manner on the formation of a duplex" in conjunction with signal-generating means refers to that signal to be detected is provided being dependent on association or dissociation of two nucleic acid molecules. Particularly, the signal is generated by a duplex formed in a dependent manner on cleavage of a mediation oligonucleotide specifically hybridized with the target nucleic acid sequence. The term used herein "mediation oligonucleotide" is an oligonucleotide which mediates production of a duplex not containing a target nucleic acid sequence. According to an embodiment of the present invention, the cleavage of the mediation oligonucleotide per se does not generate signal and a fragment formed by the cleavage is involved in successive reactions for signal generation following hybridization and cleavage of the mediation oligonucleotide. According to an embodiment of the present invention, the mediation oligonucleotide includes an oligonucleotide which is hybridized with a target nucleic acid sequence and cleaved to release a fragment, leading to mediate the production of a duplex. Particularly, the fragment mediates a production of a duplex by an extension of the fragment on a capture oligonucleotide. According to an embodiment of the present invention, the mediation oligonucleotide comprises (i) a 3'-targeting portion comprising a hybridizing nucleotide sequence complementary to the target nucleic acid sequence and (ii) a 5'-tagging portion comprising a nucleotide sequence non-complementary to the target nucleic acid sequence. According to an embodiment of the present invention, the cleavage of a mediation oligonucleotide release a fragment and the fragment is specifically hybridized with a capture oligonucleotide and extended on the capture oligonucleotide. According to an embodiment of the present invention, a mediation oligonucleotide hybridized with target nucleic acid sequences is cleaved to release a fragment and the fragment is specifically hybridized with a capture oligonucleotide and the fragment is extended to form an extended strand, resulting in formation of a extended duplex between the extended stand and the capture oligonucleotide providing a signal indicating the presence of the target nucleic acid sequence. The representative example of the signal-generating means generating a signal in a dependent manner on the formation of a duplex is PTOCE method (WO 2012/096523).

According to an embodiment, the signal-generating means generates a signal in a dependent manner on cleavage of a detection oligonucleotide. Particularly, the signal is generated by hybridization of the detection oligonucleotide with a target nucleic acid sequence and then cleavage of the detection oligonucleotide. The signal by hybridization of the detection oligonucleotide with a target nucleic acid sequence and then cleavage of the detection oligonucleotide may be generated by various methods, including TaqMan probe method (U.S. Pat. Nos. 5,210,015 and 5,538,848).

The data set obtained from an amplification reaction comprises an amplification cycle or cycle number.

The term used herein "cycle" refers to a unit of changes of conditions in a plurality of measurements accompanied with changes of conditions. For example, the changes of conditions refer to an increase or decrease of temperature, reaction time, reaction number, concentration, pH and/or replication number of a measured subject (e.g., target nucleic acid molecule). Therefore, the cycle may refer to a time or a process cycle, a unit operation cycle and a reproductive cycle.

For example, when measuring a substrate decomposition ability of the enzyme according to a concentrate of the substrate, a degree of the substrate decomposition of the enzyme is measured several times by varying the concentrate of the substrate, and then, the substrate decomposition ability of the enzyme is analyzed. At this time, the change of the constant condition is the increase of the concentration of the substrate, and the unit used for increasing the concentration of the substrate is set to one cycle.

For another example, when an isothermal amplification of nucleic acid is performed, the signals of a single sample are measured multiple times with a regular interval of times under isothermal conditions. In this reaction, the reaction time may correspond to the changes of conditions and a unit of the reaction time may correspond to a cycle.

Particularly, when repeating a series of reactions or repeating a reaction with a time interval, the term "cycle" refers to a unit of the repetition.

For example, in a polymerase chain reaction (PCR), a cycle refers to a reaction unit comprising denaturation of a target nucleic acid molecule, annealing (hybridization) between the target nucleic acid molecule and primers and primer extension. The increases in the repetition of reactions may correspond to the changes of conditions and a unit of the repetition may correspond to a cycle.

The data set obtained from a signal-generating process comprises a plurality of data points comprising cycle numbers and signal values.

The term used herein "values of signals" or "signal values" means either values of signals (e.g., intensities of signals) actually measured at the cycles of the signal-generating process (e.g., actual value of fluorescence intensity processed by amplification reaction) or their modifications. The modifications may comprise mathematically processed values of measured signal values. Examples of mathematically processed values of measured signal values may comprise logarithmic values and derivatives of measured signal values. The derivatives of measured signal values may comprise multi-derivatives.

The term used herein "data point" means a coordinate value comprising cycle numbers and signal values. The term used herein "data" means any information comprised in data set. For example, each of cycles and signal values of an amplification reaction may be data.

The data points obtained from a signal-generating process, particularly from an amplification reaction may be plotted with coordinate values in a rectangular coordinate system. In the rectangular coordinate system, the X-axis represents cycles of the amplification reaction and the Y-axis represents signal values measured at each cycles or modifications of the signal values.

The term used herein "data set" refers to a set of data points. For example, the data set may comprise a raw data set which is a set of data points obtained directly from the signal-generating process (e.g., an amplification reaction) using a signal-generating means. Alternatively, the data set may be a modified data set which is obtained by a modification of the data set including a set of data points obtained directly from the signal-generating process. The data set may comprise an entire or a partial set of data points obtained from the signal-generating process or modified data points thereof.

The data set may be plotted and the amplification curve may be obtained from the data set.

According to an embodiment, the method of the present invention further comprises the step of performing a signal-generating reaction to obtain the data set.

Amending the Data Set (Step 320)

The data set thus obtained is amended. The amended data set may be provided by normalizing the data set (normalization process) or removing a noise in the data set (noise removal process). According to an embodiment, the data set is amended by using both a normalization process and a noise removal process. The normalization process may be performed before or after the noise removal process.

(A) Normalization of Data Sets

The data set may be normalized by various methods known to one skilled in the art.

According to an embodiment, the normalization of the data set is performed by the SBN method disclosed in WO 2017/086762 that had been previously developed by the present Applicant. It would be understood by one of skill in the art that the application of the SBN method to the present invention using a non-linear fitting function may be easily carried out by one of skill in the art by referring to descriptions of WO 2017/086762 and the present patent Application. In brief, the SBN method will be described hereinbelow.

According to an embodiment, the normalization of the data set is performed by the steps comprising generating a normalization coefficient using (i) a signal value at a reference cycle or (ii) a change value of the signal value at the reference cycle; and generating the amended data set by applying the normalization coefficient to signal values of the data set. The data set may be denoted by a first data set and the normalized data set may be denoted by a second data set.

(A-1) Generating the Normalization Coefficient

The normalization coefficient is generated by using (i) the signal value at the reference cycle or (ii) the modification of the signal value at the reference cycle.

The signal value at the reference cycle may be the normalization coefficient. The data set is normalized by applying the signal value at the reference cycle to the signal values of the data set to normalize the data set. For example, the signal values of the data set may be divided by the signal value at the reference cycle.

When the normalized coefficient is generated by using the modification of the signal value at the reference cycle, the normalization coefficient may be determined using the relationship between the signal value at the reference cycle and the reference value. The relationship between the signal value at the reference cycle and the reference value may be a difference between the signal value at the reference cycle and the reference value. Particularly, the difference between the signal value at the reference cycle and the reference value is the ratio between the signal value at the reference cycle to the reference value. According to an embodiment, normalizing the data set using the modification may be division of the signal values of the data set by the modification.

According to one embodiment, the reference cycle is one cycle or a plurality of cycles. Particularly, cycle 5 of the data set may be selected as the reference cycle. Alternatively, cycles 4, 5 and 6 may be selected as the reference cycle. When the reference cycle is a plurality of cycles, the average value of the signal values at the plurality of cycles may be used as the signal value at the reference cycle.

The reference cycle may a cycle at which no signal amplification is detected in the signal-generating reaction. For example, where data sets are obtained by a nucleic acid amplification reaction, the reference cycle may be specifically selected in a baseline region.

According to an embodiment, the signal-generating reaction is a reaction including a baseline region and a signal amplification region, and the reference cycle is located in the baseline region. The reference cycle of the present invention may be a cycle less than of cycle 50, 40, 30, 20, 19, 18, 17, 16, 15, 14, 13, 12, 11, 10, 9 or 8. Specifically, the reference cycle may be determined as a cycle among cycles 1-30, cycles 2-30, cycles 2-20, cycles 2-15, cycles 2-10, cycles 2-8, cycles 3-30, cycles 3-20, cycles 3-15, cycles 3-10, cycles 3-9, cycles 3-8, cycles 4-8 cycles or cycles 5-8.

According to an embodiment, the reference cycle is a single cycle. Further, the reference cycle may comprise two or more cycles and therefore the signal value at the reference cycle comprises a plurality of signal values.

For example, the $4^{th}$, $5^{th}$ and $6^{th}$ cycles may be designated as the reference cycle, and the average value of signal values at the reference cycles may be used as a signal value to provide a normalization coefficient.

While the signal value at the reference cycle as it is may be used as the normalization coefficient, the modification of the signal value at the reference cycle may also be used.

According to an embodiment, the modification may be provided by determining the relationship between the signal value at the reference cycle and the reference value. Where the modification is determined by the ratio between the signal value at the reference cycle and the reference value, the modification may be provided by Equation I.

$$\text{Modification} = \frac{\text{signal value in reference cycle}}{\text{reference value}} \quad \text{Equation I}$$

For example, when the reference cycle is the $5^{th}$ cycle, the signal value at the $5^{th}$ cycle is RFU 13,285 and the reference value is RFU 9000, the modification may be 1.48.

The reference value may be arbitrarily determined. Particularly, the reference value is arbitrarily set to a real number other than 0 and 1. According to an embodiment, the reference value is determined within the average±standard deviation (SD) of signal values at the cycles.

According to an embodiment, the reference value is determined by (i) a ratio of a total signal change value of a standard data set to a reference total signal change value; wherein the standard data set is obtained from a signal-generating reaction for a target analyte of known concentration; and (ii) the standard data set. Particularly, the signal value at the reference cycle of the standard data set may be amended using a ratio of the total signal change value of the standard data set to the reference total signal change value, followed by determining a reference value from the signal value at the reference cycle of the amended standard data set. In an example, the signal value at the reference cycle of the amended standard data set is determined as the reference value.

The standard data set refers to a data set obtained by performing the signal-generation reaction for the target analyte of known concentration.

According to an embodiment of the present invention, the data set may be amended by using a total signal change value. The term used herein "total signal change value" means a signal change amount (increased or decreased) of the data set. When the total signal change value is determined within a region of the data set, the total signal change value may be a difference between the first cycle and the last cycle of the region of the data set or a difference between the maximum signal value and the minimum signal value of the region of the data set.

Constant total signal change values may be obtained theoretically from the same or different instruments when signal-generating reactions are performed using target analytes of an identical concentration under an identical condition. Therefore, the amendment based on the total signal change value may reduce a variation between a plurality of the data sets.

According to an embodiment of the present invention, the reference total signal change value may be a total signal change value of the standard data set obtained from a signal-generating reaction which is different from that used for obtaining the data set from the signal-generating reaction for the target analyte. The reference total signal change value of the present invention may be determined by a data set obtained from a signal-generating reaction for the target analyte of known concentration.

The normalization coefficient may be provided by dividing the signal value at the reference cycle of the data set to be normalized by the reference value.

(A-2) Applying the Normalization Coefficient to the Data Set

The normalized data set is generated by applying the normalization coefficient to the data set. There are various ways to apply the normalization coefficient to the data set. When the normalization coefficient is determined as a ratio, the normalized data set may be generated by applying the normalization coefficient as shown in Equation II.

$$\text{Signal value of second data set} = \frac{\text{signal value of first data set}}{\text{normalization coefficient}} \quad \text{Equation II}$$

In Equation II, the first data set is a data set before normalization and the second data set is a data set after normalization.

According to an embodiment, the signal-generating reaction comprises a plurality of signal-generating reactions for an identical target analyte in different reaction environments; wherein the data set is a plurality of data sets obtained from the plurality of sets from the plurality of signal-generating reactions; and wherein the reference cycle or the reference cycle plus the reference value are applied to the plurality of data sets in the same manner. According to an embodiment, the plurality of signal-generating reactions are performed in different reaction environments comprising different devices, different reaction tubes or wells, different samples, different amounts of the target analyte or difference primers or probes from each other.

According to an embodiment, the amended data set is generated (i) by generating a normalized data set by applying the normalization coefficient to the data set or (ii) by baselining the data set or the normalized data set.

(B) Removing a Noise in the Data Set (B-1) Baselining (B-1-a) Conventional Baselining Methods According to an embodiment of this invention, the data set or the normalized data set may be baselined for removing a background signal from the data set or the normalized data set. The baseline subtracted data set may be obtained by methods well known in the art (e.g., U.S. Pat. No. 8,560,240 and WO 2016052991).

(B-1-b) Baselining Using a Quadratic Function Having a Symmetry Axis

This approach is a novel method for baselining developed by the present Applicant.

Data sets including the pre-normalized data set and post-normalized data set may be baselined by using a quadratic function having a symmetry axis. The baselining of the data set using the quadratic function is to amend the data set by subtract a quadratic function value from the data set.

The generation of the quadratic function may be performed by determining a symmetry axis of the quadratic function, determining a fitting region and fitting the quadratic function to the data set in the fitting region.

The symmetry axis of the quadratic function may be determined based on the end cycle of the signal-generating reaction. The quadratic function is a function expressed as $y=a(x-b)^2+c$. b is the symmetry axis of the quadratic function. According to an embodiment, the symmetry axis of the quadratic function is determined in a range of the end cycle±10, end cycle±8, end cycle±6, end cycle±5, end cycle±3, end cycle±2 or end cycle±1.

The fitting region by the quadratic function may be determined in various manners.

Firstly, the fitting region may be determined in a region spanning from a predetermined starting fitting cycle (SFC) to a minimum fitting cycle (MFC). The starting fitting cycle may be cycle 0, cycle 1, cycle 2, cycle 3, cycle 4, cycle 5, cycle 6, cycle 7, cycle 8, or cycle 9. The minimum fitting cycle may be cycle 7, cycle 8, cycle 9, cycle 10, cycle 11, cycle 12, cycle 13, cycle 14, cycle 15, cycle 16, cycle 17, cycle 18, cycle 19, cycle 20, or cycle 21.

Alternatively, the fitting region may be determined using a quadratic function may be used. A quadratic function used to determine the fitting region is named herein a first quadratic function and a quadratic function used to amend the data set is named herein a second quadratic function. The first quadratic function is fitted to the data set in the entire region and the second quadratic function is fitted to the data set in the fitting region. The first quadratic function does not have a symmetry axis; however the second quadratic function has a symmetry axis. The end cycle of the fitting region is determined based on (i) a cycle ($C_{min}$) at which the first quadratic function exhibits the minimum value and/or (ii) a minimum fitting cycle. For example, the end cycle of the fitting region is determined as a higher cycle among (i) $C_{min}$ minus N [N is 0 or a positive integer (specifically, an integer of 1-5)] and (ii) the minimum fitting cycle (MFC).

Within the fitting region determined above, the data set or normalized data set is fitted with the quadratic function with the symmetry axis and then baseline-subtracted by the quadratic function with the symmetry axis.

(B-2) Negative Control Subtraction

The noise in the data set may be removed by subtracting a negative control from the data set. The negative control is an experimental group in which one or more essential components for the progress of reactions in the reactants for the signal-generating reaction are not present. For example, in the nucleic acid amplification reaction, the negative control is an experimental group without a target analyte, a primer or a polymerase. The negative control may include only a buffer. Specifically, the negative control used in the present invention is an experimental group in which there are components for amplifying a nucleic acid except for a target nucleic acid molecule in a nucleic acid amplification reaction.

The subtraction of the negative control may be performed by subtracting the signal value of the negative control from the signal value of the data set for the target analyte. Specifically, the signal value of the data set for the target analyte and the signal value of the negative control are obtained in the same reaction and measurement environment, for example, in the same reaction run in one same amplification and analysis apparatus.

Generation of a Non-Linear Function to the Amended Data Set (Step 330)

A non-linear function to the amended data set is generated as a fitting function. This step may be performed according to non-linear regression methods. Various conventional non-linear regression analytical methods may be used (see Seber, G. A. F., Wild, C. J. (1989) Nonlinear Regression, New York: John Wiley and Sons). For example, a polynomial function, an exponential function, a logarithmic function, a trigonometric function or a sigmoid function may be used as a non-linear function.

According to an embodiment of the present invention, the non-linear function used in the present invention is a sigmoid function. As used herein, the term "sigmoid function" refers to a function capable of representing a sigmoid curve such as a logistic function, a Gompertz function and a Chapman function.

A non-linear function fitted to the amended data set is generated. Generating the non-linear function may mean determining a non-linear function that best matches (or best represents) the amended data set. This step is basically performed by a non-linear regression method.

In one embodiment of the invention, the non-linear function may be a four-parametric sigmoid function represented by Equation III.

$$f(x) = a_1 + \frac{a_2 - a_1}{1 + 10^{a_4(a_3 - x)}} \quad \text{Equation III}$$

where f(x) represents a sigmoid function as a fit function; x represents a cycle number of the signal-generating reaction; and each of a1, a2, a3, and a4 independently represents a parameter of the sigmoid function.

According to an embodiment, a1 in Equation III represents a background signal value; a2−a1 represents difference between a maximal signal value and the background signal value; a3 represents a parameter determining the x value of an inflection point of the sigmoid function; a4 represents a parameter determining the sharpness of the sigmoid function; and a3 and a4 collectively determines the shape of the sigmoid function.

The generation of the sigmoid function may refer to a process for determining a1, a2, a3 and a4 by an iterative calculation.

The generation of the non-linear function may be performed after or before the amendment of the data set. Particularly, the generation of the non-linear function is performed after the amendment of the data set.

Determining the Fitting Accuracy of a Non-Linear Function (Step 340)

Following the generation of the non-linear function, the fitting accuracy of the non-linear function to the amended data set is determined.

The term "fitting accuracy" used herein includes (a) how close the non-linear function is to actual measurements (the data set or the amended data set), i.e., the goodness of fit and (b) how useful an explanatory variable predicts a response variable.

The goodness of the fitting may be represented by $x^2$ value (chi square value) and the predictive usefulness value may be represented by $R^2$ value. According to an embodiment, the fitting accuracy is $x^2$ value or $R^2$ value of the non-linear function to the amended data set. More particularly, the fitting accuracy is $R^2$ value.

The $R^2$ value may be calculated using Equation IV. Equation IV may be applied to the entire cycles.

$$R^2 = 1 - \frac{\sum_{i=1}^{L}(y_i - f_i)^2}{\sum_{i=1}^{n}(y_i - y_m)^2} \frac{n}{L} \qquad \text{Equation IV}$$

$y_i$: Signal value at each cycle of the data set
$f_i$: Function value at each cycle of the sigmoid function
$y_m$: Average value of signal values of the data set
L: End cycle in a fitting region
n: Number of total cycles Equation IV represents a variance of error to a total variance of the data set. The error is the difference between the data set and the sigmoid function. In Equation IV, the data set may be a normalized data set or a normalized and baselined data set.

Determining the Presence or Absence of a Target Analyte Using a Fitting Accuracy (Step 350)

The fitting accuracy of the non-linear function to the amended data set is used to determine the presence or absence of the target analyte in the sample.

One of the features of the present invention is to use the fitting accuracy of the non-linear function as a direct indicator of the presence or absence of the target analyte. The presence or absence of the target analyte in samples is determined by using (particularly, directly using) the fitting accuracy of the non-linear function, which means that the fitting accuracy is used solely or together with other criteria (particularly, parameters associated with the non-linear fitting function) for determining the presence or absence of the target analyte, particularly with no use of $C_t$ values.

Although there are prior arts that disclose application of a sigmoid function to nucleic acid amplification curves, none of prior arts teach or suggest the fitting accuracy of the sigmoid function as a direct indicator to determine the presence or absence of target analytes.

For example, US 2009/0119020 as described above uses $R^2$ values of a sigmoid function to determine whether a data set represents significant or valid growth. According to teachings of US 2009/0119020, only the absence of a target analyte may be determined by using $R^2$ values of a fitting function. In order to determine that a target analyte is present, additional step of obtaining $C_t$ values would be needed in US 2009/0119020. The present invention may directly utilize the fitting accuracy (e.g., $R^2$ value) of the non-linear function to determine the presence or absence of the target analyte in samples even with no help of $C_t$ values.

Furthermore, it is noteworthy that US 2009/0119020 teaches that if $R^2$ values exceed a significance threshold (e.g. 0.90-0.99), a data set is considered to not represent significant or valid growth, i.e., to represent the absence of a target analyte in samples. Such approach is contrary to an embodiment of the present invention as described below in which the target analyte is determined to be present when the fitting accuracy (e.g., $R^2$ value) exceeds a threshold value (e.g., 0.90-0.99).

According to an embodiment, the step of determining the presence or absence of the target analyte is performed by comparing the fitting accuracy with a threshold value for the fitting accuracy. More particularly, the step of determining the presence or absence of the target analyte is performed by evaluating whether the fitting accuracy exceeds the threshold value. When the fitting accuracy exceeds the threshold value, the target analyte may be determined to be present in samples. When the fitting accuracy is less than the threshold value, the target analyte sample may be determined to be absent in samples.

When using the $R^2$ value as the fitting accuracy, the threshold value may be 0.80, 0.85, 0.90, 0.91, 0.92, 0.93, 0.94, 0.95, 0.96, 0.97, 0.98 or 0.99.

The presence or absence of the target analyte may be determined by using only the fitting accuracy of the non-linear function. Alternatively, the presence or absence of the target analyte may be determined by using not only the fitting accuracy but also additional criteria (particularly, parameters associated with the non-linear fitting function), particularly with no use of $C_t$ values.

According to an embodiment, the determination of the presence or absence of the target analyte in the sample is performed by additionally using at least one parameter selected from the group consisting of (i) a displacement of the data set, the amended data set or the non-linear function and (ii) a maximum slope of the non-linear function.

According to an embodiment, the determination of the presence or absence of the target analyte in the sample is performed by additionally using at least one parameter selected from the group consisting of (i) a displacement of the data set, the amended data set or the four-parametric sigmoid function and (ii) a maximum slope and a4 of the four-parametric sigmoid function.

The additional considerations are particularly useful in determination of the absence of the target analyte in the sample.

Although the fitting accuracy of the non-linear function serves a sole indicator to determine the presence or absence of the target analyte, the additional considerations may be used to more effectively filter out negative samples not containing target analytes. Furthermore, signal values for negative samples theoretically exhibit a low fitting accuracy; however, sometimes it has a high fitting accuracy. Therefore, such negative samples likely to cause false positive results are needed to be filter out.

The displacement of the data set, the amended data set or the non-linear function is useful in determining the absence of the target analyte in the sample.

As used herein the term "displacement" may refer to a degree of signal change in a data set, particularly, a degree of signal change from a reference signal value. The reference signal value may include the smallest signal value, the signal value at the first cycle, the average signal value of a baseline region, or the signal value at the start of an amplification region. In calculating the displacement, the highest signal value may include the highest signal value, the signal value at the last cycle and the average signal value of a plateau region.

Determining the presence or absence of the target analyte by considering or using the displacement may be performed in various manners. For example, when the displacement of the data set is lower than a threshold value for the displacement, the data set may be determined to be negative.

When the signal-generating reaction is an amplification reaction, the threshold value for displacement may be RFU (relative fluorescence unit) 70, 80, 90, 100, 110, 120, 130, 140 or 150.

Another consideration factor is a maximum slope of the non-linear function.

An amplification curve for positive samples includes an amplification region in which a signal value increases sharply, and an amplification curve for negative samples has no amplification region in which a signal value increases sharply. Therefore, the positivity and negativity of the target analyte for the sample may be determined by considering the maximum slope of the non-linear function.

According to an embodiment, the method includes generating a maximum slope of the non-linear function; and comparing the maximum slope with a threshold value to determine that the target analyte is absent in the sample.

There are many ways to calculate the maximum slope of the non-linear function. For example, a non-linear function may be differentiated and the maximum value of the differentiated non-linear function may be determined as the maximum slope.

The threshold value for the maximum slope may be set in various manners. For example, the threshold value may be set based on results of analyzing a plurality of samples. For example, after the maximum slope of the non-linear function in a plurality of predetermined positive or negative samples is analyzed, a suitable threshold value may be selected. For example, the threshold value for the maximum slope is 10-50, 20-50, 30-50, 10-40, 20-40 or 30-40, in particular 20-40.

When the maximum slope of the non-linear function exceeds the threshold value, the target analyte may be determined to be present in the sample. When the maximum slope is less than the threshold value, the target analyte may be determined to be absent in the sample.

Another additional consideration factor is a parameter representing the shape of the non-linear function.

In an embodiment of the present invention, the parameter representing the shape of the non-linear function is used to determine whether the target nucleic acid sequence is present or absent in the sample. Specifically, a4 of the four-parametric sigmoid function of Equation III is used.

When a4 is used in determination of the presence or absence of the target analyte in the sample, a threshold value for a4 may be set as 0.07, 0.08 or 0.09. When a4 exceeds the threshold value, the data set is determined to be an abnormal signal and the target analyte is determined to be absent in the sample.

According to an embodiment of the present invention, the method further comprises obtaining a $C_t$ value by applying a signal threshold to the non-linear fitting function. Although the present invention enables to determine the presence or absence of the target analyte in the sample with no use of a signal threshold (i.e., $C_t$ values), $C_t$ values may be required by experimenters. For example, when the quantification information of target analytes is needed, $C_t$ values are generally required. Furthermore, $C_t$ values may be also used together with the fitting accuracy of the non-linear fitting function in determination of the presence or absence of the target analyte in the sample in order to increase the analysis reliability of the present method. For example, only when not only the fitting accuracy of the non-linear fitting function exceeds the threshold for the fitting accuracy but also a $C_t$ value exceeds a threshold for $C_t$ values, the target analyte is determined to be present in the sample.

II. Device and Computer Readable Storage Medium for Analyzing Target Analytes in Sample Using a Non-Linear Function In another aspect of present invention, there is provided an analysis device a target analyte in a sample, comprising:
memory; and
processor;
wherein the memory stores a data set for the target analyte, the data set is obtained from a signal-generating reaction using a signal-generating means and includes a plurality of data points including cycle numbers and signal values, and
wherein the processor amends the data set, generates a non-linear function to the amended data set, determines a fitting accuracy of the non-linear function to the amended data set and determines the presence or absence of the target analyte in the sample using the fitting accuracy.

In still another aspect of present invention, there is provided a non-transitory computer readable storage medium containing instructions to configure a processor to perform a method for analyzing a target analyte in a sample, comprising:
obtaining a data set for the target analyte; wherein the data set is obtained from a signal-generating reaction using a signal-generating means and comprises a plurality of data points including cycle numbers and signal values,
amending the data set;
generating a non-linear function to the amended data set;
determining a fitting accuracy of the non-linear function to the amended data set; and
determining the presence or absence of the target analyte in the sample using the fitting accuracy.

Since the storage medium, the device and the computer program of the prevent invention described herein below are intended to perform the present methods in a computer, the common descriptions between them are omitted in order to avoid undue redundancy leading to the complexity of this specification.

The program instructions are operative, when performed by the processor, to cause the processor to perform the present method described above. The program instructions for performing the present method may comprise (i) an instruction to amend the data set; (ii) an instruction to generate a non-linear function to the amended data set; and (iii) an instruction to determine a fitting accuracy of the non-linear function to the amended data set; (iv) an instruction to determine the presence or absence of the target analyte in the sample using the fitting accuracy.

The present method described above is implemented in a processor, such as a processor in a stand-alone computer, a network attached computer or a data acquisition device such as a real-time PC machine.

The types of the computer readable storage medium include various storage medium such as CD-R, CD-ROM, DVD, flash memory, floppy disk, hard drive, portable HDD, USB, magnetic tape, MINIDISC, nonvolatile memory card, EEPROM, optical disk, optical storage medium, RAM, ROM, system memory and web server.

The data set may be received through several mechanisms. For example, the data set may be acquired by a processor resident in a PCR data acquiring device. The data set may be provided to the processor in real time as the data set are being collected, or it may be stored in a memory unit or buffer and provided to the processor after the experiment has been completed. Similarly, the data set may be provided to a separate system such as a desktop computer system via a network connection (e.g., LAN, VPN, intranet and Internet) or direct connection (e.g., USB or other direct wired or wireless connection) to the acquiring device, or provided on a portable medium such as a CD, DVD, floppy disk, portable HDD or the like to a stand-alone computer system. Similarly, the data set may be provided to a server system via a network connection (e.g., LAN, VPN, intranet, Internet and wireless communication network) to a client such as a notebook or a desktop computer system.

The instructions to configure the processor to perform the present invention may be included in a logic system. The instructions may be downloaded and stored in a memory module (e.g., hard drive or other memory such as a local or attached RAM or ROM), although the instructions may be provided on any software storage medium such as a portable HDD, USB, floppy disk, CD and DVD. A computer code for implementing the present invention may be implemented in a variety of coding languages such as C, C++, Java, Visual Basic, VBScript, JavaScript, Perl and XML. In addition, a variety of languages and protocols may be used in external and internal storage and transmission of data and commands according to the present invention.

According to an embodiment, the device further comprises a reaction vessel to accommodate the sample and signal-generating means, a temperature controlling means to control temperatures of the reaction vessel and/or a detector to detect signals at cycle numbers.

The processor may be prepared in such a manner that a single processor may do several performances. Alternatively, the processor unit may be prepared in such a manner that several processors do the several performances, respectively. According to an embodiment, the processor may be embodied by installing software into conventional devices for detection of target nucleic acid sequences (e.g. real-time PCR device).

III. Methods for Analyzing Target Analytes in Sample Using a Quadratic Function In still another aspect of present invention, there is provided a method for analyzing a target analyte in a sample, comprising:

obtaining a data set for the target analyte; wherein the data set is obtained from a signal-generating reaction using a signal-generating means and comprises a plurality of data points including cycle numbers and signal values, generating a quadratic function fitted to the data set in a fitting region of a baseline region of the data set; and amending the data set by subtracting the quadratic function from the data set.

The common descriptions between the first aspect and third aspect of the present invention are omitted in order to avoid undue redundancy leading to the complexity of this specification.

The present inventors have made intensive researches to overcome the problems and disadvantages of conventional methods, particularly problems associated with setting of a threshold value for obtaining a $C_t$ value in a nucleic acid amplification reaction. As a result, the present inventors have found that various parameters of a fitting function for a data set obtained from a signal-generating reaction, specifically a cycle ($C_{min}$) at which a fitting quadratic function is minimum, the coefficient of $x^2$ or a fitting accuracy may be an indicator for determining the presence or absence of target analytes. Also, the present inventors have tried to improve conventional baselining methods and have finally found to efficiently and easily perform a baselining by using a quadratic function fitted to a data set in a fitting region.

Although the method is expressed as a method for analyzing a target analyte, it may be also expressed as a method for baselining a data set for a target analyte.

Obtaining a Data Set for the Target Analyte

This step can be described with reference to descriptions for the first aspect of the present invention.

Generating a Quadratic Function Fitted to the Data Set

A quadratic function to the data set as a fitting function is generated in a fitting region of a baseline region of the data set. Various conventional non-linear regression analytical methods for fitting may be used in the present invention (see Seber, G. A. F., Wild, C. J. (1989) Nonlinear Regression, New York: John Wiley and Sons).

The descriptions for this step can be made with reference to the descriptions for the baselining using a quadratic function having a symmetry axis discussed above.

The data set including a pre-amended data set and post-amended may be fitted with the quadratic function.

According to an embodiment, the quadratic function has a symmetric axis. According to an embodiment, the symmetry axis of the quadratic function is determined based on the end cycle of the signal-generating reaction. More particularly, the symmetry axis of the quadratic function is determined in a range of the end cycle±10, end cycle±8, end cycle±6, end cycle±5, end cycle±3, end cycle±2 or end cycle±1.

The generation of the quadratic function may be performed by determining a symmetry axis of the quadratic function, determining a fitting region and fitting the quadratic function to the data set in the fitting region. The quadratic function is a function expressed as $y=a(x-b)^2+c$ (a is coefficient of $x^2$, b is the symmetry axis and c is y-axis intercept).

The fitting region may be determined within a baseline region of the data set. The fitting region may be determined in various manners.

Firstly, the fitting region may be predetermined. According to an embodiment, the fitting region spans from a starting fitting cycle (SFC) to a minimum fitting cycle (MFC).

According to an embodiment, when a displacement of the data set exceeds a threshold for the displacement, the fitting region spans from the starting fitting cycle (SFC) to the minimum fitting cycle (MFC). More specifically, when the difference between the maximum value and the minimum value of the data set is larger than a predetermined threshold value (for example, RFU 100, 200, 300 or 400), or when the difference between the final value and the initial value of the data set exceeds a predetermined threshold value (for example, RFU 0), the fitting region is determined in a region spanning from the starting fitting cycle (SFC) to the minimum fitting cycle (MFC).

The starting fitting cycle may be cycle 0, cycle 1, cycle 2, cycle 3, cycle 4, cycle 5, cycle 6, cycle 7, cycle 8, or cycle 9. The minimum fitting cycle may be cycle 7, cycle 8, cycle 9, cycle 10, cycle 11, cycle 12, cycle 13, cycle 14, cycle 15, cycle 16, cycle 17, cycle 18, cycle 19, cycle 20, or cycle 21.

According to an embodiment of the present invention, the fitting region may be 1-20 cycles, 2-20 cycles, 3-20 cycles, 4-20 cycles, 5-20 cycles, 6-20 cycles, 1-18 cycles, 2-18 cycles, 3-18 cycles, 4-18 cycles, 5-18 cycles, 6-18 cycles, 1-16 cycles, 2-16 cycles, 3-16 cycles, 4-16 cycles, 5-16 cycles, 6-16 cycles, 1-14 cycles, 2-14 cycles, 3-14 cycles, 4-14 cycles, 5-14 cycles, 1-12 cycles, 2-12 cycles, 3-12 cycles, or 4-12 cycles.

Secondly, the fitting region may be determined using a quadratic function may be used. A quadratic function used to determine the fitting region is named herein a first quadratic function and a quadratic function used to amend the data set is named herein a second quadratic function.

According to an embodiment, the present method, before generating quadratic function in the fitting region, further comprises generating a first quadratic function fitted to the data set in an entire region; and the fitting region (particularly, the end cycle of the fitting region) is determined based on a cycle ($C_{min}$) at which the first quadratic function has a minimum signal value.

The first quadratic function does not have a symmetry axis; however the second quadratic function has a symmetry axis. The end cycle of the fitting region may be determined based on (i) a cycle ($C_{min}$) at which the first quadratic function exhibits the minimum value and/or (ii) a minimum fitting cycle. For example, the end cycle of the fitting region is determined as a higher cycle among (i) $C_{min}$ minus N [N is 0 or a positive integer (specifically, an integer of 1-5)] and (ii) the minimum fitting cycle (MFC).

Amending the Data Set by Subtracting the Quadratic Function from the Data Set

The data set is amended by subtracting the quadratic function from the data set.

According to an embodiment, the method further comprises determining a fitting accuracy of the quadratic function to the amended data set; and determining the presence or absence of the target analyte in the sample using the fitting accuracy.

The fitting accuracy for the quadratic function may be determined in the fitting region. The fitting accuracy between the data set and the quadratic function is determined using the signal values in the fitting region. According to an embodiment of the present invention, the fitting accuracy is the $x^2$ (a chi square value) or the $R^2$ value for the data set and the quadratic function, more specifically, the $R^2$ value.

The $R^2$ value may be calculated using Equation V.

$$R^2 = 1 - \frac{\sum_{i=s}^{L}(y_i - f_i)^2}{\sum_{i=1}^{n}(y_i - y_m)^2} \frac{n}{L-s}$$ Equation V Equation V represents a variance of an error in the fitting region versus a total variance of the data set. The error is a difference between the data set and the quadratic function.

$y_i$ is the signal value at each cycle of the data set.
$f_i$ is the value of the quadratic function.
$y_m$ is the average value of the data set.
L is the end cycle of the fitting region.
S is the start cycle of the fitting region.
L-S is the length of the fitting region.
n is the number of total cycles.

One of the characteristics of the present invention is that the fitting accuracy of the quadratic function is used as a direct indicator in the analysis of the target analyte, particularly the presence or absence of the target analyte, particularly the absence. To our best knowledge, there is no prior art in which the fitting accuracy of the quadratic function in a fitting region is used as a direct indicator for determining whether the target analyte is absent.

According to an embodiment of the present invention, the step of determining the presence or absence of the target analyte in the sample determines that the target analyte in the sample is absent when the fitting accuracy is less than the threshold value.

As described above, since the fitting accuracy may be used as the direct indicator for determining the presence or absence of the target analyte, particularly the absence, the absence of the target analyte may be easily determined by comparing the threshold value with the fitting accuracy.

The threshold value for the fitting accuracy in the fitting region may be a threshold value commonly used in the art. For example, when using the $R^2$ value as the fitting accuracy, the threshold value may be 0.80, 0.85, 0.90, 0.91, 0.92, 0.93, 0.94, 0.95, 0.96 or 0.97.

In addition, the presence or absence of the target analyte in the sample may be determined based on (i) the cycle ($C_{min}$) at which the first quadratic function has a minimum signal value and/or (ii) $x^2$ coefficient of the first quadratic function.

According to an embodiment of the present invention, the determination is a determination of the absence of the target analyte in the sample.

According to an embodiment of the present invention, the step of determining the absence of the target analyte is performed by comparing the $C_{min}$ with the threshold value. If the $C_{min}$ exceeds the threshold value, the target analyte in the sample is determined to be absent.

One of the characteristics of the present invention is that the $C_{min}$ is used as a direct indicator for determining whether the target analyte is absent. Although there are prior arts that apply a fitting function to the nucleic acid amplification curve, there is no publication in which the $C_{min}$ is used as a direct indicator for determining whether the target analyte is absent.

As described above, since the $C_{min}$ may be used as the direct indicator for determining the absence of the target analyte, the absence of the target analyte may be easily determined by comparing the threshold value with the $C_{min}$.

The threshold value is, for example, cycle 27, 28, 29, 30, 31, 32, 33, 34, 35, 36, 37, 38, 39 or 40.

Alternatively, the step of determining the presence or absence of the target analyte in the sample is performed by determining whether the target analyte in the sample is absent by evaluating $x^2$ coefficient of of the first quadratic function to be less than zero. To our best knowledge, data sets with $x^2$ coefficient of the first quadratic function less than zero would all be considered as negative.

As described above, the $C_{min}$ and $x^2$ coefficient of the first quadratic function and the fitting accuracy for the second quadratic function may be used as the indicator to determine the absence of the target analyte in the sample.

IV. Combination of the Present Invention with MuDT Technology

The present Applicant had developed the MuDT technology published under WO 2015/147412 in which a plurality of target nucleic acid sequences are detected using a single type of detector in a single reaction vessel. In the MuDT technology, the presence of a target nucleic acid having a relatively low detection temperature is determined by (i) signals detected at both a relatively high detection temperature and the relatively low detection temperature and (ii) a reference value representing a relationship of change in signals at the different detection temperatures. If a first target nucleic acid sequence is a target nucleic acid sequence having a relatively high detection temperature and a second target nucleic acid sequence is a target nucleic acid sequence having a relatively low detection temperature, the signal for the second target nucleic acid sequence is extracted from the signal detected at the relatively low detection temperature by removing the signal for the first target nucleic acid sequence using the reference value for the first target nucleic acid sequence.

The MuDT technology is remarkably improved as compared with the conventional methods in a manner of obtaining separately the signal for the first target nucleic acid sequence and the signal for the second target nucleic acid sequence, which have not been distinguished by using the conventional single type of detector. In particular, the method exhibits significant accuracy in extracting signals for target nucleic acid sequences from a sample containing both the target nucleic acid sequence having a relatively high detection temperature and a target nucleic acid sequence having a relatively low detection temperature (co-infection sample).

The present invention using the non-linear fitting function may be well combined with the MuDT technology.

According to an embodiment, the data set comprises (i) a signal for a first target nucleic acid sequence that is a signal detected at a relatively high detection temperature and/or (ii) a signal for a second target nucleic acid sequence extracted from a signal detected at a relatively low detection temperature, and wherein the first target nucleic acid sequence and the second target nucleic acid sequence are detected from a single reaction vessel.

According to an embodiment, the signal for the first target nucleic acid sequence and the signal for the second target nucleic acid sequence are obtained by the following steps:
  (a) incubating a first signal-generating means capable of generating the signal for the first target nucleic acid sequence and a second signal-generating means capable of generating the signal for the second target nucleic acid sequence in the reaction vessel with the sample and detecting signals at the relatively high detection temperature and at the relatively low detection temperature;
  wherein each of the first target nucleic acid sequence and the second target nucleic acid sequence is detected by a corresponding signal-generating means,
  wherein the first signal-generating means generates a signal at the relatively high detection temperature and the relatively low detection temperature when the first target nucleic acid sequence exists in the sample, and
  wherein the second signal-generating means generates a signal at the relatively low detection temperature when the second target nucleic acid sequence exists in the sample,
  (b) identifying whether a signal detected at the relatively low detection temperature satisfies a first criterion defined by a first threshold or a first signal displacement; wherein when the signal detected at the relatively low detection temperature satisfies the first criterion, a step (c) is further performed and wherein when the signal detected at relatively low detection temperature does not satisfy the first criterion, the first target nucleic acid sequence and the second target nucleic add sequence are determined to be absent in the sample and the step (c) is not performed; and,
  (c) extracting the signal for the second target nucleic acid sequence from the signal detected at the relatively low detection temperature using (i) a reference value for removing the signal for the first target nucleic acid sequence from the signal detected at the relatively low detection temperature and (ii) the signal detected at the relatively low detection temperature.

According to an embodiment, the signal for the second target nucleic acid sequence is provided by Equation VI:

Signal for the second target nucleic acid sequence= [the signal detected at relatively low detection temperature]−[(the signal detected at the relatively high detection temperature)×(the reference value for the first target nucleic acid sequence)]   Equation VI The term "target nucleic acid sequence having a relatively high detection temperature" as used herein refers to a target nucleic acid sequence which is capable of generating a signal at the relatively high detection temperature of the two detection temperatures, and thus generating a signal at the relatively low detection temperature as well. In contrast, the term "target nucleic acid sequence having a relatively low detection temperature" refers to a target nucleic acid sequence which is capable of generating a signal at the relatively low detection temperature of the two detection temperature, but not generating a signal at the relatively high detection temperature.

The relatively high detection temperature is a temperature capable of generating only a signal for the target nucleic acid sequence having the relatively high detection temperature, and the relatively low detection temperature is a temperature capable of generating both a signal for the target nucleic acid sequence having the relatively low detection temperature and a signal for the target nucleic acid sequence having the relatively high detection temperature. The relatively high detection temperature may be referred to a first detection temperature, and the relatively low detection temperature may be referred to a second detection temperature.

According to an embodiment, the relatively high detection temperature and the relatively low detection temperature at which the detection is carried out may be determined. For example, the relatively high detection temperature and the relatively low detection temperature are determined as 72° C. and 60° C., respectively, and then signal-generating means suitable for the detection temperatures are constructed.

According to an embodiment of this invention, when the signal-generating means generates a signal in a dependent manner on the formation of a duplex, the detection temperature is controllable by adjusting a Tm value of the duplex.

Where the signal is generated by the duplex formed dependent on the presence of the target nucleic acid sequence, the detection of the signal is successfully done at the determined temperature by adjusting the Tm value of the duplex. For example, where the signal is generated by the PTOCE method, the detection of the signal is successfully done at the determined temperature by adjusting the Tm value of the extended duplex formed by the extension of the PTO fragment on the CTO.

The reference value is a value for removing the signal for the first target nucleic acid sequence from the signal detected at the relatively low detection temperature. In one embodiment of the present invention, the reference value is a value representing a relationship of the change in the signals provided by the first signal-generating means when the first target nucleic acid sequence in the sample is present at the relatively high detection temperature and the relatively low detection temperature.

According to the present invention, the non-linear fitting function is generated to the extracted signal for the second target nucleic acid sequence.

V. Methods for Analyzing Target Analytes in Sample Using a Quadratic Function In further aspect of this invention, there is provided a device for analyzing a target analyte in a sample, comprising:

memory; and processor;

wherein the memory stores a data set for the target analyte, the data set is obtained from a signal-generating reaction using a signal-generating means and includes a plurality of data points including cycle numbers and signal values, and wherein the processor generates a quadratic function fitted to the data set in a fitting region of a baseline region of the data set and amends the data set by subtracting the quadratic function from the data set.

In still further aspect of this invention, there is provided a device for analyzing a computer readable storage medium containing instructions to configure a processor to perform a method, the method comprising:

obtaining a data set for the target analyte; wherein the data set is obtained from a signal-generating reaction using a signal-generating means and includes a plurality of data points including cycle numbers and signal values, generating a quadratic function to the data set in a fitting region of a baseline region of the data set; and amending the data set by subtracting the quadratic function from the data set.

Since the storage medium, the device and the computer program of the prevent invention are intended to perform the present methods of Section III and IV in a computer, the common descriptions between them are omitted in order to avoid undue redundancy leading to the complexity of this specification.

VI. Specific Embodiments of this Invention

Figure 1:
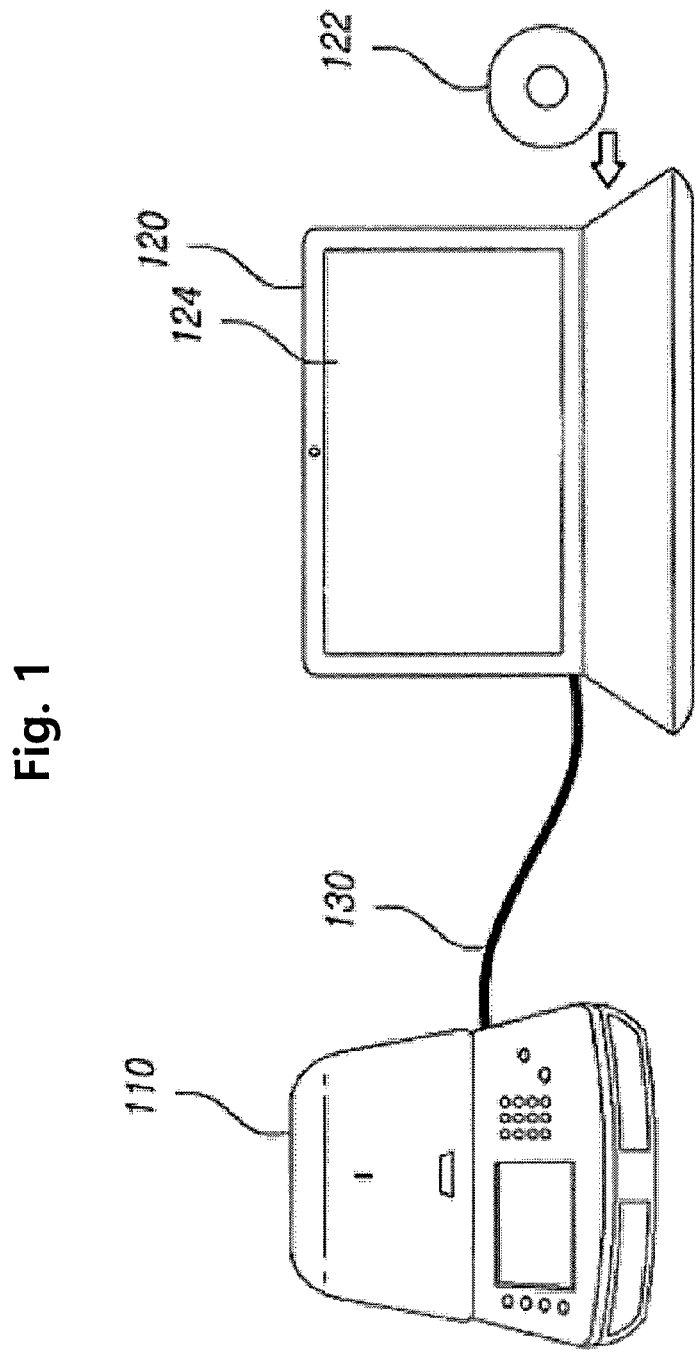
FIG. 1 represents a device for analyzing target analyte according to an embodiment.

The specific embodiments of the present invention will be described as follows:

FIG. 1 represents a device for analyzing target analyte according to an embodiment. Referring to the FIG. 1, an analysis system includes an amplification device 110 and an analysis device 120. The analysis system may determine the presence or absence of the target analyte in the sample and display a result to the user.

The amplification device 110 is a device for performing a nucleic acid amplification reaction, an enzyme reaction, or a microbial growth. For example, when the amplification device 110 performs the nucleic acid amplification reaction, the amplification device 110 may repeatedly perform an operation of increasing or decreasing a temperature of samples. The amplification device 110 may obtain a data set by measuring signals generated from the samples for each cycle.

The amplification device 110 may be connected to the analysis device 120 and a cable 130 or wirelessly. The amplification device 110 transmits the obtained data set to the analysis device 120 via wired or wireless connection.

The analysis device 120 obtains the data set from the amplification device 110. The analysis device 120 analyzes the data set to determine whether a target analyte in the sample is present or absent. In other words, the analysis device 120 determines the positive or negative for the sample.

The analysis device 120 includes a display device 124. The display device 120 may display a data set or display a floating data set as a graph. The display device 124 may display a sigmoid function, a step function, or the like. In addition, the display device 124 may display whether the target analyte is present or absent, and a detection result for each sample.

The analysis apparatus 120 may read a data set included in a storage medium 122. The storage medium 122 may store the data set, or may store programs and the like used in the analysis apparatus 120. The storage medium 122 may be a CD, a USB, or the like.

Figure 2:
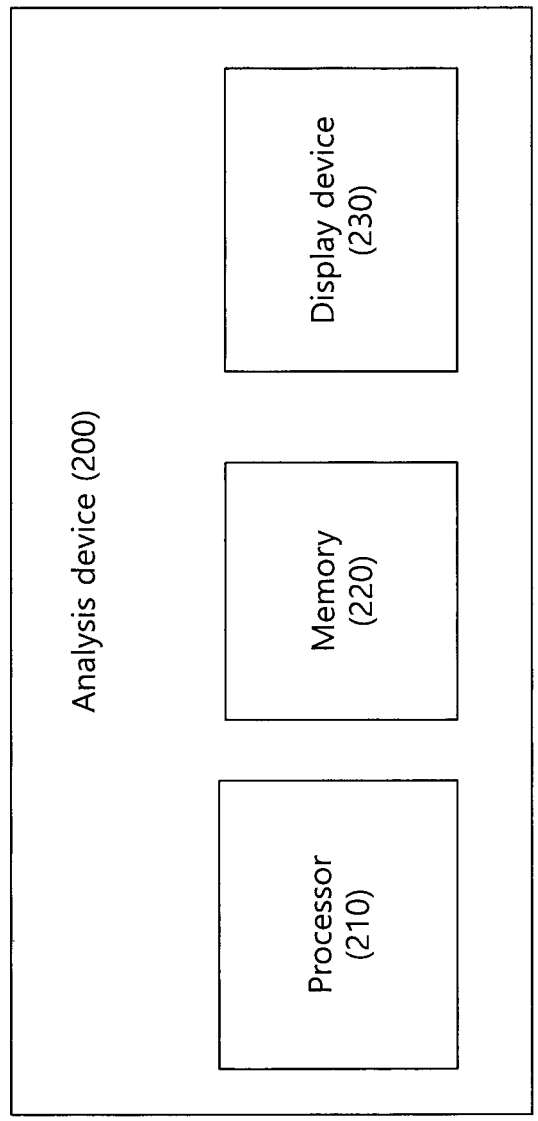
FIG. 2 is a block diagram illustrating an analysis device according to an embodiment of the present invention.

FIG. 2 is a block diagram illustrating an analysis device according to an embodiment of the present invention. Referring to the FIG. 2, the analysis device 200 includes a processor 210, a memory 220, and a display device 230.

The memory 220 stores a data set received from the amplification device 110. The memory 220 may store the processed data in the processor 210. For example, the memory 220 may store a data set, a normalized data set, a baselined data set, an amended data set, a non-linear function, a fitting accuracy, and a threshold value. In FIG. 2, the memory 220 is illustrated as being separate from the processor 210, but the memory 220 may be implemented as a single device with the processor 210. For example, the memory 220 may be storage like a cache included within the processor 210.

The processor 210 may use the data set to determine whether a target analyte in the sample is present or absent. The processor 210 may use the non-linear function to calculate a fitting accuracy of the data set using the non-linear function and determine the presence or absence of the target analyte according to the magnitude of the fitting accuracy.

Although FIG. 2 illustrates that the analysis device 200 includes a single processor 210, the analysis device 200 may include one or more processors 210.

The display device 230 may display a graph, a table, or a text by a control of the processor 210. For example, the display device 230 may display data set, non-linear functions, and the like as a graph. The display device 230 may display the information of wells as a table. The display device 230 may display a fitting accuracy, positive/negative, and the like as a text.

Figure 4:
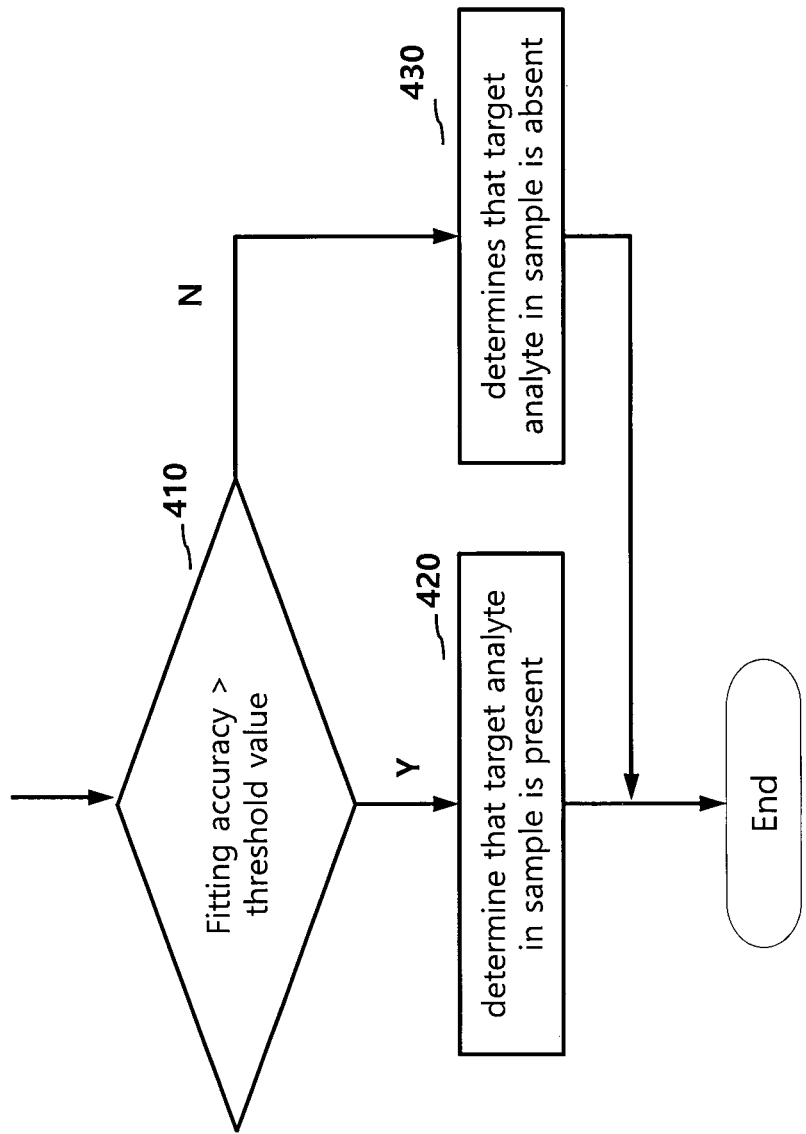
FIG. 4 is a flow chart illustrating a method for determining the presence or absence of a target analyte according to an embodiment.

FIG. 4 is a flow chart illustrating a method for determining the presence or absence of a target analyte according to an embodiment. Referring to the FIG. 4, the analysis device 200 may determine the presence or absence of the target analyte by comparing the fitting accuracy with a threshold value. The steps of FIG. 4 may be performed after the step 340 of FIG. 3. In other words, the analysis device 200 may determine the fitting accuracy in the step 340 and may compare the fitting accuracy with the threshold value in step 410. In step 410, the analysis device 200 determines whether the fitting accuracy exceeds the threshold value. If the fitting accuracy exceeds the threshold value, the processor proceeds to step 420. If the fitting accuracy does not exceed the threshold value, the processor proceeds to step 430. The threshold value may be determined using experimental data, for example, the threshold value may be set to 0.9. In step 420, the analysis device 200 determines that a target analyte in the sample is present. That the fitting accuracy exceeds the threshold value represents that the non-linear function is the same or similar to the amplification curve. The amplification curve may be a general type of the curve obtained when the target analyte in the sample is present. In other words, when the target analyte in the sample is present, since the target analyte is repeatedly replicated, an increasing type of signal such as a quadratic function or an exponential function is obtained from the sample. Thus, when the type of the data set shows an amplification curve, the non-linear function is similar to the data set and the fitting accuracy is higher. In step 430, the analysis device 200 determines that the target analyte in the sample is absent. The fitting accuracy of less than the threshold value represents that the non-linear function is deviated from the amplification curve. In other words, if the target analyte in the sample is absent, the reaction in which the target analyte is replicated does not occur. Therefore, the data set and the non-linear function are different shapes and the fitting accuracy is lower.

FIG. 5 illustrates a method for analyzing using a fitting accuracy when a target analyte in a sample is present. In FIG. 5, the amended data set 510 is represented by a dotted line and the non-linear function 520 is represented by a solid line. The amended data set 510 is represented as a dotted line because the amended data set 500 is a set of coordinate values (discontinuous data) of (cycle, signal value). The non-linear function 520 may be a sigmoid function of Equation III. Since the non-linear function 520 is a continuous function represented by a solid line.

The analysis device 200 performs a fitting between the amended data set 510 and the non-linear function 520. Fitting represents to search for a non-linear function 520 that is most similar to the amended data set 510 or to determine the parameters of the non-linear function 520. The non-linear function 520 may be generated by a least squares method. In other words, the analysis device 200 repeats the process of modifying the parameters of the non-linear function 520 to minimize an error between the non-linear function 520 and the amended data set 510. The analysis device 200 determines the parameters of the non-linear function 520 when the error between the non-linear function 520 and the amended data set 510 is minimum.

The analysis device 200 calculates the $R^2$ value of the non-linear function 520 having the determined parameters and the amended data set 510. The analysis device 200 determines the presence or absence (positive/negative) of the target analyte depending on the $R^2$ value. The $R^2$ value may be calculated using Equation IV.

Referring to FIG. 5, the $R^2$ value of the non-linear function 520 is 0.9985. A threshold value is set to 0.9. Therefore, because the $R^2$ value exceeds the threshold value, the analysis device 200 determines that the target analyte in the sample is present (positive). The analysis device 200 may display a text of presence or positive on the display device 230 according to an analysis result.

Figure 6:
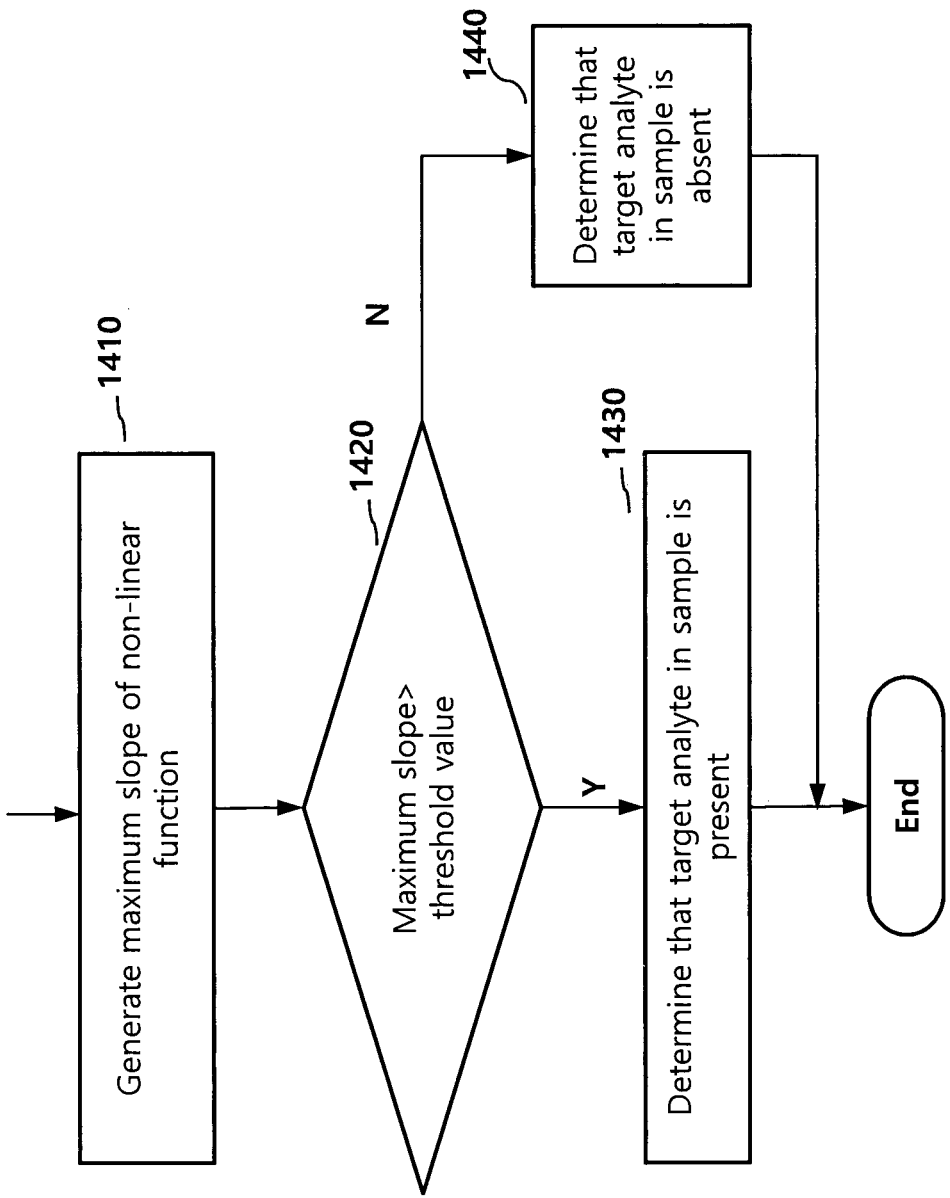
FIG. 6 is a flow chart illustrating a method for determining the presence or absence of a target analyte using a maximum slope.

FIG. 6 is a flow chart illustrating a method for determining the presence or absence of a target analyte using a maximum slope. The analysis device 200 may determine the absence of the target analyte in the sample using the maximum slope of a non-linear function. The steps of FIG. 6 may be performed after the step 350 or 330 of FIG. 3. In step 1410, the analysis device 200 generates the maximum slope of the non-linear function. The analysis device 200 may differentiate the non-linear function and determine a maximum value of the differentiated non-linear function as the maximum slope. In step 1420, the analysis device 200 determines whether the maximum slope of the non-linear function exceeds a threshold value for the maximum slope. The analysis device 200 proceeds to step 1430 if the maximum slope exceeds the threshold value and otherwise proceeds to step 1440. The threshold value may be set between 20 and 40.

In step 1430, the analysis device 200 determines that the target analyte in the sample is present. Since the maximum slope of the non-linear function exceeds the threshold value, the analysis devices 200 may determine that an amplification reaction for the target analyte occurs.

In step 1440, the analysis device 200 determines that the target analyte in the sample is absent. Since the maximum slope of the non-linear function does not exceed the threshold value, the analysis device 200 may determine that the amplification reaction for the target analyte does not occur.

Figure 7:
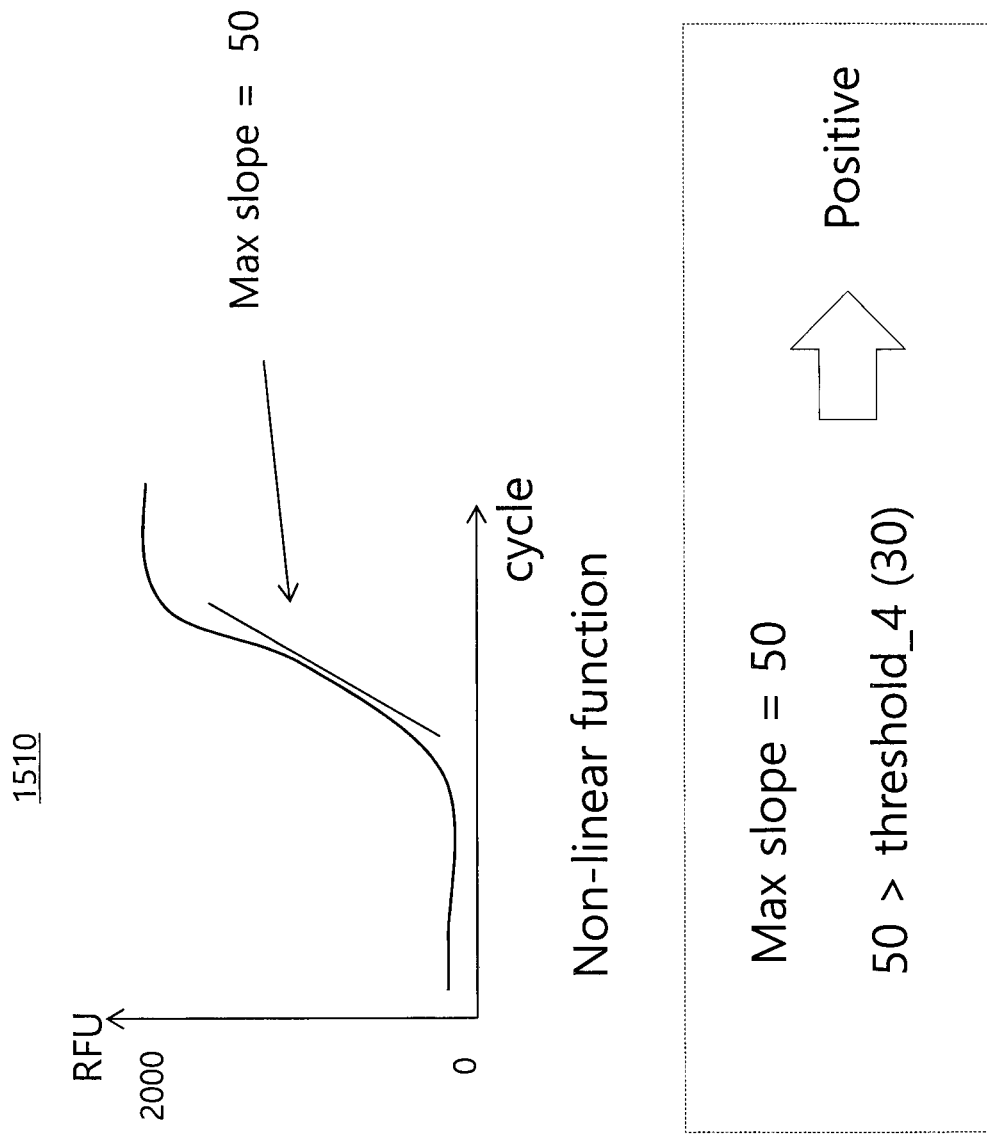
FIG. 7 illustrates a method for analyzing using a maximum slope when a target analyte in a sample is present.

FIG. 7 illustrates a method for analyzing using a maximum slope when a target analyte in a sample is present. In FIG. 7, the analysis device 200 generates the maximum slope of the non-linear function 1510. In FIG. 7, the maximum slope of the non-linear function 1510 is 50. The analysis device 200 determines whether the maximum slope exceeds the threshold value. In FIG. 7, the threshold value is set to 30, and the maximum slope (50) of the non-linear function 1510 exceeds the threshold value (30). Thus, the analysis device 200 determines that the target analyte in the sample is present (positive).

When the target analyte in the sample is present, there is a region in which the signal value increases sharply as the non-linear function 1510 of FIG. 7. The analysis device 200 may determine that the target analyte in the sample is present if there is a sharply increasing region.

Figure 8:
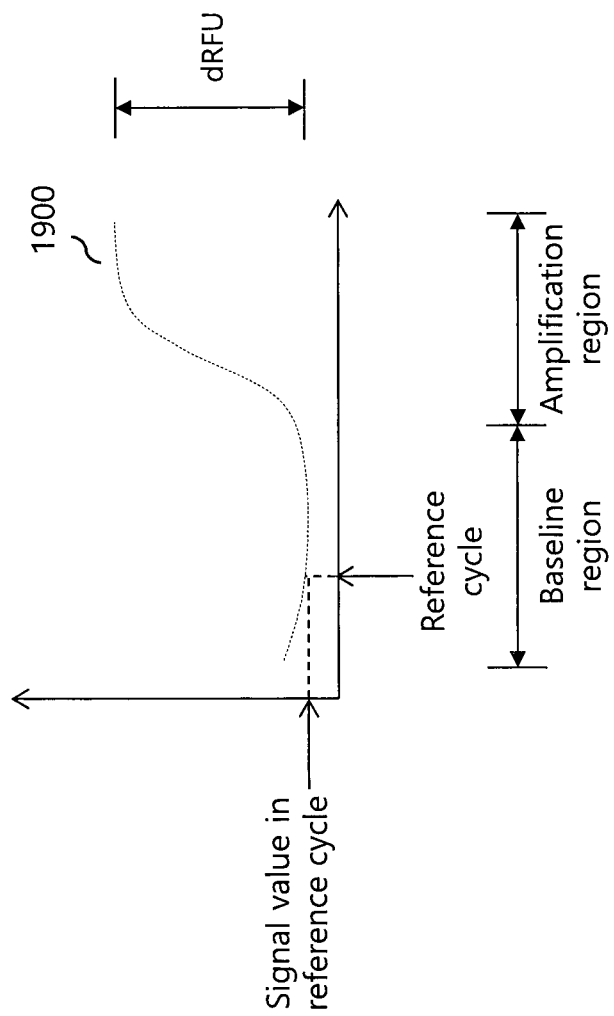
FIG. 8 illustrates a method for normalizing a data set by the SBN method.

FIG. 8 illustrates a method for normalizing a data set by the SBN method. Referring to FIG. 8, a reference cycle for the data set 1900 and a signal value at the reference cycle are determined. When the signal value at the reference cycle is determined, a normalization coefficient is generated using the signal value at the reference cycle or the modification of the signal value at the reference cycle.

When the normalization coefficient is generated using the signal value at the reference cycle, the signal value at the reference cycle may be used as the normalization coefficient. Thus, the data set 1900 is normalized by applying the signal value at the reference cycle to the signal values of the data set 1900.

When the normalization coefficient is generated by using the modification of the signal value at the reference cycle, the normalization coefficient may be determined using a relationship between the signal value at the reference cycle and the reference value. The relationship between the signal value at the reference cycle and the reference value may be a difference between the signal value at the reference cycle and the reference value. In an example, the difference between the signal value at the reference cycle and the reference value is a ratio of the signal value at the reference cycle to the reference value.

The reference cycle is arbitrarily determined, and the signal value at the reference cycle is a signal value of the data set 1900. As shown in FIG. 8, the reference cycle is determined among the cycles of the data set 1900, and is determined in the baseline region.

dRFU represents the displacement of the data set 1900. The displacement of the data set 1900 may be calculated as a difference between a maximum value and a minimum value among the signal values of the data set or a difference between a final value and an initial value.

The baseline region is a region where amplification for the target analyte is not generated, and the signal amplification region is a region where the amplification for the target analyte is generated. The reference cycle may be selected among cycles in the baseline region. In one example, the reference cycle may be cycle 4. Although FIG. 8 uses a single reference cycle, the reference cycle may be two or more cycles. When a plurality of reference cycles are selected, a plurality of signal values in the plurality of reference cycles are determined, and the plurality of signal values are used to determine a normalization coefficient.

Figure 9:
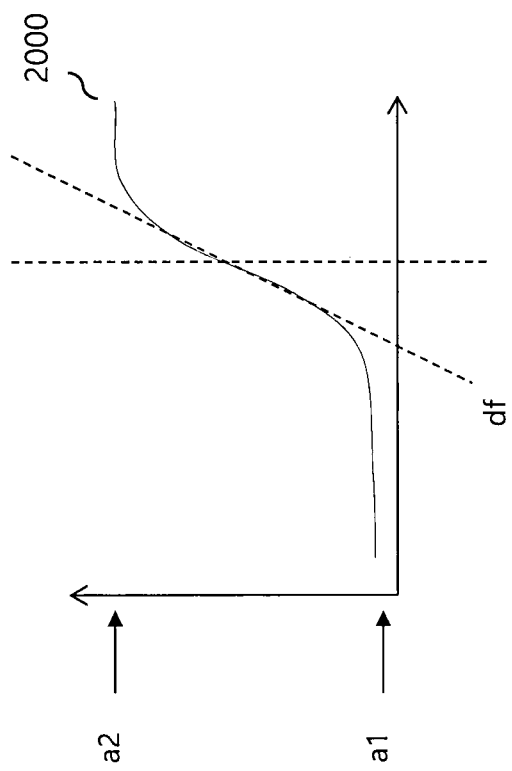
FIG. 9 illustrates properties of a non-linear function.

FIG. 9 illustrates properties for a non-linear function. The properties for a non-linear function 2000 are used to determine the presence or absence of a target analyte in the sample. Specifically, the properties for the non-linear function 2000 may be compared with a predetermined threshold value for each of the properties such that and the presence or absence of the target analyte in the sample may be determined.

Since the present invention generates the non-linear function 2000 as a continuous function, it may minimize influences caused by jump errors or noise generated in some amplification regions.

According to an embodiment of this invention, the present invention does not determine the presence or absence of the target analyte depending on whether the displacement of the non-linear function 500 exceeds a signal threshold value. Instead of using a single criteria or property of reactions, the present invention extracts a plurality of properties of the non-linear function 500 and analyzes the properties to determine the presence of target analytes in samples.

Since the prior art determines the presence or absence of target analytes based on whether a data set exceeds a signal threshold value, each signal value of the data set affects determination of the presence or absence of the target analyte. Therefore, it is very important to amend the data set including removal of the jump error or noise and to set a signal threshold value appropriately. If the amendment for the data set is not performed properly or the setting of the signal threshold value is not elaborated, there is a risk of false positives or false negatives.

Since the present invention uses a non-linear function 2000 fitted to a data set or a normalized data set, a plurality of properties for the non-linear function 2000 may be easily extracted. In other words, since the non-linear function 2000 as represented by an equation is a continuous function, it is easy to accurately extract a plurality of properties of the non-linear function 2000 useful in determination of the presence or absence of target analytes including a displacement, a maximum slope and parameters of the non-linear function 2000.

The non-linear function 2000 is a function fitted to the normalized data set. The equation shown in FIG. 9 is an example of the non-linear function 2000 and is a form of a sigmoid function. The sigmoid function shown in FIG. 9 includes four parameters a1, a2, a3, and a4. The sigmoid function may include five or more parameters or may include three or less parameters.

The properties of the non-linear function 2000 include the parameters a1, a2, a3, a4, the displacement (dRFU), the maximum slope (df) and $R^2$. The maximum slope may be expressed as FDM (First Derivative Maximum).

The displacement of the non-linear function 2000 may be a difference between a maximum value and a minimum value of the non-linear function 2000 or a difference between an initial value and a final value. In one example, the displacement of the non-linear function 2000 may be calculated as a2 minus a1. The displacement of the non-linear function 2000 may be compared to a threshold value for the displacement. For example, the threshold value for the displacement is 70, 80, 90, 100, 110, 120, 130 or 140. A unit of the threshold value for the displacement may be RFU. If the displacement of the non-linear function 2000 is less than the threshold value for the displacement, the target analyte in the sample is determined to be absent.

Parameter a3 is an inflection point of the non-linear function 2000. df is the maximum slope of the non-linear function 2000. df may be the slope at a3. The maximum slope of the non-linear function 2000 may be compared with a threshold value for the maximum slope. For example, the threshold value for the maximum slope is 20, 21, 22, 23, 24, 25, 26, 27, 28, 29, 30, 31 or 32. If the maximum slope of the non-linear function 2000 is less than the threshold value for the maximum slope, the target analyte in the sample is determined to be absent.

In an embodiment of the present invention, a quadratic function may be used to determine the presence or absence of the target analyte in the sample.

The quadratic function for the data set is generated. The quadratic function is generated using a fitting with the data set in the entire region (whole cycle). The quadratic function fitted in the entire region may be denoted by a first quadratic function. Various conventional non-linear regression analytical methods for fitting may be used in the present invention (see Seber, G. A. F., Wild, C. J. (1989) Nonlinear Regression, New York: John Wiley and Sons). The first quadratic function is a function of the form $y=ax^2+bx+c$.

The presence or absence of the target analyte in the sample is determined based on the $C_{min}$ or $x^2$ coefficient of the first quadratic function.

In an embodiment of the invention, the quadratic function may be used to determine the presence or absence of the target analyte in the sample. The quadratic function for the data set is generated in the fitting region determined based on a cycle of the baseline region of the data set. The quadratic function is a fitted function with the data set in the fitting region. The quadratic function fitted in the entire region is denoted by the first quadratic function and the quadratic function fitted in the fitting region may be denoted by the second quadratic function. The fitting accuracy for the second quadratic function is determined in the fitting region. The presence or absence of the target analyte in the sample is determined using the fitting accuracy.

Figure 10:
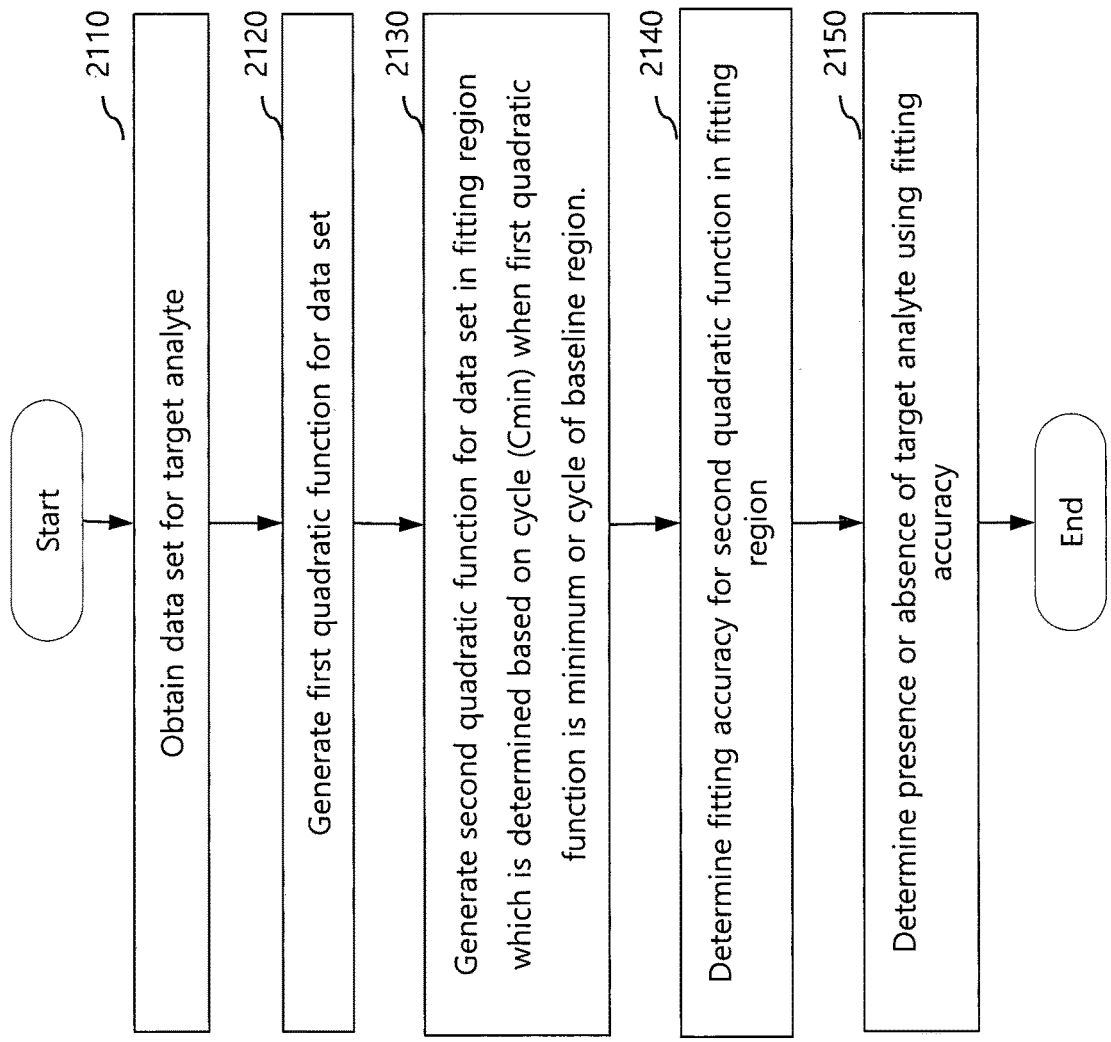
FIG. 10 is a flow chart according to an embodiment of the present invention using the quadratic function.

FIG. 10 is a flow chart according to an embodiment of the present invention using the quadratic function.

In step 2110, a data set for a target analyte is obtained. This step may be explained with reference to the described in the above method. In step 2120, a first quadratic function for the data set is generated. The first quadratic function is generated using the fitting with the data set in the entire region (whole cycle). Various conventional non-linear regression analytical methods for fitting may be used in the present invention (see Seber, G. A. F., Wild, C. J. (1989) Nonlinear Regression, New York: John Wiley and Sons). The first quadratic function is a function of the form $y=ax^2+bx+c$.

In step 2130, a second quadratic function for the data set is generated in the fitting region. The fitting region is determined based on the $C_{min}$ or a cycle of the baseline region.

The term used herein "determination based on the cycle of the baseline region" in reference to the fitting region means that all or some cycles of the baseline region are selected and used as a fitting region.

The cycles of the baseline region as the fitting region may be selected among all or some cycles of the baseline region determined by conventional methods (e.g., U.S. Pat. No. 8,560,247 and WO 2016/052991) or experientially determined.

The first quadratic function is generated. Only when the $C_{min}$ exceeds the threshold value or the coefficient of $x^2$ exceeds zero, a second quadratic function is then generated in the fitting region. The fitting region may be determined based on the cycle of the baseline region of the data set. Alternatively, the fitting region is determined based on the $C_{min}$. The term "determination based on the $C_{min}$" used in reference to the fitting region means that the end cycle of the fitting region is determined based on the or a cycle around the $C_{min}$ (particularly a cycle within $C_{min}\pm 5$ cycles). The fitting region may be determined from the above-described starting fitting cycle to the end cycle, and the end cycle may be determined as a cycle determined based on the $C_{min}$.

The second quadratic function includes various functions such as a linear function, a polynomial function (e.g., a quadratic function and a cubic function), and an exponential function. The second quadratic function that best matches the data set is determined by using a linear or non-linear regression method.

According to an embodiment of the present invention, an exponential function may be used instead of the second quadratic function. The second quadratic function is a function of the form $y=a(x-b)^2+c$. The exponential function is a function of the form $y=d(e^{a(b-x)})+c$. b is the symmetry axis of the second quadratic function or exponential function.

An exponential function fitted to the signal values in the baseline region of the data set is generated and an amended data set is generated by subtracting the exponential function from the data set.

In step 2140, the fitting accuracy for the second quadratic function is determined in the fitting region. The fitting accuracy between the data set and the second quadratic function is determined using the signal values in the fitting region.

One of the characteristics of the present invention is that the fitting accuracy of the second quadratic function is used as a direct indicator in the analysis of the target analyte. In step 2150, the fitting accuracy is used to determine the presence or absence of target analyte in the sample.

Figure 11:
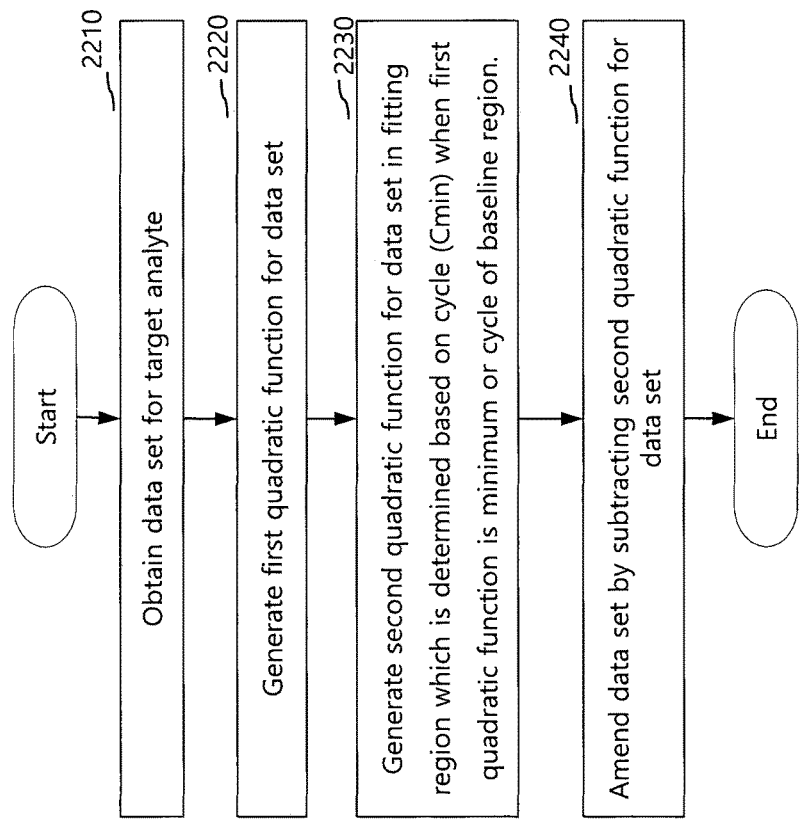
FIG. 11 is a flow chart illustrating a method for amending a data set according to an embodiment of the present invention.

FIG. 11 is a flow chart illustrating a method for amending a data set according to an embodiment of the present invention.

In step 2210, the data set for the target analyte is obtained. This step may be described with reference to descriptions described above. In step 2220, a first quadratic function for the data set is generated. The first quadratic function is a quadratic function fitted to the data set in the entire region. In step 2230, a second quadratic function for the data set in the fitting region determined based on a cycle of a baseline region of the data set is generated. The second quadratic function is a quadratic function fitted to the data set at the fitting region. In step 2240, the data set is amended by subtracting a value of the second quadratic function from a signal value of the data set.

Figure 12:
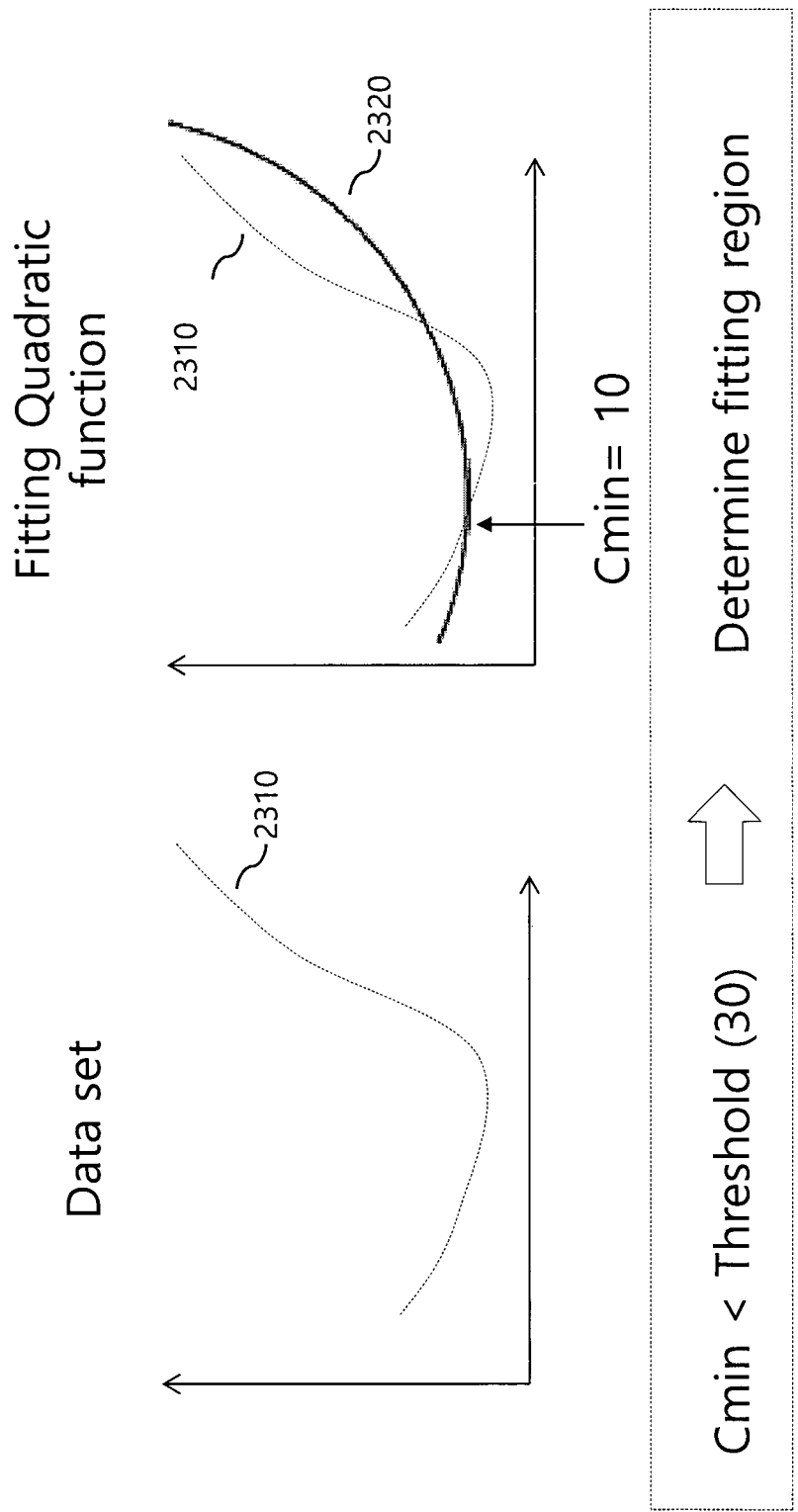
FIG. 12 illustrates a method for setting a fitting region using a first quadratic function.

FIG. 12 illustrates a method for setting a fitting region using a first quadratic function. The analysis device sets the fitting region based on the $C_{min}$ of the first quadratic function 2320. The data set 2310 is obtained from a signal-generating reaction. The data set 2310 may be obtained from an amplification device or obtained by amending the data set obtained from the amplifying device. For example, data sets may be obtained at high and low detection temperatures in the same channel and the data set 2310 may be obtained by subtracting the data set obtained at a high detection temperature from the data set obtained at a low detection temperature. The amplification device may also output the amended data set by amending the data set in consideration of interference between the channels.

The first quadratic function 2320 is given by fitting with the data set 2310. The analysis device generates the first quadratic function 2320 for the data set 2310 by applying a least squares method to a quadratic function ($y=ax^2+bx+c$) with three parameters and the data set 2310.

The analysis device determines the $C_{min}$ of the first quadratic function 2320 after generating the first quadratic function 2320. The analysis device may differentiate the first quadratic function 2320 to determine the $C_{min}$. In FIG. 12, the $C_{min}$ of the first quadratic function 2320 is cycle 10.

When the $C_{min}$ is less than the threshold value, the analysis device sets the fitting region by using the $C_{min}$. The analysis device may determine the end cycle of the fitting region by using the $C_{min}$. In one example, the analysis device may determine the $C_{min}$, the $C_{min}-1$, the $C_{min}-2$, the $C_{min}-3$, the $C_{min}-4$ or the $C_{min}-5$ as the end cycle of the fitting region. Alternatively, the analysis device may determine the $C_{min}$, the $C_{min}+1$, the $C_{min}+2$, the $C_{min}+3$, the $C_{min}+4$ or the $C_{min}+5$ as the end cycle of the fitting region. When the $C_{min}$ 10 is less than the threshold value 30, and the analysis device uses the $C_{min}$ to determine the end cycle of the fitting region.

The analysis device may determine the end cycle of the fitting region using the $C_{min}$ and the minimum fitting cycle. In one example, the minimum fitting cycle may be determined among cycle 10, 9, 8, 7, 6 or 5. The minimum fitting cycle may be determined according to a final cycle of the amplification reaction. The analysis device may select one of the $C_{min}$, the $C_{min}-1$, the $C_{min}-2$, the $C_{min}-3$, the $C_{min}-4$ or the $C_{min}-5$ and determine as the end cycle of the fitting region a larger value among the selected one and the minimum fitting cycle. When the minimum fitting cycle is cycle 9 and the $C_{min}$ is cycle 10, the analysis device may determine cycle 10 as the end cycle of the fitting region.

The analysis device sets a start fitting cycle. The starting fitting cycle is a minimum cycle of the fitting region. The fitting region is between the minimum cycle and the maximum cycle of the fitting region. The starting fitting cycle may be determined depending on the end cycle of an amplification reaction. In one example, when the end cycle is cycle 40, the starting fitting cycle may be one of cycle 0, 1 and 2. In one example, when the end cycle exceeds cycle 40, the starting fitting cycle may be one of cycle 4, 5, 6 and 7.

Figure 13:
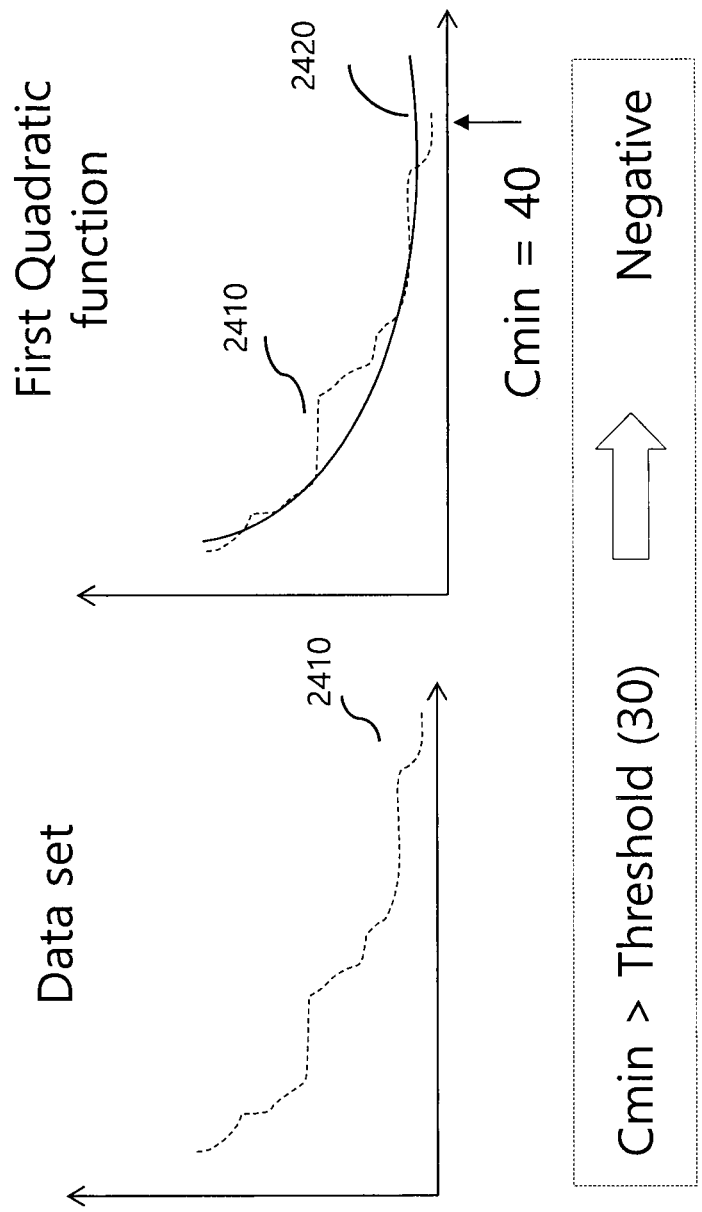
FIG. 13 illustrates a method for determining the absence of a target analyte in a sample by using the $C_{min}$.

FIG. 13 illustrates a method for determining the absence of a target analyte in a sample by using the $C_{min}$. The analysis device determines the $C_{min}$ and then determines that the target analyte in the sample is absent when the $C_{min}$ exceeds the threshold value. The first quadratic function 2420 is determined through fitting with the data set 2410. The analysis device generates the first quadratic function 2420 for the data set 2410 by applying a least squares method to a quadratic function ($y=ax^2+bx+c$) with three parameters and the data set 2410.

In FIG. 13, the data set 2410 is a negative sample and the signal value becomes smaller as the cycle is increased. Thus, the first quadratic function 2420 for the data set 2410 also has a decreasing shape. The $C_{min}$ is 40. Since the $C_{min}$ of the first quadratic function 2420 exceeds the threshold value (cycle 30), the analysis device determines that the target analyte in the sample is absent.

The present invention may determine whether the target analyte in the sample is absent by using only the data set and the $C_{min}$ of the first quadratic function. Therefore, the present invention may determine the absence of a target in a sample accurately, quickly, and easily without amending the data set and obtaining the Ct value using the threshold value as the prior arts.

Figure 14:
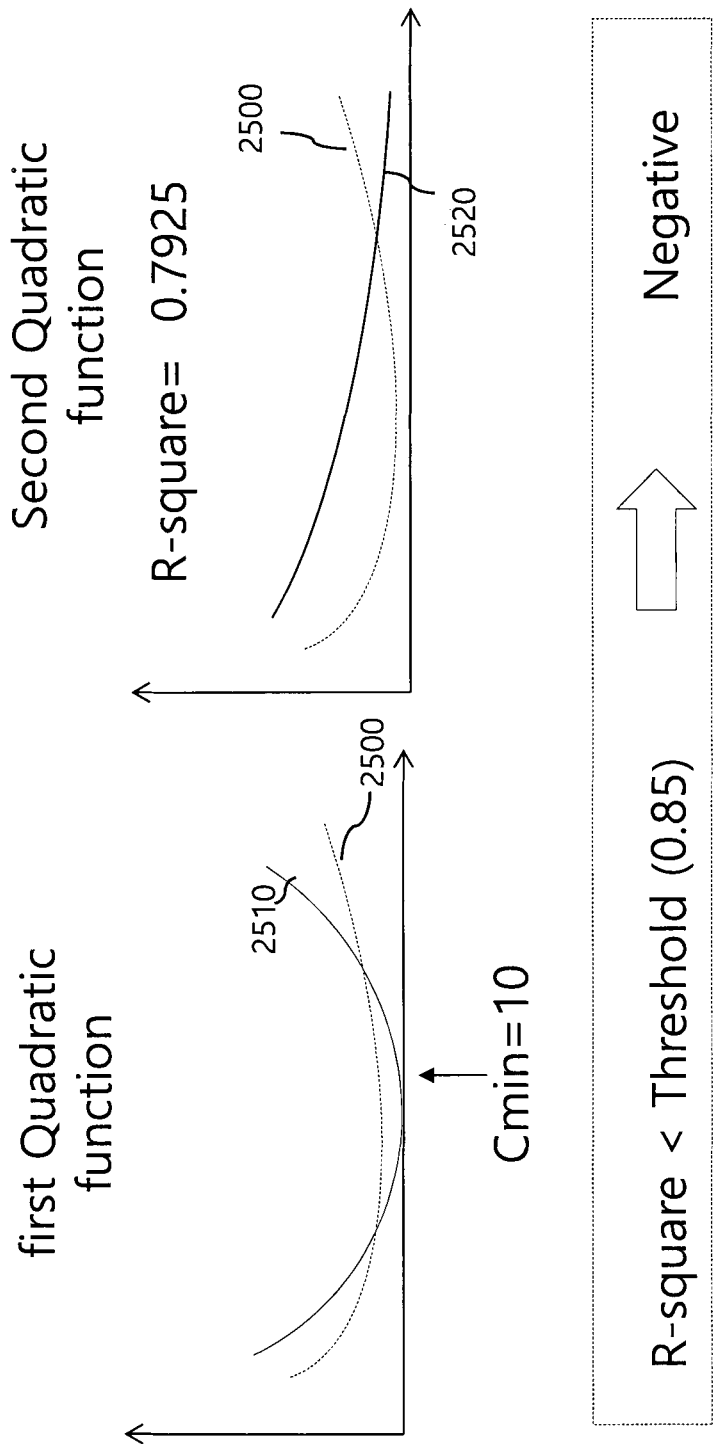
FIG. 14 illustrates a method for determining the absence of a target analyte in a sample using a second quadratic function and a fitting accuracy of a data set.

FIG. 14 illustrates a method for determining the absence of a target analyte in a sample using a second quadratic function and a fitting accuracy of a data set.

The analysis device sets a fitting region using the first quadratic function 2510. The analysis device generates the first quadratic function 2510 for the data set 2500. The analysis device calculates the $C_{min}$ of the first quadratic function 2510. Since the $C_{min}$ (cycle 10) is less than the threshold value (cycle 30), the analysis device determines the fitting region based on the $C_{min}$ or a cycle of the baseline region.

The analysis device generates a second quadratic function 2520 fitted to the data set 2500 in the fitting region. The analysis device determines the fitting accuracy for the second quadratic function 2520 in the fitting region.

In FIG. 14, the $R^2$ value as the fitting accuracy is 0.7925. Since the $R^2$ value is less than the threshold value (0.85), the analysis device determines that the target analyte in the sample is absent.

The present invention uses the $C_{min}$ of the first quadratic function 2510 or a cycle of the baseline region as the fitting region of the second quadratic function 2520, and uses the fitting accuracy as a direct indicator of target analyte analysis, particularly the absence of the target analyte, ensuring that the target analyte may be analyzed without false positive results or false negative results, particularly false positive results.

Figure 15:
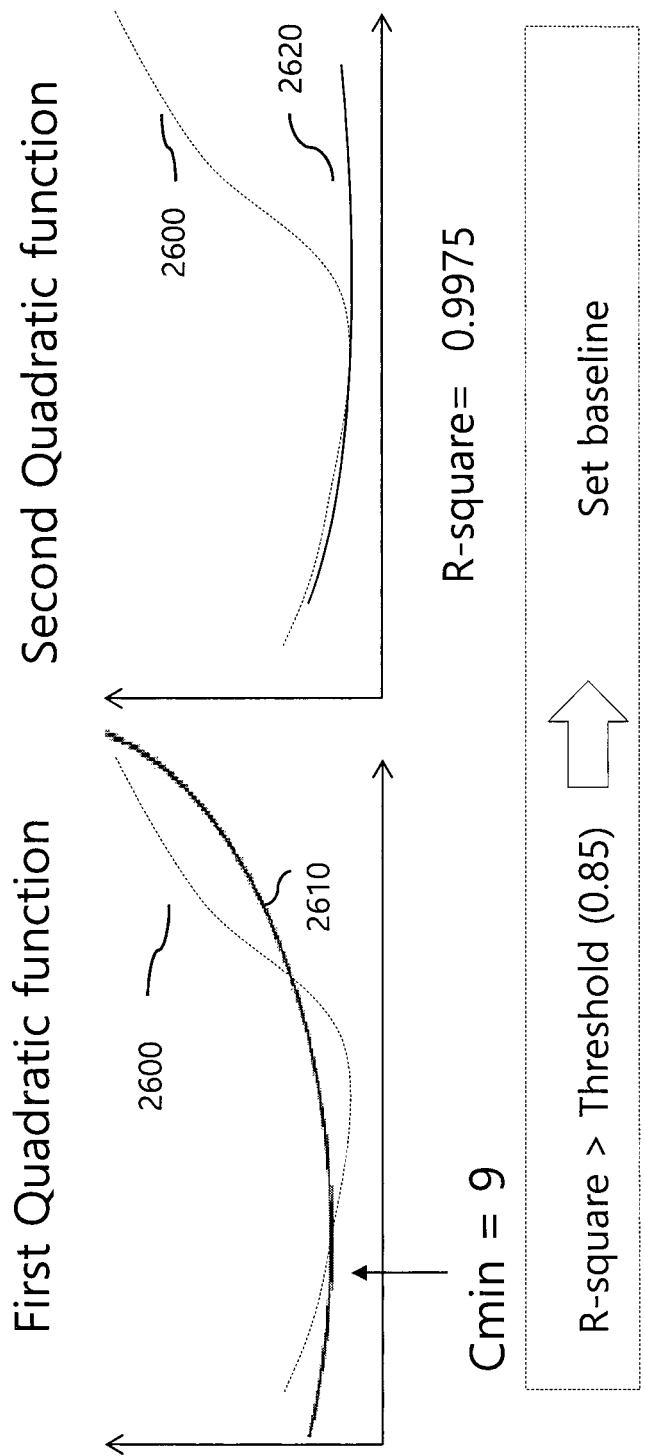
FIG. 15 illustrates a method for setting a baseline using a second quadratic function.

FIG. 15 illustrates a method for setting a baseline using a second quadratic function. The analysis device may set the second quadratic function 2620 as a baseline.

The analysis device sets the fitting region using a first quadratic function 2610. The analysis device generates the first quadratic function 2610 for the data set 2600. The analysis device calculates the $C_{min}$ of the first quadratic function 2610. Since the $C_{min}$ (cycle 9) is less than a threshold value (cycle 30), the analysis device may determine the fitting region based on the $C_{min}$ or the cycle of the baseline region.

The analysis device performs fitting for the data set 2600 in the fitting region. The analysis device generates the second quadratic function 2620 fitted to the data set 2600 in the fitting region.

The analysis device determines the fitting accuracy for the second quadratic function 2620 in the fitting region. The analysis device determines the fitting accuracy by using the signal values of the data set 2600 in the fitting region and the function value of the second quadratic function 2620. In FIG. 15, the $R^2$ value as the fitting accuracy is 0.7925. Because the $R^2$ value exceeds the threshold value (0.85), the analysis device determines the second quadratic function 2620 as the baseline.

The signal values for the data set 2600 in the fitting region are used when determining the second quadratic function 2620, but the function values of the second quadratic function 2620 are used in the entire cycles when the second quadratic function 2620 is set as the baseline.

The analysis device may amend the data set 2600 by subtracting the function value of the second quadratic function 2620 from the signal value of the data set 2600 in the entire cycle. The analysis device may analyze the amended data set to determine the presence or absence of target analyte in the sample.

The present invention has the advantage that the baseline may be set by simply analyzing the data set 2600 without analyzing a separate analyte such as a negative control.

Figure 16:
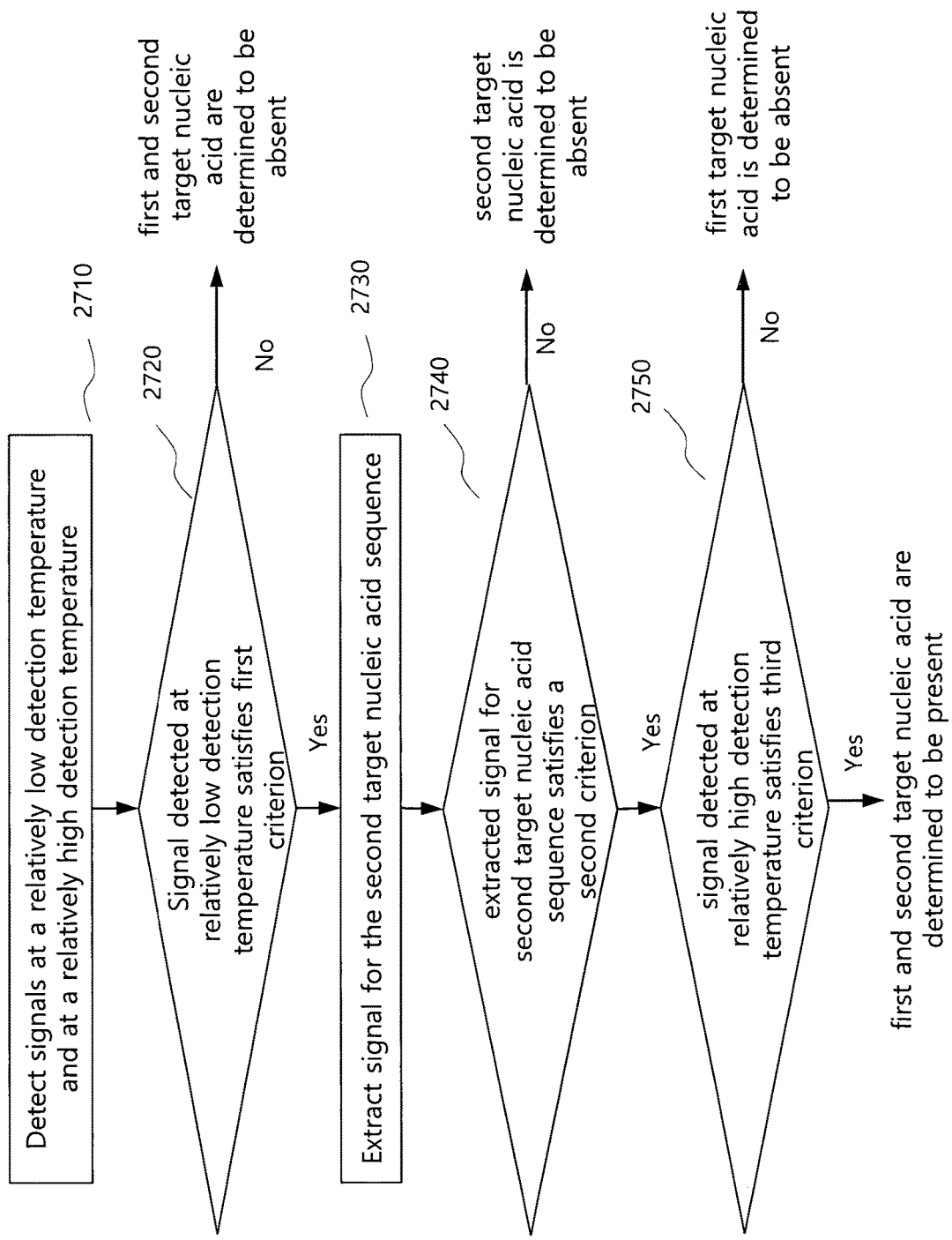
FIG. 16 is a flow chart for the method of the present invention based on the MuDT technology.
Figure 17:
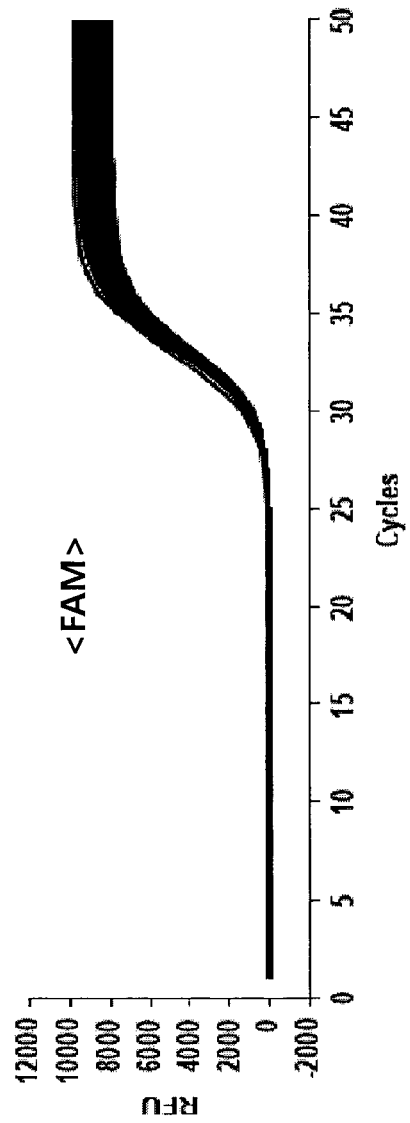
FIGS. 17 to 20 represent an analysis result for an un-normalized data set.
Figure 18:
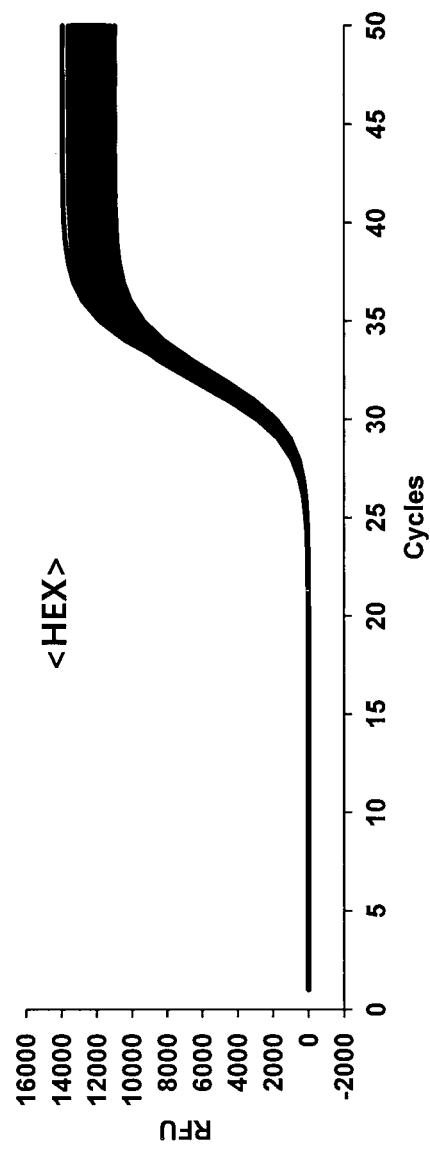
Figure 19:
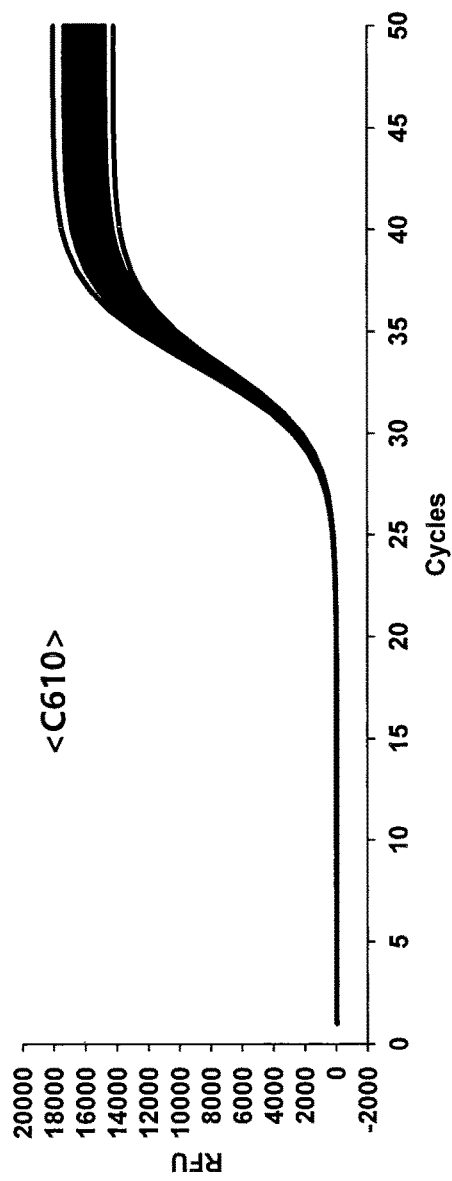
Figure 20:
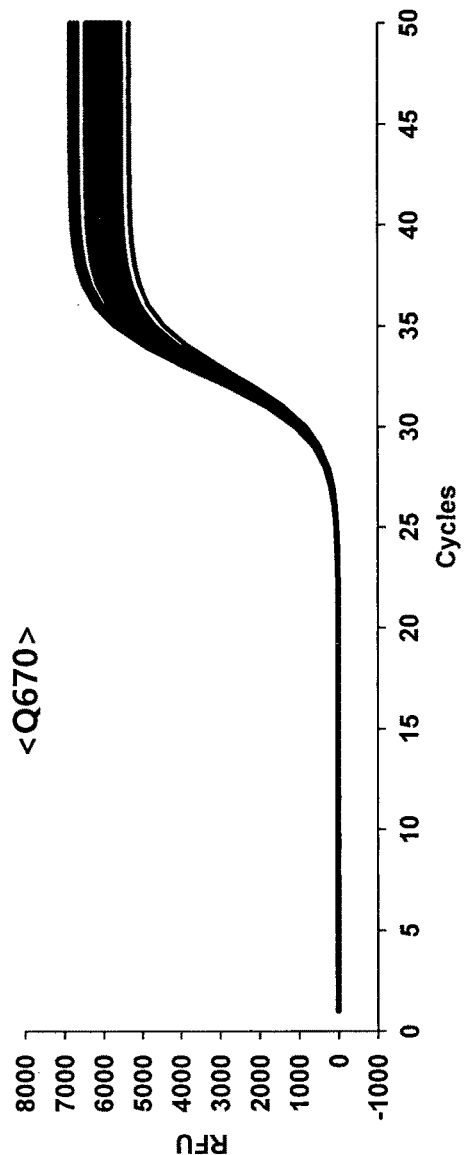
Figure 21:
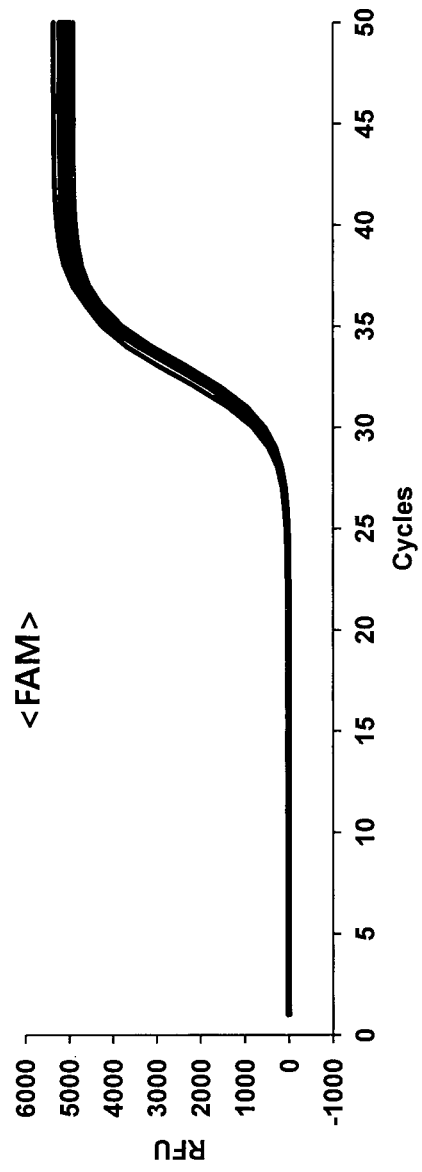
FIGS. 21 to 24 represent an analysis result for a normalized data set.
Figure 22:
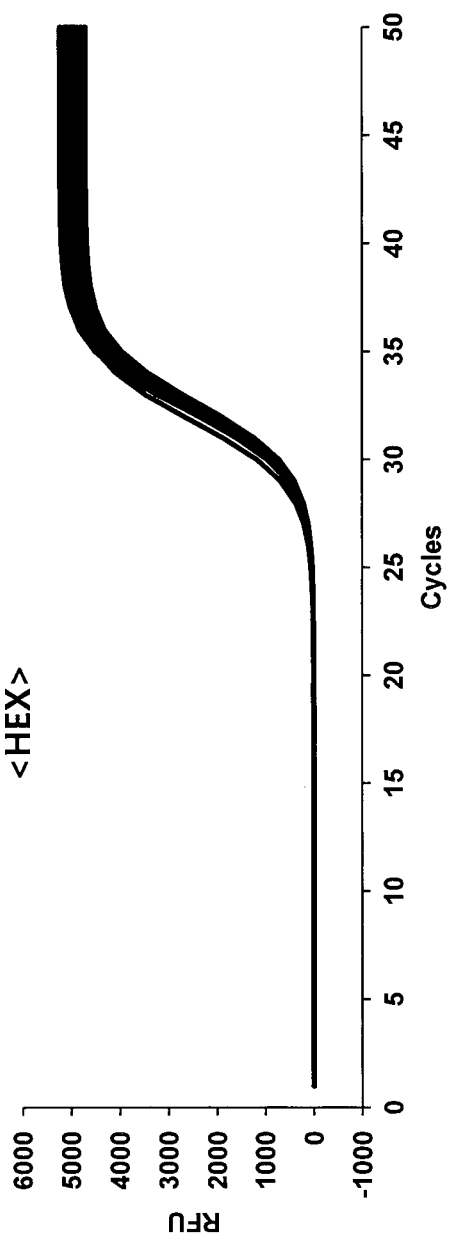
Figure 23:
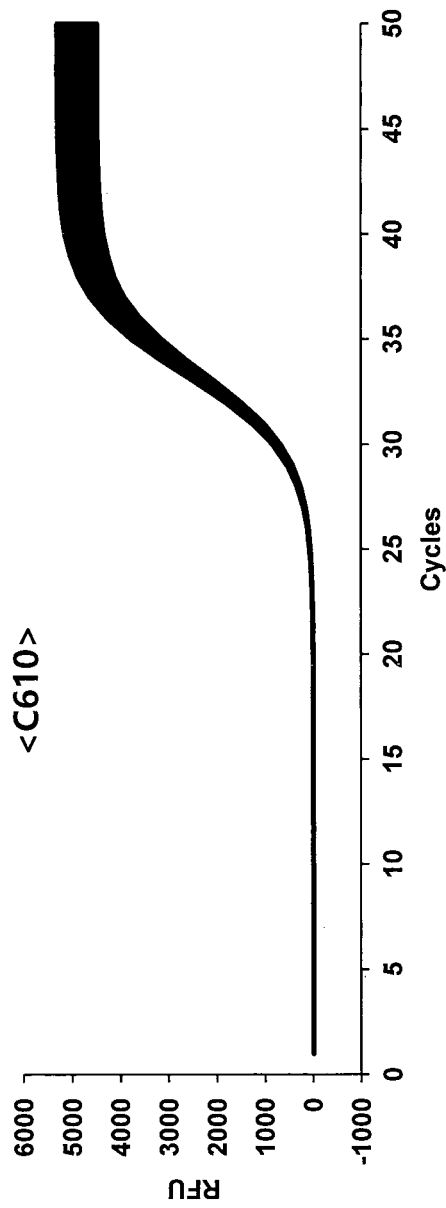
Figure 24:
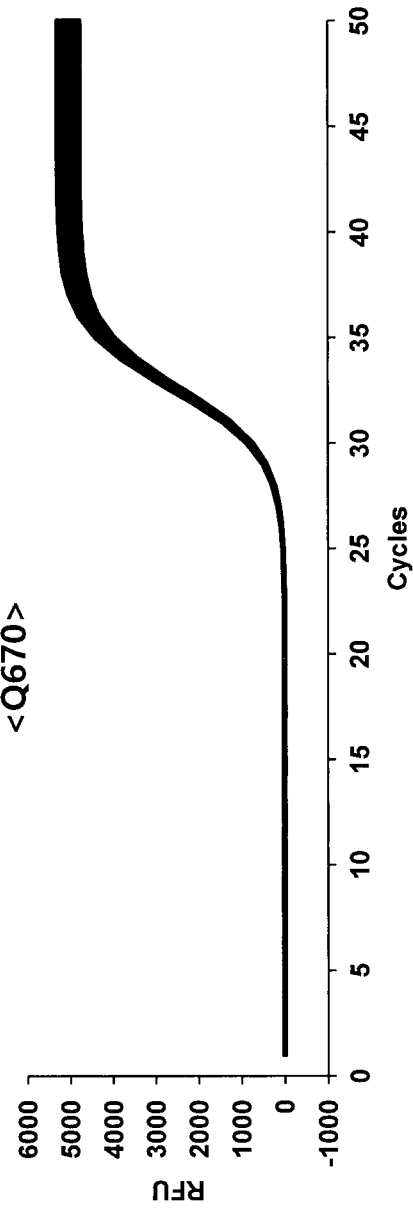

FIG. 16 is a flow chart for the method of the present invention based on the MuDT technology. Referring to FIG. 16, the method of the present invention will be described in detail in each step.

In step 2710, the signals are detected at two different temperatures. The signals are detected at a relatively low detection temperature and at a relatively high detection temperature.

In step 2720, the signal detected at the relatively low detection temperature is evaluated. It is determined whether the signal detected at the relatively low detection temperature satisfies a first threshold defined by the first threshold value. Alternatively, the first signal displacement is determined.

When the signal detected at the relatively low detection temperature satisfies the first criterion, step 2730 is proceeded. When the signal detected at the relatively low detection temperature does not satisfy the first criterion, the first target nucleic acid sequence and the second target nucleic acid is determined to be absent in the sample, and the step 2730 is not proceeded.

That the signal detected at the relatively low detection temperature does not satisfy the first criterion means that the first target nucleic acid sequence and the second target nucleic acid sequence in the sample are absent. Therefore, it is not necessary to perform the step 2730, and the procedure is terminated.

That the signal detected at the relatively low detection temperature satisfies the first criterion means that the first target nucleic acid sequence or the second target nucleic acid sequence is likely to be present in the sample. Even if the signal detected at the relatively low detection temperature satisfies the first criterion, it does not necessarily mean that one or more target nucleic add sequences of two target nucleic acid sequences are present in the sample.

The first criterion may be defined by a first threshold value. "The first threshold value" used in this step refers to a threshold value used for determining the significance of the signal detected at the relatively low detection temperature. "The second threshold value" refers to a threshold value used to determine the significance of the signal for the second target nucleic acid sequence. "The third threshold value" refers to a threshold value used to determine the significance of the signal for the first target nucleic acid sequence. "The third threshold value" refers to a threshold value used to determine the significance of the signal detected at the relatively high detection temperature. Significance of the signal means that the signal generated at a certain temperature is generated at a meaningful level relative to a specific threshold value. The significance of the signal may be determined by a suitable threshold for distinguishing a signal generated by a specific signal-generating means from other signals. Specifically, the threshold used to determine the significance of the signal is set to any value that may exclude a signal not derived from a nucleic acid sequence of interest, for example, a background signal or a noise signal. As an example, if the signal is amplified as the amplification reaction proceeds, the signal above the threshold may be determined to be significant.

The threshold values (first, second, and third threshold values) may be determined according to a conventional threshold value setting method. For example, the threshold values may be determined in consideration of background signal, sensitivity, label characteristics, signal variation of the detector, or error range. Threshold values may be set in the exponential region of the signal-generating reaction. The threshold values may be set to values greater than the signal value of the baseline region, but not greater than the signal value of the plateau region of the signal-generating reaction. Alternatively, the threshold values may be set to a value obtained by multiplying the standard deviation of the signal values of the baseline region in the baseline-subtracted amplification curve by a predetermined value (e.g., 10).

The threshold values may be set automatically by the detector or manually by the operator. For example, the first threshold value may be 100 (RFU).

In step 2730, a signal for the second target nucleic acid sequence is extracted. When the signal detected at the relatively low detection temperature in step 2720 satisfies the first criterion, the signal for the second target nucleic acid sequence is extracted. One of the features of the present invention is to perform the step of extracting the signal for the second target nucleic acid sequence even if the signal detected at the relatively high detection temperature does not satisfy the third criterion.

The present invention may perform the step 2730 of extracting a signal regardless of the signal detected at the relatively high detection temperature even when the signal detected at the relatively high detection temperature does not satisfy the third criterion.

The process of extracting a signal for a specific target nucleic acid sequence using signals detected at two different detection temperatures and a reference value is referred to as a 'signal extraction process' herein.

In step 2740, the signal for the second target nucleic acid sequence is evaluated. Whether the extracted signal for the second target nucleic acid sequence satisfies a second criterion defined by a second threshold value or a second signal displacement is identified. When the signal for the second target nucleic acid sequence satisfies the second criterion, the second target nucleic acid sequence is determined to be present in the sample. When the signal for the second target nucleic acid sequence does not satisfy the second criterion, the second target nucleic acid sequence is determined to be absent in the sample. The second criterion is defined by the second threshold value or the second signal displacement.

Before applying the non-linear function fitting method, the signal for the second target nucleic acid sequence may be amended using a quadratic function, and the absence of the second target nucleic acid sequence may be determined using the fitting accuracy between the quadratic function and the signal for the second target nucleic acid sequence.

Before performing the fitting, the analysis device sets a baseline for the signal for the second target nucleic acid sequence, subtracts the baseline from the signal for the second target nucleic acid sequence, and generates a signal for the amended signal for the second target nucleic acid sequence. The analysis device may apply the non-linear function fitting method to the signal for the amended signal for the second target nucleic acid sequence.

In one embodiment of the present invention, the analysis device may set a fitting region, generate a quadratic function fitted to the signal for the second target nucleic acid sequence in the fitting region, and set the quadratic function as a baseline. The fitting region may be a preset. In one example, the fitting region may be set from cycles 4 to 12. The analysis device generates the quadratic function that best matches the signal values from cycles 4 to 12 through fitting. In this case, the quadratic function may have a symmetry axis and the symmetry axis may be in the range of the end cycle±10, the end cycle±8, the end cycle±6, the end cycle±5, the end cycle±3, the end cycle±2, or the end cycle±1 of the signal-generating reaction.

The analysis device may perform the fitting the non-linear function with an amended data set (or the amended signal for second target nucleic acid sequence) and determine the presence of absence of the second target nucleic acid sequence using the fitting accuracy between the fitted non-linear function and the amended data set.

In step 2750, the signal for the first target nucleic acid sequence is evaluated.

The analysis device identifies whether the signal detected at the relatively high detection temperature satisfies a third criterion defined by a third threshold or a third signal displacement. When the signal detected at the relatively high detection temperature satisfies the third criterion, the first target nucleic acid sequence is determined to be present in the sample, and when the signal detected at the relatively high detection temperature does not satisfy the third criterion, the target nucleic acid sequence is determined to be absent in the sample.

In one embodiment of the present invention, a non-linear function fitting method may be used to finally determine that the first target nucleic acid sequence is present in the sample even if the signal detected at the relatively high detection temperature satisfies the third criterion.

The step 2750 may be performed between the steps 2710 and 2720, between the steps 2720 and 2730, between the steps 2730 and 2740, or after step 2740.

The features and advantages of the present invention are summarized as follows:

(a) The present invention utilizes a fitting accuracy of a non-linear function to a data set as a direct indicator for target analyte analysis, particularly detection of target analytes, such that target analytes may be detected without false positive or false negative results, particularly false positive results.

(b) In an embodiment of the present invention in which a target nucleic acid sequence is detected by a nucleic acid amplification reaction, the present invention may more accurately, quickly and easily determine the presence or absence of target analytes in samples without setting a threshold value for obtaining a $C_t$ value.

(c) In an embodiment of the present invention in which a target nucleic acid sequence is detected by a nucleic add amplification reaction, a target nucleic acid sequence may be detected by using not only a fitting accuracy of a non-linear fitting function but also (i) a displacement of a data set, an amended data set or a non-linear fitting function, (ii) a maximum slope of a non-linear fitting function and (iii) a parameter determining a shape of a non-linear fitting function (particularly, a4 of a four-parametric sigmoid function), thereby ensuring to completely eliminate an erroneous target determination, particularly false positives in various clinical samples.

(d) The thresholds applied to the parameters used in determination of the presence or absence of target analytes such as a displacement, a maximum slope and a shape-determinative parameter are set in consideration of a signal pattern of a data set (for example, a data set of a nucleic acid amplification reaction) unlikely to conventional technologies considering a specific signal value. In this regard, the present invention has prominent advantages in which it is not necessarily required to set the thresholds specifically for each experiment, each reaction, each product and each device. For example, when threshold values suitable for a data set of a certain nucleic acid amplification reaction are set in advance, the threshold values preset may be applied to all subsequent nucleic acid amplification reactions. Alternatively, the threshold values may be preset for each type of samples and the threshold value preset may be applied to all nucleic acid amplification reactions using a corresponding identical sample type. For example, when threshold values for a nucleic acid amplification reaction using a stool as samples are preset in advance, the threshold values preset may be applied to all subsequent nucleic acid amplification reactions using stool samples.
(e) Since the present invention analyzes target analytes by using a signal pattern rather than signal intensity, the noise influence may be greatly reduced in the present invention.
(f) In an embodiment using the SBN technology, a non-linear fitting function is applied to data set normalized using a normalization coefficient.
(g) In an embodiment using the SBN technology, the present invention may amend a data set in a more convenient manner and greatly reduce signal variation of inter-instrument and intra-instrument. The normalized data set by using the SBN technology permits to set threshold values for the parameters of a non-linear fitting function in much more convenient manner.
(h) Since the present invention determines the presence or absence of target analytes by analyzing whether or not the shape of the normalized data set matches with the shape of a typical amplification curve, it is very unlikely to cause false positives due to noise or jump error.
(i) According to an embodiment, since the present invention derives detection results by analyzing at least two properties of a non-linear fitting function rather than any one of the properties, it is very advantageous in terms of reducing false positive and false negative results.
(j) In an embodiment using the SBN technology, the present invention with help of data normalization using an appropriate reference value becomes more advantageous in reduction of amounts of signal-generating means (e.g., primer and probe).
(k) In an embodiment, the present invention uses a cycle at which a first quadratic function for data sets is minimum as a direct indicator to detect particularly the absence of target analytes and may analyze target analytes without false positive and false negative results, particularly false positive results.
(l) In an embodiment, the present invention uses (i) a cycle at which a first quadratic function for data sets is minimum or (ii) a cycle of the baseline region as a fitting region of a second quadratic function, and analyzes a target analyte by using a fitting accuracy of the second quadratic function as a direct indicator of determination of the absence of a target analyte without false positive or false negative results, particularly false positive results.
(m) In an embodiment, for amending a data set, the present invention may use a second quadratic function determined based on (i) a cycle at which a first quadratic function for data sets is minimum or (ii) a cycle of the baseline region.
(n) A threshold for a cycle at which a first quadratic function for data sets is minimum and a threshold value for the fitting accuracy of a second quadratic function are set in consideration of a signal pattern of a data set (for example, a data set of a nucleic acid amplification reaction) unlikely to conventional technologies considering a specific signal value. In this regard, the present invention has prominent advantages in which it is not necessarily required to set the thresholds specifically for each experiment, each reaction, each commercial product and each device.

The present invention will now be described in further detail by examples. It would be obvious to those skilled in the art that these examples are intended to be more concretely illustrative and the scope of the present invention as set forth in the appended claims is not limited to or by the examples.

EXAMPLES

Example 1: Detection of Gastrointestinal Tract Infectious Virus

Obtaining a Data Set

Allplex™ GI-Virus Assay of Seegene, Inc. was used to detect Norovirus GI, Norovirus GII, Adenovirus and Rotavirus, which are major causes of acute diarrhea.

A nucleic acid amplification reaction was performed for 30 samples on CFX96™ Real-Time PCR Detection Systems (Bio-Rad). The nucleic acid amplification reaction was performed for a total of 45 cycles of at 95° C. for 10 seconds, at 60° C. for 1 minute and at 72° C. for 30 seconds. PTOCE (WO 2012/096523) and MuDT (WO 2015/147412) technologies were used to obtain data sets from CFX96. The data sets include signal values at all amplification cycles.

The 30 samples are those that had been identified as either positive or negative samples in clinical tests (20 positive samples and 10 negative samples) as shown in Table 1.

Samples 1, 2, 3, 6 and 7 are infected with Norovirus GII, Samples 9, 10, 11, 13 and 14 with Adenovirus, Samples 16, 17, 19, 20 and 21 with Norovirus GI and Samples 24, 26, 27, 28 and 29 with Rotavirus virus.

TABLE 1

| sample1 | Positive |
| sample2 | Positive |
| sample3 | Positive |
| sample4 | negative |
| sample5 | negative |
| sample6 | Positive |
| sample7 | Positive |
| sample8 | negative |
| sample9 | Positive |
| sample10 | Positive |
| sample11 | positive |
| sample12 | negative |
| sample13 | positive |
| sample14 | positive |
| sample15 | negative |
| sample16 | positive |
| sample17 | positive |
| sample18 | negative |
| sample19 | positive |
| sample20 | positive |
| sample21 | positive |
| sample22 | negative |
| sample23 | negative |
| sample24 | positive |
| sample25 | negative |
| sample26 | positive |
| sample27 | positive |
| sample28 | positive |
| sample29 | positive |
| sample30 | negative |

Obtaining an Amended Data Set

A negative control subtraction was performed to amend the data set. The negative control contains only components of Allplex™ GI-Virus Assay without samples. When performing the nucleic acid amplification reaction for the samples, the amplification reaction of the negative control was simultaneously performed in the same plate to obtain a data set for the negative control. The signal value of the negative control was subtracted from signal values of the data set at each cycle to obtain an amended data set. The negative control subtraction was performed for each sample, thereby obtaining amended data sets.

Determining the Presence or Absence of Target Nucleic Acid Molecules Using a Sigmoid Function Fitting (a) Obtaining a Sigmoid Fitting Function Fitting with a sigmoid function was performed by using the four-parametric sigmoid function of Equation III for the amended data set obtained from each of the samples. The LM algorithm (Levenberg-Marquardt algorithm; Christian Kanzow et al., JCAM, 172(2):375(2004)) was used to obtain a sigmoid function fitted to the amended data set.

(b) First Negative Filtering by the Displacement of the Sigmoid Function

The displacement of the sigmoid function was used to filter out negative samples. The displacement of the sigmoid fitting function was obtained by calculating the difference between the maximum RFU and the minimum RFU of the sigmoid fitting function. The negative samples were filtered out by comparing the calculated displacement with a threshold value for displacement (RFU 100). Samples with a displacement of the fitted sigmoid function of less than RFU 100 were determined negative.

5 samples were shown to be less than RFU 100 of displacements of the sigmoid functions and filtered out to be negative (Samples 5, 8, 12, 23 and 25) (Table 2).

TABLE 2

| Sample | Displacement (ΔRFU) |
| --- | --- |
| sample1 | 3452 |
| sample2 | 1202 |
| sample3 | 3224 |
| sample4 | 260 |
| sample5 | −395 |
| sample6 | 3393 |
| sample7 | 4047 |
| sample8 | −913 |
| sample9 | 1916 |
| sample10 | 1897 |
| sample11 | 1516 |
| sample12 | −85 |
| sample13 | 2553 |
| sample14 | 2670 |
| sample15 | 412 |
| sample16 | 1584 |
| sample17 | 621 |
| sample18 | 307 |
| sample19 | 1953 |
| sample20 | 2111 |
| sample21 | 2209 |
| sample22 | 315 |
| sample23 | −82 |
| sample24 | 2470 |
| sample25 | −121 |
| sample26 | 2034 |
| sample27 | 700 |
| sample28 | 4588 |
| sample29 | 112 |
| sample30 | 3452 |

(c) Second Negative Filtering by a Maximum Slope of the Sigmoid Fitting Function The second negative filtering using the maximum slope of the sigmoid fitting function was carried out for the remaining 25 samples. The maximum slope was calculated by differentiating the sigmoid fitting function for each sample [i.e., the first derivative maximum (FDM) value for the sigmoid function]. The threshold value for the maximum slope was set as 28.

As summarized in Table 3, the maximum slopes of the sigmoid functions of 4 samples (Samples 15, 18, 22 and 30) were less than 28 and the 4 samples are filtered out to be negative.

TABLE 3

| Sample | Maximum slope |
| --- | --- |
| sample1 | 672 |
| sample2 | 127 |
| sample3 | 665 |
| sample4 | 56 |
| sample5 | — |
| sample6 | 306 |
| sample7 | 472 |
| sample8 | — |
| sample9 | 194 |
| sample10 | 246 |
| sample11 | 420 |
| sample12 | — |
| sample13 | 236 |
| sample14 | 193 |
| sample15 | 11 |
| sample16 | 149 |
| sample17 | 43 |
| sample18 | 8 |
| sample19 | 157 |
| sample20 | 273 |
| sample21 | 355 |
| sample22 | 12 |
| sample23 | — |
| sample24 | 453 |
| sample25 | — |
| sample26 | 61 |
| sample27 | 235 |
| sample28 | 53 |
| sample29 | 479 |
| sample30 | 5 |

(d) Final Decision of Positive or Negative Samples by a Fitting Accuracy $R^2$ Value Fitting accuracy was calculated for the remaining 21 samples excluding 9 samples determined to be negative. $R^2$ value was used as the fitting accuracy. $R^2$ value was calculated using Equation IV and the threshold value for $R^2$ value was set 0.87. Samples having $R^2$ value of less than 0.87 were determined to be negative.

As shown in Table 4, $R^2$ value of only 1 sample among 21 samples was less than 0.87 and determined to be negative (Sample 4). The remaining 20 samples with $R^2$ values of more than 0.87 were verified to be positive.

TABLE 4

| Samples | $R^2$ value |
| --- | --- |
| sample1 | 0.998 |
| sample2 | 0.997 |
| sample3 | 0.994 |
| sample4 | 0.203 |
| sample5 | — |
| sample6 | 0.992 |
| sample7 | 0.992 |

TABLE 4-continued

| Samples | R² value |
|---|---|
| sample8 | — |
| sample9 | 0.997 |
| sample10 | 0.998 |
| sample11 | 0.962 |
| sample12 | — |
| sample13 | 0.993 |
| sample14 | 0.994 |
| sample15 | — |
| sample16 | 0.996 |
| sample17 | 0.993 |
| sample18 | — |
| sample19 | 0.999 |
| sample20 | 0.999 |
| sample21 | 0.998 |
| sample22 | — |
| sample23 | — |
| sample24 | 0.999 |
| sample25 | — |
| sample26 | 0.993 |
| sample27 | 0.994 |
| sample28 | 0.995 |
| sample29 | 0.998 |
| sample30 | — |

Example 2: Detection of Gastrointestinal Tract Infectious Virus by a Conventional Method (Comparative Example for Example 1)

Obtaining a Data Set

Data set was obtained by the same procedures as Example 1.

Obtaining an Amended Data Set

Noise was removed by a nearest neighbor smoothing algorithm (Winfried Stute et al., Journal of Multivariate Analysis, 34:61(1990)). A baseline was obtained by performing a linear regression until the difference of the raw data set was more than a reference threshold value and then a baseline subtraction was performed to obtain the amended data set.

Determining the Presence or Absence of Target Nucleic Acid Molecules Using a Threshold Value for C Values Each of the samples was determined to be positive or negative by determining whether the amended data set exceeds a threshold value for $C_t$ values. When there was a signal value exceeding the threshold value in the amended data set, the sample was determined positive. When there was no signal value exceeding the threshold value, the sample was determined negative. The threshold values for $C_t$ values were 120, 120, 60 and 120 for Norovirus GI, Norovirus GII, Adenovirus and Rotavirus, respectively.

TABLE 5

| | |
|---|---|
| sample1 | positive |
| sample2 | positive |
| sample3 | positive |
| sample4 | positive |
| sample5 | positive |
| sample6 | positive |
| sample7 | positive |
| sample8 | positive |
| sample9 | positive |
| sample10 | positive |
| sample11 | positive |
| sample12 | negative |
| sample13 | positive |
| sample14 | positive |
| sample15 | negative |
| sample16 | positive |
| sample17 | positive |
| sample18 | negative |
| sample19 | positive |
| sample20 | positive |
| sample21 | positive |
| sample22 | negative |
| sample23 | negative |
| sample24 | positive |
| sample25 | negative |
| sample26 | positive |
| sample27 | positive |
| sample28 | positive |
| sample29 | positive |
| sample30 | negative |

As summarized in Table 5, 7 samples were analyzed as negative and 23 samples as positive. 3 samples (Samples 4, 5 and 8) among 23 positive samples had been identified as negative samples in the clinical trial results. Therefore, it would be understood that conventional technologies by application of threshold values are more likely to give false positive results than the present invention.

Summary of Experiment Results

Thirty (30) samples were analyzed by the present invention and the conventional technology. The total number of samples was 30, and the number of positive samples had been determined to be 20 and the number of negative samples to be 10 by the clinical trial.

TABLE 6

| Samples | Clinical trial | Conventional technology | Present invention |
|---|---|---|---|
| sample1 | positive | positive | Positive |
| sample2 | positive | positive | Positive |
| sample3 | positive | positive | positive |
| sample4 | negative | positive | negative |
| sample5 | negative | positive | negative |
| sample6 | positive | positive | positive |
| sample7 | positive | positive | positive |
| sample8 | negative | positive | negative |
| sample9 | positive | positive | positive |
| sample10 | positive | positive | positive |
| sample11 | positive | positive | positive |
| sample12 | negative | negative | negative |
| sample13 | positive | positive | positive |
| sample14 | positive | positive | positive |
| sample15 | negative | negative | negative |
| sample16 | positive | positive | positive |
| sample17 | positive | positive | positive |
| sample18 | negative | negative | negative |
| sample19 | positive | positive | positive |
| sample20 | positive | positive | positive |
| sample21 | positive | positive | positive |
| sample22 | negative | negative | negative |
| sample23 | negative | negative | negative |
| sample24 | positive | positive | positive |
| sample25 | negative | negative | negative |
| sample26 | positive | positive | positive |
| sample27 | positive | positive | positive |
| sample28 | positive | positive | positive |
| sample29 | positive | positive | positive |
| sample30 | negative | negative | negative |

As shown in Table 6, 3 positive samples by the conventional technology were false results. The present invention exhibited all matched analysis results with those of the clinical trial in all of 30 samples. Therefore, it would be appreciated that the present method enables to determine the presence or absence of target nucleic acid molecules in samples in more accurate, rapid and convenient manners without setting threshold values for obtaining $C_t$ values.

Example 3: Normalization of Data Set and Analysis of Target Analyte in Samples by Non-Linear Fitting Function Data sets were amended by normalization in accordance with the SBN (Specific Background signal-based Normalization) method, and the presence or absence of target analytes were then analyzed using a non-linear fitting function in accordance with the present method.

Obtaining a Data Set

Real-time polymerase chain reactions were performed for 4 target nucleic acid sequences. The 4 target nucleic acid sequences were simultaneously amplified for total 50 cycles using three CFX96 Real-Time PCR devices (Bio-Rad) and TaqMan probes were used as a signal-generating means for each target nucleic acid sequence. 96 reactions in 96 wells for each device and each channel were performed under the same conditions using the samples containing the same target nucleic acid sequence with the same concentration, and data sets of 12 groups (3 devices×4 channels) were obtained.

TABLE 7

| Title | Real-time PCR Device |
|---|---|
| Equipment 1 | CFX96 Real-time cycler (Bio-rad) |
| Equipment 2 | |
| Equipment 3 | |

Normalizing a Data Set

The data set was amended by applying a reference value for each equipment/channel. The reference value for each equipment/channel was determined by using a ratio of the total signal change value (TSC) of a data set for each equipment/channel to the reference total signal change value (reference TSC; R-TSC). The reference total signal change value was arbitrarily determined as RFU 5,000 for all equipment/channels, and the total signal change value of the data set was determined based on the average value of 96 reactions for each equipment/channel. The signal value at the reference cycle of the data set was amended by the ratio and the amended signal value at the reference cycle was used as the reference value to be applied to data sets obtained from a corresponding channel of a corresponding device.

In the following steps 1 to 3, the reference value was determined from the data set for each device and channel. In step 4, the data set was amended using the determined reference value for each device and channel.

<Step 1>

The reference cycle was determined to be cycle 5 of the data set and the signal value at cycle 5 was used for determination of the reference value. Also, the total signal change value of the data set was calculated by subtracting a signal value at the reference cycle from a signal value at the last $50^{th}$ cycle. The TSCs and signal values at the reference cycles are summarized in Table 8.

TABLE 8

| Channels | Devices | Total signal change value of data set | Signal value at the reference cycle of data set |
|---|---|---|---|
| Channel 1 | Device 1 | 2,567 | 5,635 |
| (FAM) | Device 2 | 4,365 | 8,495 |
| | Device 3 | 8,704 | 14,158 |
| Channel 2 | Device 1 | 3,572 | 2,877 |
| (HEX) | Device 2 | 6,087 | 3,497 |
| | Device 3 | 12,478 | 4,631 |
| Channel 3 | Device 1 | 4,757 | 2,069 |
| (CalRed 610) | Device 2 | 11,078 | 2,451 |
| | Device 3 | 16,361 | 2,642 |
| Channel 4 | Device 1 | 928 | 2,923 |
| (Quasar 670) | Device 2 | 3,022 | 4,284 |
| | Device 3 | 5,984 | 5,981 |

<Step 2>

The reference total signal change value (reference TSC; R-TSC) to be used for determination of the reference value for each equipment and channel together with the calculated total signal change value was designated as RFU 5,000.

<Step 3>

The reference value to be applied to each device was calculated by using the total signal change value, the signal value at the reference cycle and the reference total signal change value described above as follows:

Reference Value=Signal Value at the Reference Cycle of Each Data Set/(Total Signal Change Value/Reference Total Signal Change Value)

The reference values used for amendment of the data sets were determined as shown in Table 9.

TABLE 9

| Channel | Device | TSC | R-TSC | Ratio of TSC to R-TSC | Signal value at reference cycle | Reference value |
|---|---|---|---|---|---|---|
| 1 | 1 | 2,567 | 5,000 | 0.5133 | 5,635 | 10,978 |
| | 2 | 4,365 | 5,000 | 0.8730 | 8,495 | 9,731 |
| | 3 | 8,704 | 5,000 | 1.7407 | 14,158 | 8,134 |
| 2 | 1 | 3,572 | 5,000 | 0.7145 | 2,877 | 4,027 |
| | 2 | 6,087 | 5,000 | 1.2174 | 3,497 | 2,873 |
| | 3 | 12,478 | 5,000 | 2.4656 | 4,631 | 1,856 |
| 3 | 1 | 4,757 | 5,000 | 0.9514 | 2,069 | 2,175 |
| | 2 | 11,078 | 5,000 | 2.2157 | 2,451 | 1,106 |
| | 3 | 16,361 | 5,000 | 3.2722 | 2,642 | 808 |
| 4 | 1 | 928 | 5,000 | 0.1855 | 2,923 | 15,758 |
| | 2 | 3,022 | 5,000 | 0.6045 | 4,284 | 7,088 |
| | 3 | 5,984 | 5,000 | 1.1969 | 5,981 | 4,997 |

<Step 4>

Using the reference values determined above, the data sets of the 12 groups were normalized as follows: A normalization coefficient was calculated using a signal value at the reference cycle in a data set of each well and the reference value determined in Step 3: Normalization coefficient=signal value at the reference cycle/reference value.

The signal values at all cycles were normalized using the normalization coefficient, thereby obtaining the normalized data sets of 12 groups. Normalized signal value=signal value of a data set÷normalization coefficient.

Baselining

The baselining for 12 groups of data sets and the normalized data sets was performed. The baselining was carried out using a quadratic function with a symmetry axis, $y=a(x-50)^2+c$. A fitted region for baselining was determined as cycles 4 to 12. A quadratic function fitted to the signal values of the data set from cycle 4 to cycle 12 was generated. By subtracting values of the quadratic function from the signal values of the data set, 12 baselined data sets and 12 normalized/baselined data sets were obtained.

Obtaining a Sigmoid Function as a Non-Linear Fitting Function

Fitting with the sigmoid function was performed by using the four-parametric sigmoid function of Equation III for the 12 baselined data sets (see FIGS. 17 to 20) and the 12 normalized/baselined data sets (see FIGS. 21 to 24).

$R^2$ values, the displacement values and the maximum slope values were calculated as Example 1.

Determining the Presence or Absence of Target Nucleic Acid Molecules

For determining the presence of target analytes in samples, the threshold values for four parameters of a sigmoid function, displacement, $R^2$, and maximum slope were set as follows: displacement≥RFU 100; $R^2$≥0.9; maximum slope≥50; and a4<2.0.

When all of 4 criteria were met, the target analyte was determined to be present in the sample. When any one of 4 criteria was not met, the target analyte was determined to be absent in the sample. As a result of the non-linear fitting analysis for the 12 normalized data sets, it was found that 4 criteria were all met such that the target analytes were determined to be present in all of 12 reaction samples.

TABLE 10

| Channel | 1 | 2 | 3 | 4 | 1 | 2 | 3 | 4 |
|---|---|---|---|---|---|---|---|---|
| | 1. Displacement ≥ RFU 100 | | | | 2. a4 < 2.0 | | | |
| Device 1 | 4806 | 4500 | 4388 | 4570 | 0.29 | 0.30 | 0.23 | 0.29 |
| Device 2 | 4699 | 4469 | 4198 | 4680 | 0.29 | 0.30 | 0.23 | 0.29 |
| Device 3 | 4909 | 4699 | 4491 | 4780 | 0.28 | 0.30 | 0.23 | 0.29 |
| | 3. $R^2$ ≥ 0.9000. | | | | 4. Maximum slope ≥ 50 | | | |
| Device 1 | 0.9997 | 0.9999 | 0.9997 | 0.9998 | 770 | 756 | 561 | 744 |
| Device 2 | 0.9993 | 0.9995 | 0.9990 | 0.9989 | 758 | 742 | 499 | 745 |
| Device 3 | 0.9997 | 0.9999 | 0.9997 | 0.9999 | 785 | 773 | 572 | 770 |

Therefore, it would be realized that data sets may be normalized, baselined and then analyzed by a non-linear fitting function such that the presence or absence of target analytes may be determined in samples.

In the case that a quantification analysis is required by using a threshold value for $C_t$ values, the present invention shows excellent advantages in the senses that noise signals of data sets may be normalized by applying a non-linear fitting function, displacements may be also normalized by the SBN method and therefore threshold values may be easily or uniformly set for different devices or channels in no consideration of device-to device or channel-to-channel signal variation.

FIGS. 17-20 represent results of non-normalized data sets for Channel 1 (FAM), Channel 2 (HEX), Channel 3 (CalRed 610) and Channel 4 (Quasar 670), respectively. As shown in FIGS. 28-31, the non-linear fitting functions to the non-normalized data sets were shown to have higher coefficient of variation (CV) of 49.5%, 51.1%, 44.7%, and 62.6%. The coefficient of variation represents a difference of signal changes between devices.

FIGS. 21-24 represent results of normalized data sets for channel 1 (FAM), channel 2 (HEX), channel 3 (CalRed 610), and channel 4 (Quasar 670), respectively. As shown in FIGS. 21-24, the non-linear functions of the normalized data sets were shown to have much lower coefficient of variation of 2.7%, 4.0%, 5.3%, and 3.7%. $C_t$ values were calculated from the non-linear function curves by using the same threshold value RFU 110 for all devices and channels. As a result, the coefficient of variation of $C_t$ values was 5.7% without normalization and was 1.6% with normalization, demonstrating that the non-linear fitting method together with the SBN method permits to give a quantification data (e.g., $C_t$ values) with dramatically decreased variation between devices and channels.

Tables 11-18 show the data of FIG. 17-24.

TABLE 11

Analytical result without SBN.

| | Device 1 | Device 2 | Device 3 | Total |
|---|---|---|---|---|
| Min. | 2298 | 3643 | 7892 | 2298 |
| Max. | 2939 | 5443 | 9867 | 9867 |
| Range | 641 | 1799 | 1975 | 7569 |
| Mean | 2654 | 4491 | 8893 | 5346 |
| SD | 146 | 421 | 398 | 2645 |
| CV (%) | 5.5% | 9.4% | 4.5% | 49.5% |

TABLE 12

Analytical result without SBN

| | Device 1 | Device 2 | Device 3 | Total |
|---|---|---|---|---|
| Min. | 3103 | 5201 | 10948 | 3103 |
| Max. | 3977 | 7054 | 13923 | 13923 |
| Range | 874 | 1854 | 2975 | 10820 |
| Mean | 3563 | 6026 | 12358 | 7316 |

TABLE 12-continued

Analytical result without SBN

|    | Device 1 | Device 2 | Device 3 | Total |
|----|----------|----------|----------|-------|
| SD | 191 | 419 | 571 | 3735 |
| CV (%) | 5.4% | 7.0% | 4.6% | 51.1% |

TABLE 13

Analytical result without SBN.

|       | Device 1 | Device 2 | Device 3 | Total |
|-------|----------|----------|----------|-------|
| Min.  | 4143 | 9092 | 14285 | 4143 |
| Max.  | 5122 | 12902 | 18112 | 18112 |
| Range | 980 | 3810 | 3827 | 13969 |
| Mean  | 4671 | 10867 | 16051 | 10530 |
| SD    | 225 | 850 | 654 | 4703 |
| CV (%) | 4.8% | 7.8% | 4.1% | 44.7% |

TABLE 14

Analytical result without SBN.

|       | Device 1 | Device 2 | Device 3 | Total |
|-------|----------|----------|----------|-------|
| Min.  | 830 | 2695 | 5338 | 830 |
| Max.  | 1081 | 3557 | 6843 | 6843 |
| Range | 252 | 862 | 1505 | 6014 |
| Mean  | 946 | 3064 | 6020 | 3343 |
| SD    | 49 | 183 | 258 | 2093 |
| CV (%) | 5.2% | 6.0% | 4.3% | 62.6% |

TABLE 15

Analytical result with SBN.

|       | Device 1 | Device 2 | Device 3 | Total |
|-------|----------|----------|----------|-------|
| Min.  | 4806 | 4699 | 4909 | 4699 |
| Max.  | 5529 | 5688 | 5314 | 5688 |
| Range | 723 | 989 | 404 | 989 |
| Mean  | 5170 | 5137 | 5110 | 5139 |
| SD    | 136 | 181 | 64 | 137 |
| CV (%) | 2.6% | 3.5% | 1.3% | 2.7% |

TABLE 16

Analytical result with SBN.

|       | Device 1 | Device 2 | Device 3 | Total |
|-------|----------|----------|----------|-------|
| Min.  | 4500 | 4469 | 4699 | 4469 |
| Max.  | 5573 | 5474 | 5230 | 5573 |
| Range | 1073 | 1004 | 531 | 1103 |
| Mean  | 4986 | 4946 | 4950 | 4961 |
| SD    | 210 | 244 | 117 | 198 |
| CV (%) | 4.2% | 4.9% | 2.4% | 4.0% |

TABLE 17

Analytical result with SBN.

|       | Device 1 | Device 2 | Device 3 | Total |
|-------|----------|----------|----------|-------|
| Min.  | 4388 | 4198 | 4491 | 4198 |
| Max.  | 5342 | 5721 | 5317 | 5721 |
| Range | 955 | 1523 | 827 | 1523 |

TABLE 17-continued

Analytical result with SBN.

|       | Device 1 | Device 2 | Device 3 | Total |
|-------|----------|----------|----------|-------|
| Mean  | 4909 | 4899 | 4903 | 4904 |
| SD    | 219 | 354 | 176 | 260 |
| CV (%) | 4.5% | 7.2% | 3.6% | 5.3% |

TABLE 18

Analytical result with SBN.

|       | Device 1 | Device 2 | Device 3 | Total |
|-------|----------|----------|----------|-------|
| Min.  | 4570 | 4680 | 4780 | 4570 |
| Max.  | 5809 | 6246 | 5300 | 6246 |
| Range | 1239 | 1566 | 520 | 1676 |
| Mean  | 5099 | 5067 | 5030 | 5065 |
| SD    | 225 | 215 | 96 | 189 |
| CV (%) | 4.4% | 4.2% | 1.9% | 3.7% |

Min.: Minimum
Max.: Maximum
Range: Max-Min
SD: Standard Deviation
CV: Coefficient of variation
SBN: Specific Background signal-based Normalization

TABLE 19

| $C_t$ value | channel | 1 | 2 | 3 | 4 | 1 | 2 | 3 | 4 |
|---|---|---|---|---|---|---|---|---|---|
| Analytical result | SBN | − | − | − | − | + | + | + | + |
| (CV %) | Device 1 | 0.4 | 0.5 | 0.5 | 0.4 | 0.3 | 0.4 | 0.5 | 0.4 |
| | Device 2 | 0.6 | 0.6 | 0.9 | 0.7 | 0.5 | 0.5 | 0.7 | 0.8 |
| | Device 3 | 0.5 | 0.5 | 0.4 | 0.3 | 0.4 | 0.4 | 0.4 | 0.2 |
| | Total | 2.9 | 2.9 | 4.2 | 4.5 | 0.4 | 0.5 | 0.5 | 0.6 |
| | Device 1 | | 4.4 | | | | 1.6 | | |
| | Device 2 | | 4.7 | | | | 1.7 | | |
| | Device 3 | | 4.4 | | | | 1.7 | | |
| | Total | | 5.7 | | | | 1.6 | | |

Interestingly, the parameters a3 and a4 which determine the shape of a sigmoid function as well as the $R^2$ value as a fitting accuracy are not changed, when signal intensities are normalized by the SBN method, demonstrating that the SBN method does not affect the non-linear fitting analysis results of the present invention such as the determination of positive or negative samples using the $R^2$ value and the detection of an abnormal signal using the parameter a4. Accordingly, it would be understood that the SBN method is suitable for use in conjunction with the present method using a non-linear fitting function.

Example 4: Detection of Respiratory Infectious Virus I

Obtaining a Data Set

AllPlex™ Respiratory Panel 1 of Seegene, Inc. was used to detect influenza viruses (Flu A and Flu B) and three Flu A subtypes (H1, H1pdm09 and H3), which are major causes of respiratory infections.

Nucleic acid amplification reactions were performed for 10 samples using CFX96™ Real-Time PCR Detection Systems (Bio-Rad). The nucleic acid amplification reaction was performed for a total of 45 cycles of at 95° C. for 10 seconds, at 60° C. for 1 minute and at 72° C. for 10 seconds. PTOCE (WO 2012/096523) and MuDT (WO 2015/147412) technologies were used to obtain data sets from CFX96. The data sets include signal values at all amplification cycles.

The 10 samples are those that had been identified as either positive or negative samples in clinical tests (5 positive samples and 5 negative samples) as shown in Table 20. Sample 1 is infected with Flu A, Sample 2 with Flu B, Sample 4 with Flu A-H1 and Samples 7 and 8 with Flu A-H3 virus.

TABLE 20

| | |
|---|---|
| sample1 | positive |
| sample2 | positive |
| sample3 | negative |
| sample4 | positive |
| sample5 | negative |
| sample6 | negative |
| sample7 | positive |
| sample8 | positive |
| sample9 | negative |
| sample10 | negative |

Generating a First Quadratic Function for the Data Set

The data set for each of the samples was fitted with a first quadratic function, $y=ax^2+bx+c$ by using LM algorithm (Levenberg-Marquardt algorithm; Christian Kanzow et al., JCAM, 172 (2):375(2004)).

Negative Filtering Using a First Quadratic Function
(a) First Negative Filtering Using the Coefficient of the First Quadratic Function

TABLE 21

| Sample | Coefficient of $x^2$ |
|---|---|
| sample1 | 1.808 |
| sample2 | 0.240 |
| sample3 | −0.011 |
| sample4 | 0.866 |
| sample5 | 0.262 |
| sample6 | −0.079 |
| sample7 | 0.481 |
| sample8 | 0.748 |
| sample9 | 0.025 |
| sample10 | 0.032 |

The first quadratic functions for 2 samples among 10 samples were analyzed to have $x^2$ coefficient of less than zero, and the 2 samples (Samples 3 and 6) were filtered out to be negative.
(b) Second Negative Filtering Using $C_{min}$ of the First Quadratic Function The $C_{min}$ is a cycle at which the first quadratic function shows the minimum value.

TABLE 22

| Sample | $C_{min}$ |
|---|---|
| sample1 | 20 |
| sample2 | 23 |
| sample3 | — |
| sample4 | 20 |
| sample5 | 34 |
| sample6 | — |
| sample7 | 1 |
| sample8 | 16 |
| sample9 | 17 |
| sample10 | 45 |

Two of 10 samples (Samples 5 and 10) were shown to have $C_{min}$ of more than 30 and then filtered out to be negative.
Generating a Second Quadratic Function for the Data Set in a Fitting Region Determined Based on $C_{Min}$ The fitting region was determined using the $C_{min}$ for the data set subjected to the negative filtering by the first quadratic function. The minimum fitting cycle was set to 12. When the $C_{min}$ is 12 or less, the fitting region was determined from cycle 1 to cycle 12, and when $C_{min}$ exceeds 12, the fitting region was determined from cycle 1 to $C_{min}$. The second quadratic function was generated in the fitting region of the data set. The second quadratic function is expressed as $y=a(x-50)^2+c$ having a symmetry axis of cycle 50. The data set was fitted with the second quadratic function in the fitting region by using LM algorithm.

Negative Filtering Using the Second Quadratic Function

The results of the negative filtering are summarized in Table 23.

TABLE 23

| Sample | $R^2$ |
|---|---|
| sample1 | 0.993 |
| sample2 | 0.93173 |
| sample3 | — |
| sample4 | 0.996 |
| sample5 | — |
| sample6 | — |
| sample7 | 0.999 |
| sample8 | 0.999 |
| sample9 | −0.131 |
| sample10 | — |

Except for four samples determined to be negative in the negative filtering by the first quadratic function, the fitting accuracy ($R^2$ value) was calculated for the remaining 6 samples by using the data set and the second quadratic function in the fitting region. The $R^2$ value was calculated using Equation V and the threshold value for the $R^2$ value was 0.9. Samples having the $R^2$ value of 0.9 or less were determined to be negative.

As shown in Table 23, the $R^2$ value for one of the 6 samples was found to be less than 0.9 as a negative sample (Sample 9). The remaining 5 samples were amended for the data set by subtracting values of the second quadratic function from signal values of the data sets with the $R^2$ value exceeding 0.9.

Furthermore, the fitting accuracy ($R^2$ value) of a sigmoid fitting function for the amended data set was also calculated. As a result, Samples 1, 2, 4, 7 and 8 were positive since all of $R^2$ values of samples 1, 2, 4, 7 and 8 were 0.9 or more.

Experiment Result 10 samples were analyzed in accordance with the present invention. Among them, 2 samples were determined to be negative using $x^2$ coefficient of the first quadratic function and 2 samples were determined to be negative using $C_{min}$ of the first quadratic function. 1 sample was determined to be negative using the fitting accuracy of the second quadratic function to the data set. The data sets for the remaining 5 samples were amended using the second quadratic function.

Accordingly, the present method allows determining the absence of target analytes in samples in a more convenient and rapid manner by using $x^2$ coefficient and/or $C_{min}$ of the first quadratic function, and the fitting accuracy of the second quadratic function to data sets. Also, data sets may be amended using the second quadratic function to generate a noise-removed data set.

Example 5: Detection of Respiratory Infectious Virus II

Obtaining a Data Set

AllPlex™ Respiratory Panel 1 of Seegene, Inc. was used to detect influenza virus (Flu A) and Flu A subtypes (H1pdm09 and H3), which are major causes of respiratory infections.

Nucleic acid amplification reactions were performed for 4 samples using CFX96™ Real-Time PCR Detection Systems (Bio-Rad). The nucleic acid amplification reaction was performed for a total of 45 cycles of at 95° C. for 10 seconds, at 60° C. for 1 minute and at 72° C. for 10 seconds. PTOCE (WO 2012/096523) and MuDT (WO 2015/147412) technologies were used to obtain data sets from CFX96. The data sets include signal values both at 60° C. as a relatively low detection temperature and at 72° C. as a relatively high detection temperature at all amplification cycles.

The 4 samples are those that had been identified as either positive or negative samples in clinical tests (3 positive samples and 1 negative sample) as shown in Table 24. Sample 1 is infected with Flu A (72° C.), Sample 3 with Flu A-H1pdm09 (60° C.) and Sample 4 with Flu A-H3 (72° C.). Sample 4 contains signal values for internal control at 60° C.

TABLE 24

| Sample | Detection result at 60° C. | Detection result at 72° C. |
| --- | --- | --- |
| sample1 | negative | positive |
| sample2 | negative | negative |
| sample3 | positive | negative |
| sample4 | positive | positive |

Negative Filtering Using Displacement for Data Set at 60° C.

TABLE 25

| Sample | Displacement for data set at 60° C. |
| --- | --- |
| sample1 | 3406.605 |
| sample2 | 24.169 |
| sample3 | 3902.416 |
| sample4 | 2977.709 |

The displacement was calculated as the difference between the signal value at the end cycle and the signal value (minimum signal value) at the cycle with the minimum signal intensity. Sample 2 was filtered out as negative because the displacement was shown not to exceed the threshold value of RFU 100.

Removing Signals for the First Target Nucleic Acid Sequence from Signals Detected at 60° C.

A signal for the second target nucleic acid sequence was extracted from the signal detected at the relatively low detection temperature using (i) the reference value for removing the signal for the first target nucleic acid sequence and (ii) the signal detected at the relatively low detection temperature.

> Signal for second target nucleic acid sequence=[Signal detected at a temperature of 60° C.]−[(signal detected at relatively high detection temperature of 72° C.)×(reference value for first target nucleic acid sequence)]

The reference value for the first target nucleic acid sequence was varied depending on detection channels, and the reference values for Samples 1, 3 and 4 was 1.3, 1.2 and 1.8, respectively.

Negative Filtering Using Signal Displacement

TABLE 26

| Sample | Displacement for second target nucleic acid sequence (60° C.) | Displacement for first target nucleic acid sequence (72° C.) |
| --- | --- | --- |
| sample1 | 55.529 | 2969.266 |
| sample2 | — | — |
| sample3 | 3738.540 | 170.505 |
| sample4 | 671.070 | 1309.855 |

The signal for the second target nucleic acid sequence is the signal extracted from the signal detected at 60° C. In one (Sample 1) of three samples, the difference between the signal value at the last cycle 45 and the minimum signal value for the second target nucleic acid sequence was shown not to exceed the threshold value RFU 100 and therefore the second nucleic acid sequence for Sample 1 was filtered out to be negative.

Generating a Quadratic Function for Signals in a Fitting Region

Each of the signals for the first target nucleic acid sequence and the signals for the second target nucleic acid sequence was fitted with a quadratic function. The fitting region was set from cycles 4 to 12 and the symmetry axis of the quadratic function was set to be cycle 50. The fitting was performed using LM algorithm.

Negative Filtering Using a Fitting Accuracy of the Quadratic Function

TABLE 27

| Sample | Fitting accuracy for second nucleic acid sequence (60° C.) | Fitting accuracy for first nucleic acid sequence (72° C.) |
| --- | --- | --- |
| sample1 | — | 0.999 |
| sample2 | — | — |
| sample3 | 0.999 | 0.990 |
| sample4 | 0.999 | 0.999 |

Except for one sample (Sample 1) determined to be negative in the signal displacement filtering, the fitting accuracy ($R^2$ value) was calculated for the remaining samples by using the quadratic function in the fitting region. The $R^2$ value was calculated using Equation V and the threshold value for the $R^2$ value was 0.9. Samples having the $R^2$ value of 0.9 or less were determined to be negative.

As shown in the Table 27, data sets of samples with $R^2$ values of exceeding 0.9 was amended by subtracting values of the quadratic function from signal values of the data set.

Negative Filtering Using a Non-Linear Fitting Function

TABLE 28

| | Second target (60° C.) | | | First target (72° C.) | | |
| --- | --- | --- | --- | --- | --- | --- |
| Sample | $R^2$ | ΔRFU | df | $R^2$ | ΔRFU | df |
| sample1 | — | — | — | 0.998 | 3063 | 338 |
| sample2 | — | — | — | — | — | — |
| sample3 | 0.998 | 3616 | 311 | 0.990 | 200 | 14 |
| sample4 | 0.996 | 568 | 61 | 0.999 | 1330 | 179 |

(a) Generation of Sigmoid Function

The amended data set was fitted with a sigmoid function by using the four-parametric sigmoid function of Equation III. The LM algorithm was used to obtain a sigmoid function fitted to the amended data set.

(b) First Negative Filtering by the Displacement of the Sigmoid Fitting Function The displacement of the sigmoid function was used to filter out negative samples. The displacement of the sigmoid fitting function was obtained by calculating the difference between the maximum signal value and the minimum signal value of the sigmoid fitting function. The negative samples were filtered out by comparing the calculated displacement with a threshold value for displacement (RFU 100). The displacements for all samples were calculated to exceed the threshold value of 100.

(c) Second Negative Filtering by a Maximum Slope of the Sigmoid Fitting Function The second negative filtering using the maximum slope of the sigmoid fitting function was carried out. The maximum slope was calculated by differentiating the sigmoid fitting function for each sample. The threshold value for the maximum slope was set as 28. As shown in Table 28, the maximum slope of the sigmoid fitting to the signal for the first target nucleic acid sequence of Sample 3 was less than 30 and thus the first target nucleic acid sequence of Sample 3 was filtered out to be negative.

(d) Final Decision of Positive or Negative Samples by a Fitting Accuracy $R^2$ Value $R^2$ value was used as the fitting accuracy. $R^2$ value was calculated using Equation IV and the threshold value for $R^2$ value was set 0.90. Samples having $R^2$ values exceeding 0.90 were determined to be positive.

Experiment Result

Four samples were analyzed by the present invention using a non-linear fitting function in conjunction with the MuDT technology. One sample (Sample 2) was filtered out to be negative in which the displacement of signals detected at a relatively low detection temperature was less than the threshold value (RFU 100). Sample 2 was determined that both the first target nucleic acid sequence and the second target nucleic acid sequence were absent.

The signal for the second target nucleic acid sequence was extracted for 3 samples except for Sample 2, and the displacement of the signal for the first target nucleic acid sequence and the displacement of the signal for the second target nucleic acid sequence were compared with the threshold value (RFU 100). The signal for the second target nucleic acid sequence of Sample 1 having a displacement not exceeding the threshold value was filtered out to be negative.

The sigmoid functions for the signals not filtered to be negative were generated. The signal for the first target nucleic acid sequence of Sample 3 was filtered out to be negative since the maximum slope of the sigmoid function for Sample 3 did not exceed the threshold value 30.

The $R^2$ value between the sigmoid function and the signals was calculated, and all the remaining signals were filtered to be positive since the $R^2$ values of all the remaining signals exceeded the threshold value 0.90.

According to the present invention, the absence of two target nucleic acid sequences having different detection temperatures may be determined by comparing the threshold value with the displacement of the detected signal at the relatively low detection temperature. The present invention permits to determine the presence or absence of the second target nucleic acid sequence by extracting the signal for the second target nucleic acid sequence irrespective of the displacement of the signal detected at the relatively high detection temperature. The present invention enables to determine the presence or absence of both the first target nucleic acid sequence and the second target nucleic acid sequence by using a sigmoid fitting function.

Having described a preferred embodiment of the present invention, it is to be understood that variants and modifications thereof falling within the spirit of the invention may become apparent to those skilled in this art, and the scope of this invention is to be determined by appended claims and their equivalents.

What is claimed is:

1. A method for analyzing a target analyte in a sample, comprising:
    obtaining a data set for the target analyte; wherein the data set is obtained from a signal-generating reaction using a signal-generating means and comprises a plurality of data points including cycle numbers and signal values;
    amending the data set;
    generating a sigmoid function to the amended data set;
    determining a fitting accuracy of the sigmoid function to the amended data set, wherein the fitting accuracy is $R^2$ (R-square value) of the sigmoid function to the amended data set; and
    determining the presence or absence of the target analyte in the sample using the fitting accuracy, wherein the determination of the presence or absence of the target analyte in the sample is performed by comparing the $R^2$ (R-square value) of the sigmoid function determined for the amended data set with a pre-determined threshold value.

2. The method according to claim 1, wherein the sigmoid function is a four-parametric sigmoid function represented by Equation III:

$$f(x) = a_1 + \frac{a_2 - a_1}{1 + 10^{a_4(a_3 - x)}} \qquad \text{Equation III}$$

where f(x) represents a sigmoid function as a fit function; x represents a cycle number of the signal-generating reaction; and each of a1, a2, a3, and a4 independently represents a parameter of the sigmoid function.

3. The method according to claim 1, wherein the determination of the presence or absence of the target analyte in the sample is performed by comparing the fitting accuracy determined for the amended data set with the pre-determined threshold value to evaluate whether the fitting accuracy exceeds the pre-determined threshold value.

4. The method according to claim 1, wherein the determination of the presence or absence of the target analyte in the sample is performed by additionally using at least one parameter selected from the group consisting of (i) a displacement of the data set, the amended data set or the non-linear function and (ii) a maximum slope of the non-linear function.

5. The method according to claim 2, wherein the determination of the presence or absence of the target analyte in the sample is performed by additionally using at least one parameter selected from the group consisting of (i) a displacement of the data set, the amended data set or the four-parametric sigmoid function and (ii) a maximum slope and a4 of the four-parametric sigmoid function.

6. The method according to claim 1, wherein the target analyte is a target nucleic acid molecule.

7. The method according to claim 6, wherein the signal-generating reaction is a process amplifying a signal value with or without an amplification of the target nucleic acid molecule.

8. The method according to claim 7, wherein the signal-generating means generates a signal in a dependent manner on the formation of a duplex.

9. The method according to claim 7, wherein the signal-generating means generates a signal in a dependent manner on cleavage of a detection oligonucleotide.

10. The method according to claim 1, wherein the amending the data set is performed by the steps comprising:
generating a normalization coefficient using (i) a signal value at a reference cycle or (ii) a change value of the signal value at the reference cycle; and
generating the amended data set by applying the normalization coefficient to signal values of the data set.

11. The method according to claim 10, wherein the signal-generating reaction comprises a plurality of signal-generating reactions for an identical target analyte in different reaction environments; wherein the data set is a plurality of data sets obtained from the plurality of sets from the plurality of signal-generating reactions; and wherein the reference cycle or the reference cycle plus the reference value are applied to the plurality of data sets in the same manner.

12. The method according to claim 11, wherein the plurality of signal-generating reactions are performed in different reaction environments comprising different devices, different reaction tubes or wells, different samples, different amounts of the target analyte or difference primers or probes from each other.

13. The method according to claim 10, wherein the amended data set is generated (i) by generating a normalized data set by applying the normalization coefficient to the data set or (ii) by baselining the data set or the normalized data set.

14. The method according to claim 1, wherein the data set comprises (i) a signal for a first target nucleic acid sequence that is a signal detected at a relatively high detection temperature and/or (ii) a signal for a second target nucleic acid sequence extracted from a signal detected at a relatively low detection temperature, and wherein the first target nucleic acid sequence and the second target nucleic acid sequence are detected from a single reaction vessel.

15. The method according to claim 14, wherein the signal for the first target nucleic acid sequence and the signal for the second target nucleic acid sequence are obtained by the following steps:
(a) incubating a first signal-generating means capable of generating the signal for the first target nucleic acid sequence and a second signal-generating means capable of generating the signal for the second target nucleic acid sequence in the reaction vessel with the sample and detecting signals at the relatively high detection temperature and at the relatively low detection temperature;
wherein each of the first target nucleic acid sequence and the second target nucleic acid sequence is detected by a corresponding signal-generating means,
wherein the first signal-generating means generates a signal at the relatively high detection temperature and the relatively low detection temperature when the first target nucleic acid sequence exists in the sample, and
wherein the second signal-generating means generates a signal at the relatively low detection temperature when the second target nucleic acid sequence exists in the sample,
(b) identifying whether a signal detected at the relatively low detection temperature satisfies a first criterion defined by a first threshold or a first signal displacement; wherein when the signal detected at the relatively low detection temperature satisfies the first criterion, a step (c) is further performed and wherein when the signal detected at relatively low detection temperature does not satisfy the first criterion, the first target nucleic acid sequence and the second target nucleic acid sequence are determined to be absent in the sample and the step (c) is not performed; and,
(c) extracting the signal for the second target nucleic acid sequence from the signal detected at the relatively low detection temperature using (i) a reference value for removing the signal for the first target nucleic acid sequence from the signal detected at the relatively low detection temperature and (ii) the signal detected at the relatively low detection temperature.

16. The method according to claim 15, wherein the signal for the second target nucleic acid sequence is provided by Equation VI:

Signal for the second target nucleic acid sequence= [the signal detected at relatively low detection temperature]−[(the signal detected at the relatively high detection temperature)×(the reference value for the first target nucleic acid sequence)].                                       Equation VI 17. The method according to claim 13, wherein the baselining is performed by using a quadratic function having a symmetry axis.

18. A computer readable storage medium containing instructions to configure a processor to perform a method, the method comprising:
obtaining a data set for the target analyte; wherein the data set is obtained from a signal-generating reaction using a signal-generating means and includes a plurality of data points including cycle numbers and signal values, amending the data set;
generating a sigmoid function to the amended data set;
determining a fitting accuracy of the sigmoid function to the amended data set, wherein the fitting accuracy is $R^2$ (R-square value) of the sigmoid function to the amended data set; and
determining the presence or absence of the target analyte in the sample using the fitting accuracy, wherein the determination of the presence or absence of the target analyte in the sample is performed by comparing the $R^2$ (R-square value) of the sigmoid function for the amended data set with a pre-determined threshold value.

* * * * *